(12) United States Patent
Brett et al.

(10) Patent No.: US 7,753,935 B2
(45) Date of Patent: Jul. 13, 2010

(54) INTERVENTIONAL MEDICAL CLOSURE DEVICE

(75) Inventors: Gerard Brett, Claregalway (IE); David Ronan, Tuam (IE); Liam Mulloy, Maunsells Park (IE); Steven Horan, Athlone (IE)

(73) Assignee: Vivasure Medical Limited, Galway (IE)

( * ) Notice: Subject to any disclaimer, the term of this patent is extended or adjusted under 35 U.S.C. 154(b) by 567 days.

(21) Appl. No.: 11/413,636

(22) Filed: Apr. 28, 2006

(65) Prior Publication Data

US 2006/0287673 A1 Dec. 21, 2006

Related U.S. Application Data

(60) Provisional application No. 60/676,279, filed on Apr. 29, 2005.

(51) Int. Cl.
 *A61B 17/08* (2006.01)
(52) U.S. Cl. ..................................................... 606/213
(58) Field of Classification Search .............. 623/23.72; 606/213, 232
 See application file for complete search history.

(56) References Cited

U.S. PATENT DOCUMENTS

| 3,874,388 | A | * | 4/1975 | King et al. ................... 606/232 |
| 4,744,364 | A | * | 5/1988 | Kensey ........................ 606/213 |
| 4,852,568 | A | * | 8/1989 | Kensey ........................ 606/213 |
| 4,890,612 | A | * | 1/1990 | Kensey ........................ 606/213 |
| 4,896,668 | A | * | 1/1990 | Popoff et al. ................... 606/74 |
| 5,021,059 | A | * | 6/1991 | Kensey et al. ................ 606/213 |
| 5,127,412 | A | * | 7/1992 | Cosmetto et al. ............. 128/898 |
| 5,342,393 | A | * | 8/1994 | Stack .......................... 606/213 |
| 5,501,700 | A | * | 3/1996 | Hirata ......................... 606/215 |
| 5,527,322 | A | * | 6/1996 | Klein et al. .................. 606/144 |
| 5,531,759 | A | * | 7/1996 | Kensey et al. ................ 606/213 |
| 5,545,178 | A | * | 8/1996 | Kensey et al. ................ 606/213 |
| 5,549,633 | A |   | 8/1996 | Evans et al. |
| 5,593,422 | A | * | 1/1997 | Muijs Van de Moer et al. .. 606/213 |
| 5,601,557 | A | * | 2/1997 | Hayhurst ..................... 606/232 |
| 5,620,461 | A | * | 4/1997 | Muijs Van De Moer et al. .. 606/213 |
| 5,700,273 | A | * | 12/1997 | Buelna et al. ................ 606/148 |
| 5,700,277 | A | * | 12/1997 | Nash et al. ................... 606/213 |
| 5,707,393 | A | * | 1/1998 | Kensey et al. ................ 606/213 |
| 5,755,727 | A | * | 5/1998 | Kontos ........................ 606/144 |
| 5,782,861 | A |   | 7/1998 | Cragg et al. |
| 5,814,065 | A | * | 9/1998 | Diaz ........................... 606/213 |
| 5,860,990 | A |   | 1/1999 | Nobles |

(Continued)

*Primary Examiner*—(Jackie) Tan-Uyen T Ho
*Assistant Examiner*—Son Dang
(74) *Attorney, Agent, or Firm*—Choate, Hall & Stewart, LLP; John D. Lanza

(57) ABSTRACT

An interventional medical closure device is suitable for assisting closure of an opening through a blood vessel wall after completion of an interventional procedure within the internal lumen of the blood vessel. The device comprises a closure element, a grasping element for grasping the closure element, and a delivery element for delivering the closure element into the internal lumen of the blood vessel. The closure element comprises a suture, and an engagement foot at a distal end of the suture. The grasping element is interengageable with the closure element to grasp the closure element. The delivery element comprises a main body portion, and a distal nose. The distal nose defines a reception space for carrying the engagement foot of the closure element. The delivery element also comprises an engagement foot which is movable relative to the main body portion between a low-profile delivery configuration and a protruding engagement configuration.

4 Claims, 77 Drawing Sheets

U.S. PATENT DOCUMENTS

| | | | |
|---|---|---|---|
| 5,916,236 A * | 6/1999 | Muijs Van de Moer et al. | 606/213 |
| 5,935,147 A * | 8/1999 | Kensey et al. | 606/213 |
| 6,033,427 A | 3/2000 | Lee | |
| 6,056,768 A * | 5/2000 | Cates et al. | 606/213 |
| 6,126,675 A | 10/2000 | Shchervinsky | |
| 6,136,010 A | 10/2000 | Modesitt | |
| 6,179,863 B1 * | 1/2001 | Kensey et al. | 606/215 |
| 6,190,400 B1 * | 2/2001 | Van De Moer et al. | 606/213 |
| 6,296,658 B1 * | 10/2001 | Gershony et al. | 606/213 |
| 6,425,911 B1 * | 7/2002 | Akerfeldt et al. | 606/213 |
| 6,461,364 B1 | 10/2002 | Ginn | |
| 6,508,828 B1 | 1/2003 | Akerfeldt | |
| 6,764,500 B1 * | 7/2004 | Muijs Van De Moer et al. | 606/213 |
| 6,860,895 B1 | 3/2005 | Akerfeldt | |
| 6,890,342 B2 | 5/2005 | Zhu | |
| 6,932,824 B1 | 8/2005 | Roop | |
| 6,939,363 B2 | 9/2005 | Akerfeldt | |
| 6,942,674 B2 | 9/2005 | Belef | |
| 6,949,107 B2 | 9/2005 | McGuckin | |
| 6,949,114 B2 | 9/2005 | Milo | |
| 6,964,668 B2 * | 11/2005 | Modesitt et al. | 606/144 |
| 6,969,397 B2 * | 11/2005 | Ginn | 606/213 |
| 6,984,219 B2 | 1/2006 | Ashby | |
| 6,989,022 B2 | 1/2006 | Nowakowski | |
| 6,997,940 B2 * | 2/2006 | Bonutti | 606/232 |
| 7,001,398 B2 | 2/2006 | Carley | |
| 7,001,400 B1 | 2/2006 | Modesitt | |
| 7,008,440 B2 | 3/2006 | Sing | |
| 7,008,441 B2 | 3/2006 | Zucker | |
| 7,008,442 B2 | 3/2006 | Brightbill | |
| 7,169,168 B2 * | 1/2007 | Muijs Van De Moer et al. | 606/213 |
| 2002/0019649 A1 | 2/2002 | Sikora | |
| 2003/0078598 A1 | 4/2003 | Ginn | |
| 2003/0093093 A1 * | 5/2003 | Modesitt et al. | 606/144 |
| 2004/0092964 A1 | 5/2004 | Modesitt et al. | |
| 2004/0093025 A1 | 5/2004 | Egnelov | |
| 2004/0176798 A1 | 9/2004 | Epstein | |
| 2004/0243122 A1 * | 12/2004 | Auth et al. | 606/41 |
| 2005/0021055 A1 | 1/2005 | Toubia et al. | |
| 2005/0209613 A1 | 9/2005 | Roop | |
| 2005/0251201 A1 * | 11/2005 | Roue et al. | 606/213 |
| 2005/0267520 A1 | 12/2005 | Modesitt | |
| 2008/0312646 A9 * | 12/2008 | Auth et al. | 606/41 |

* cited by examiner

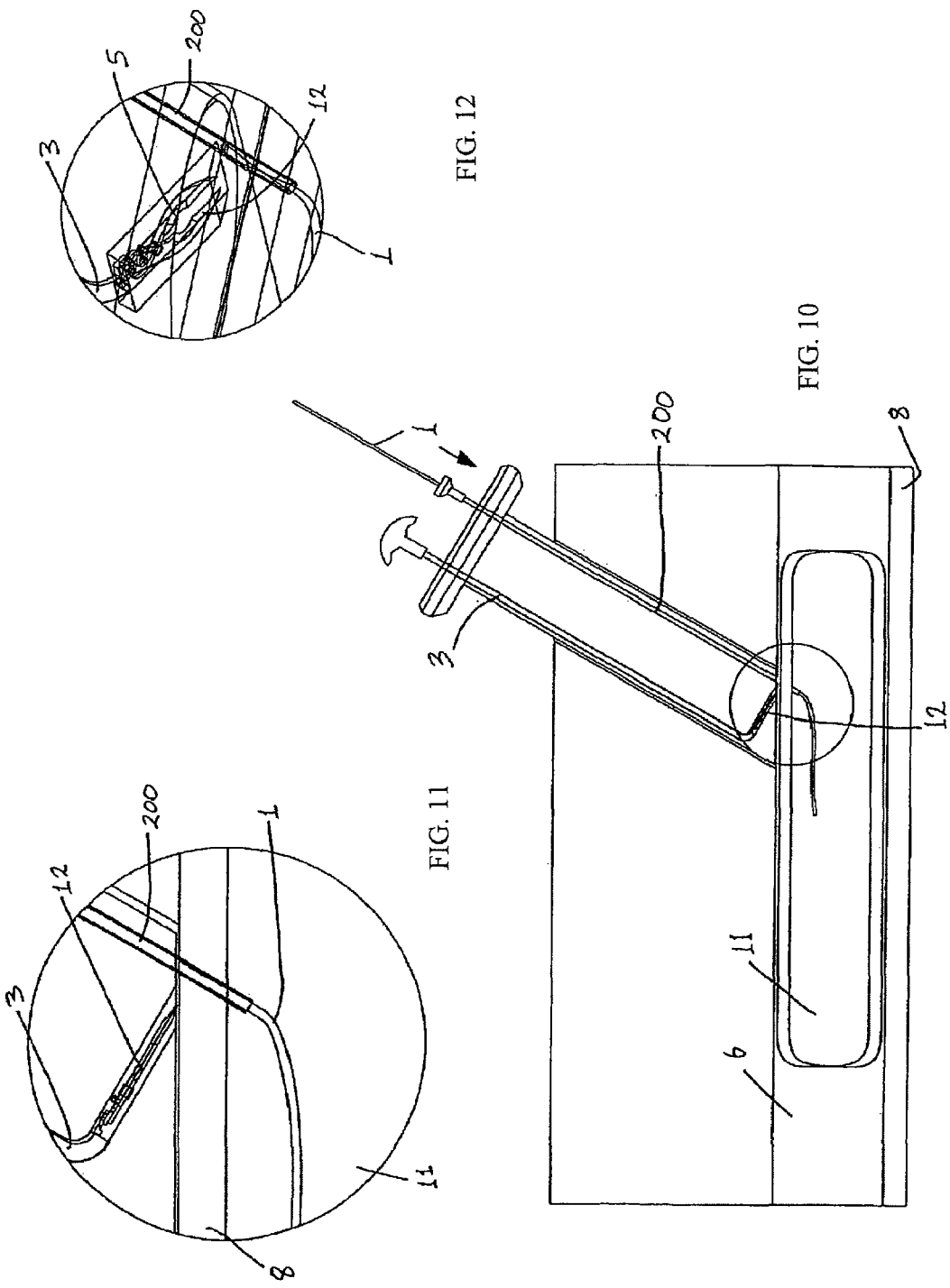

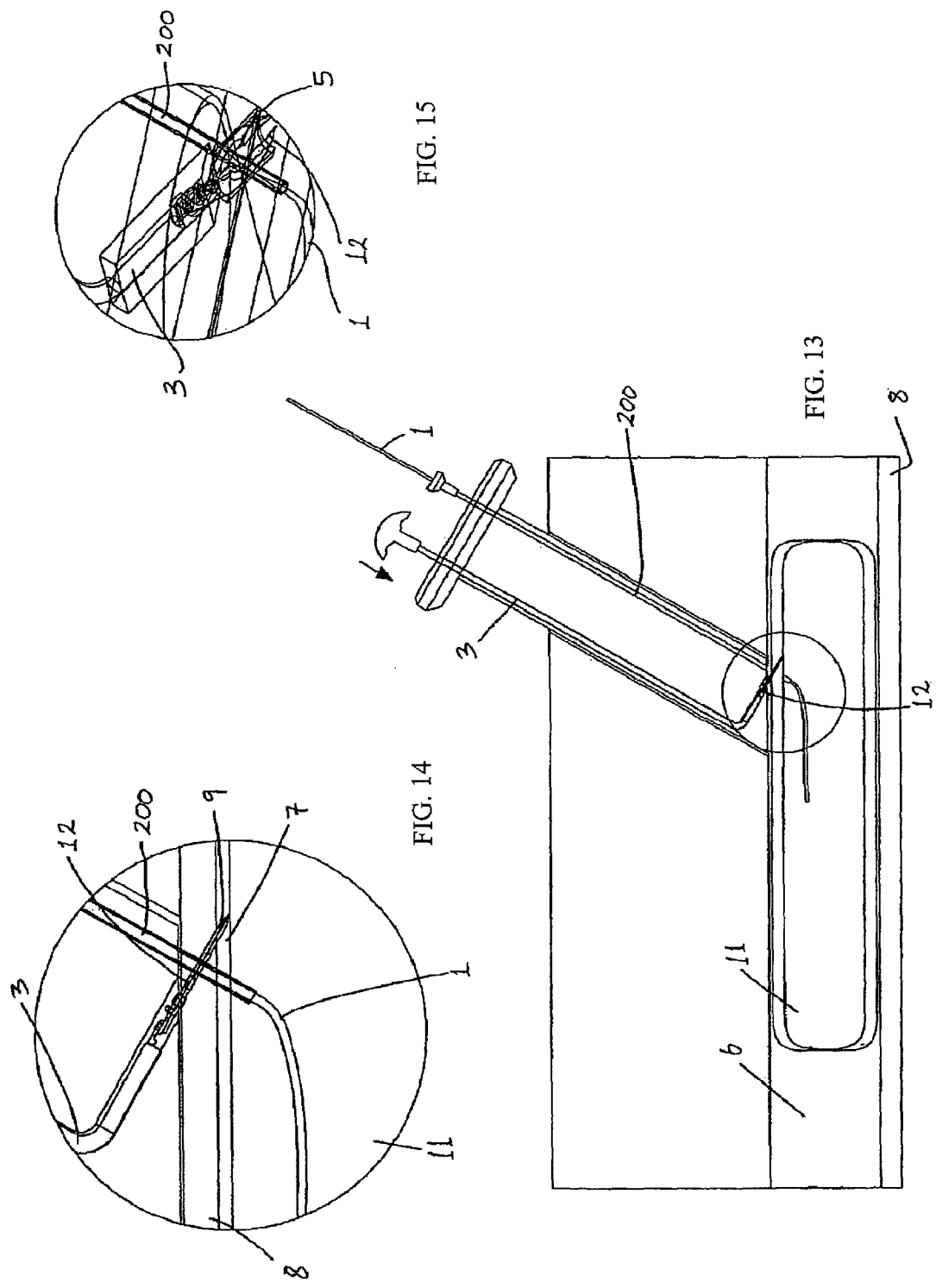

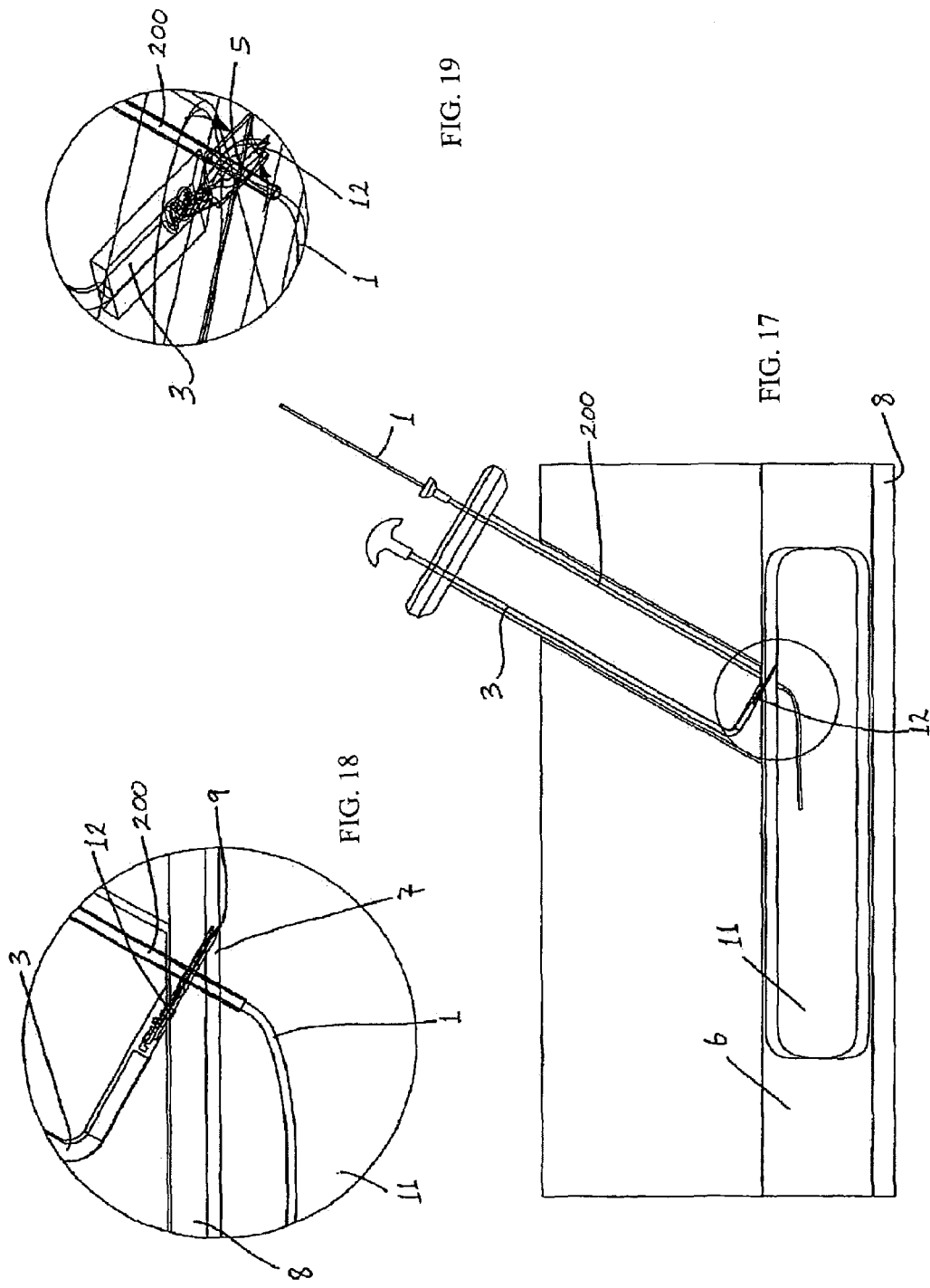

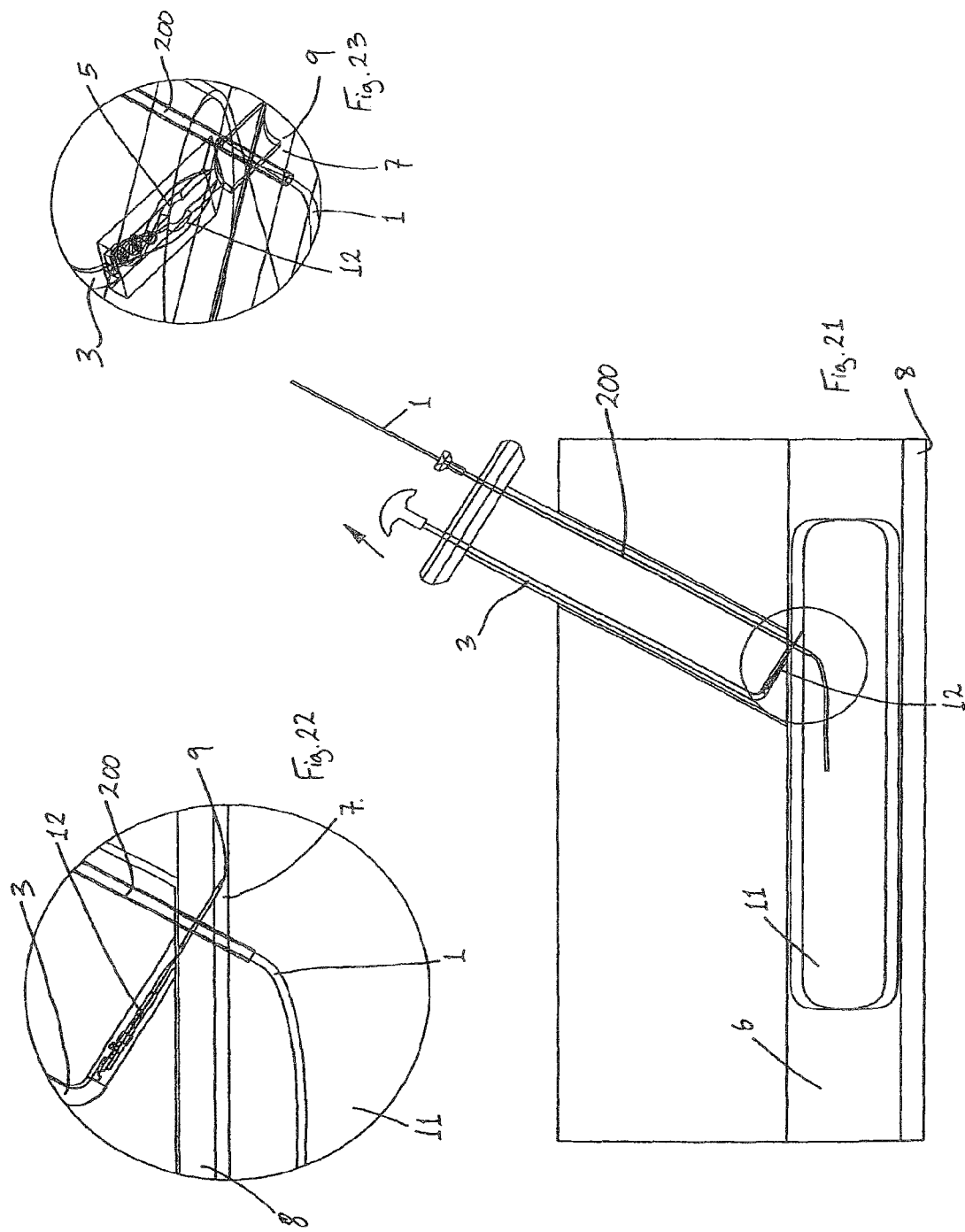

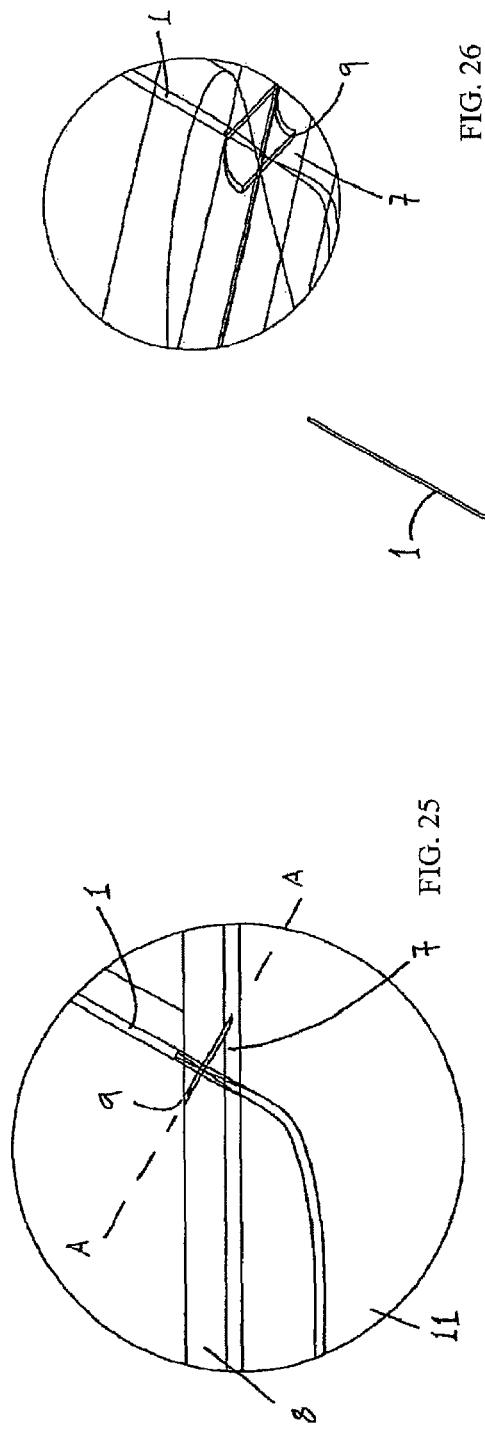

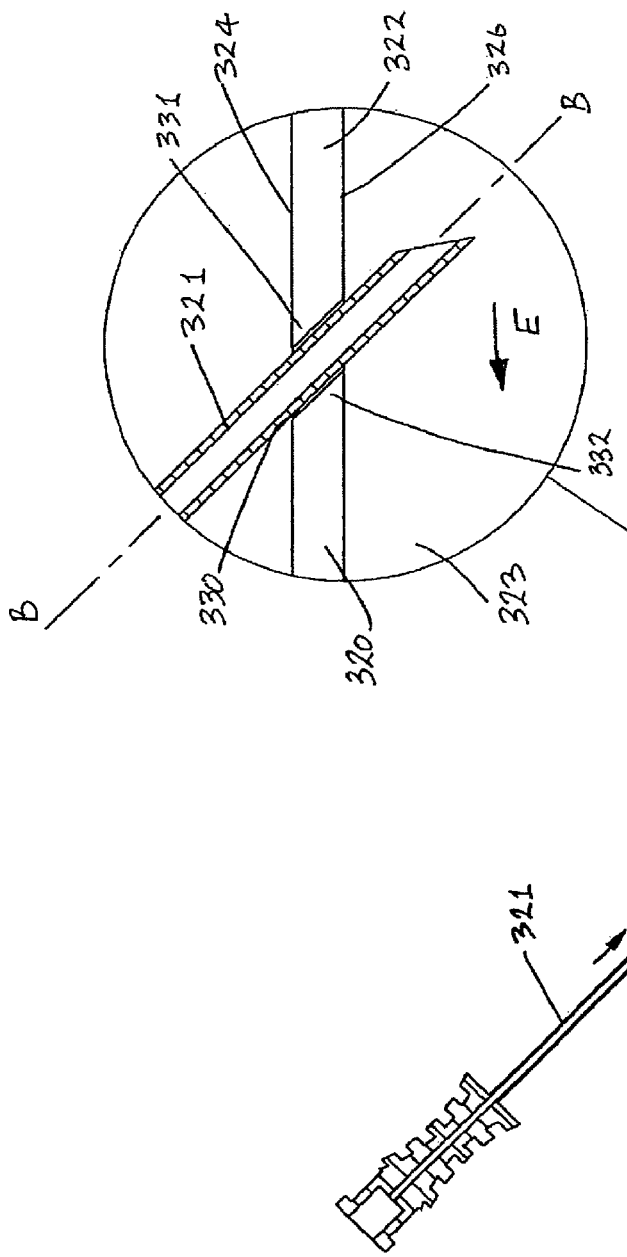
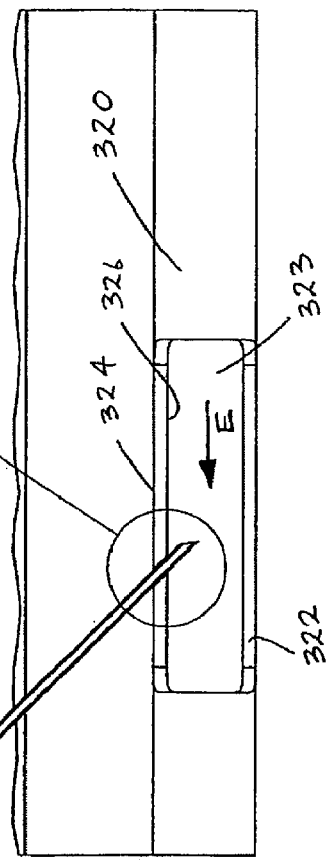
FIG. 75
FIG. 74

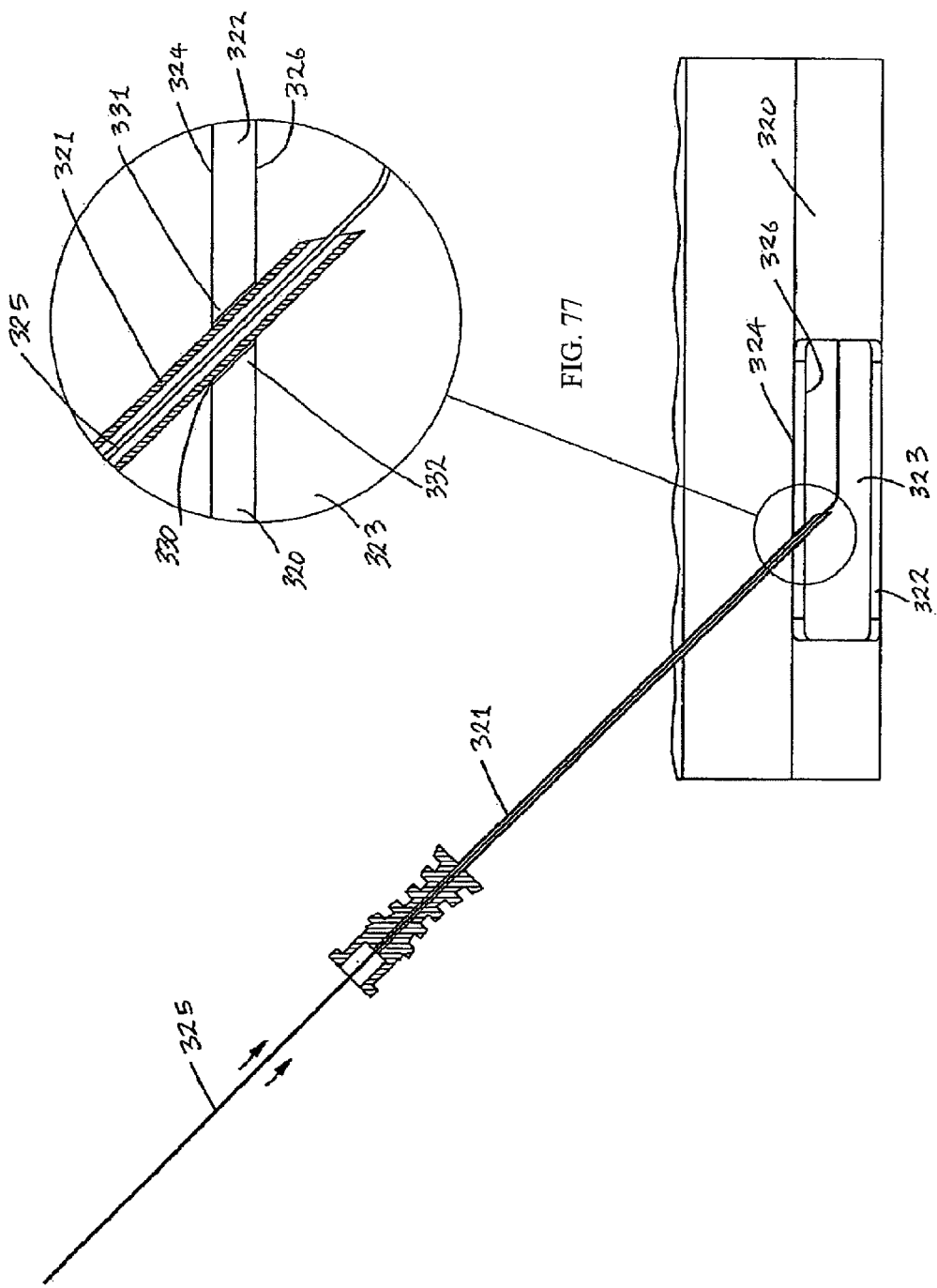

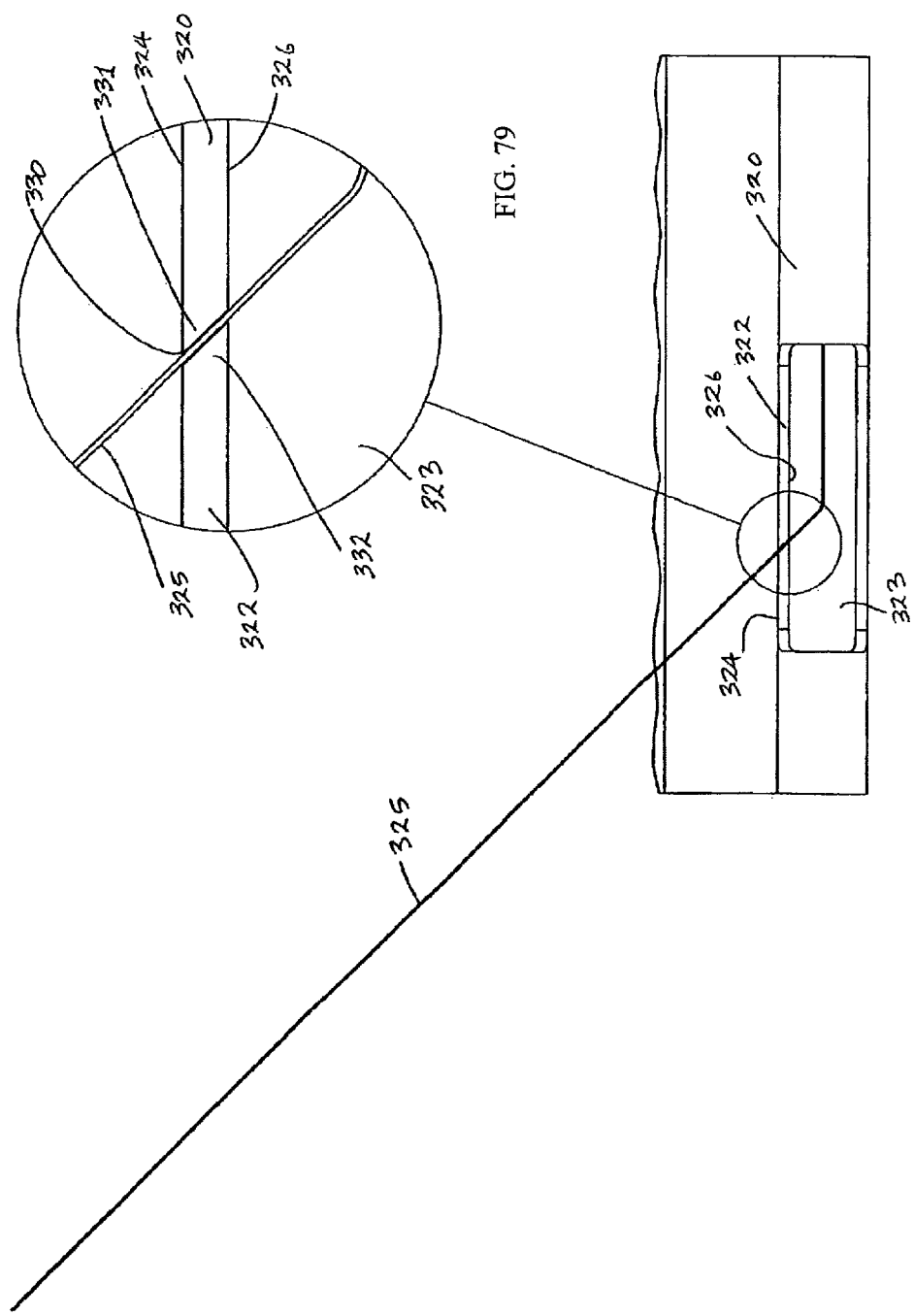

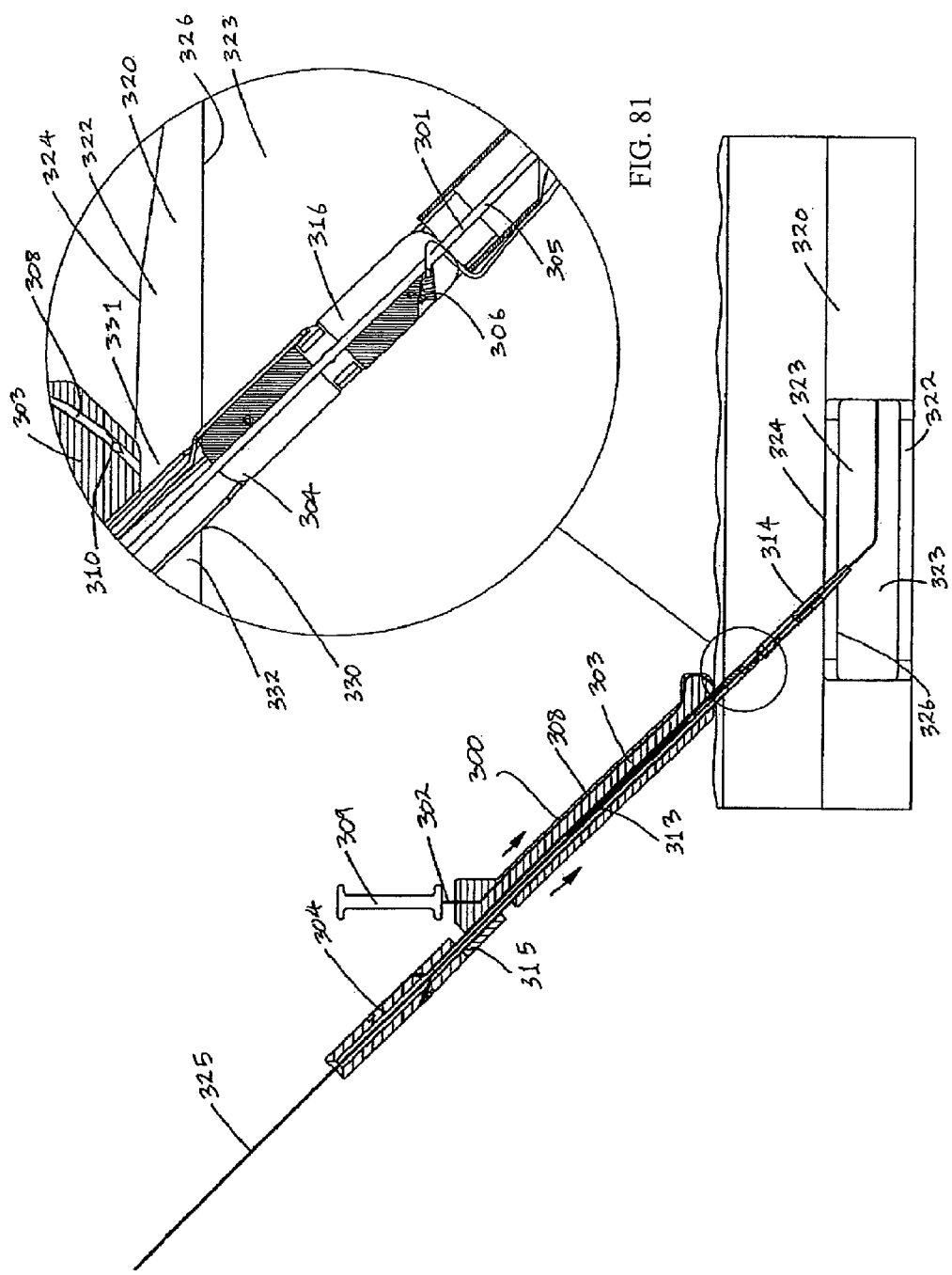

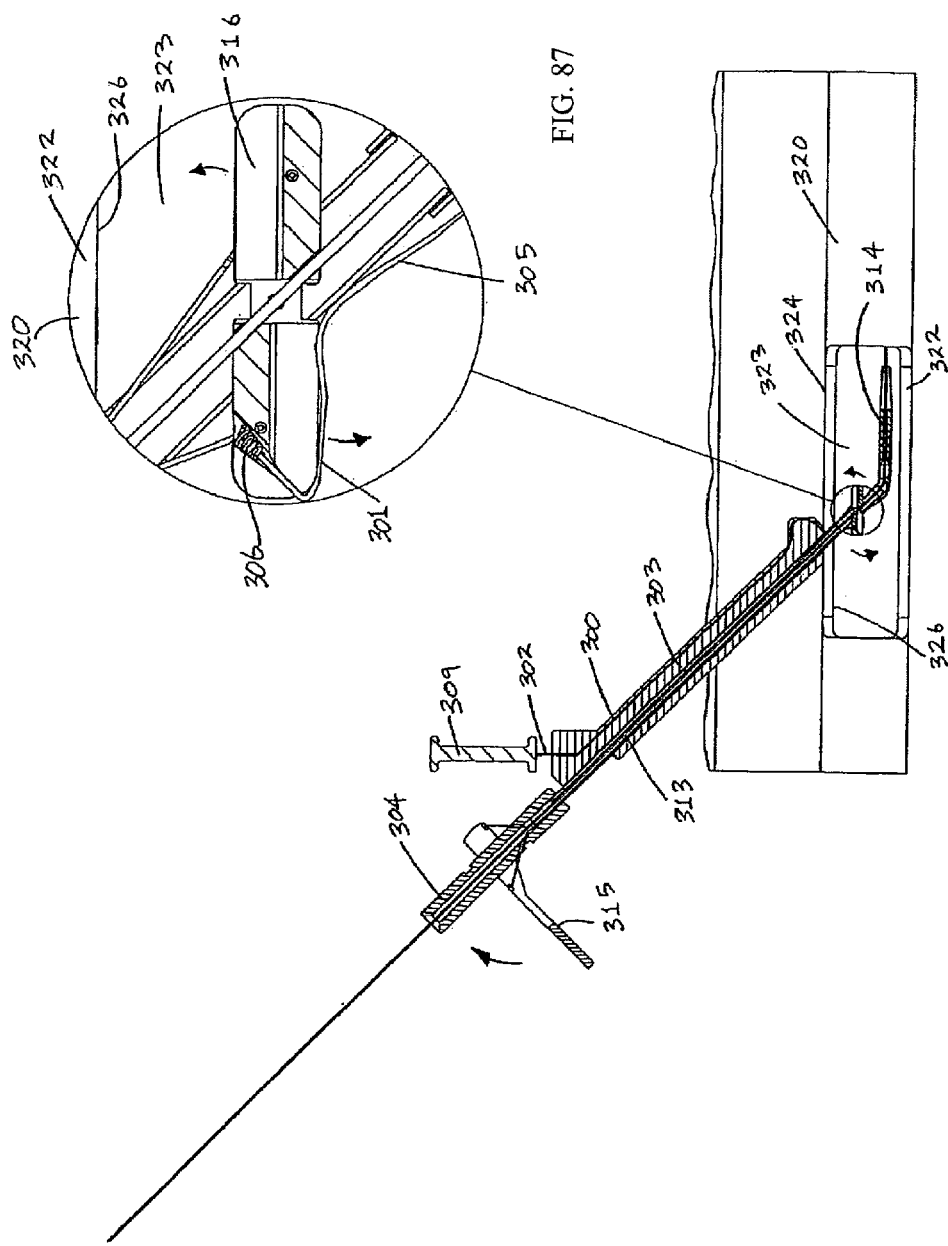

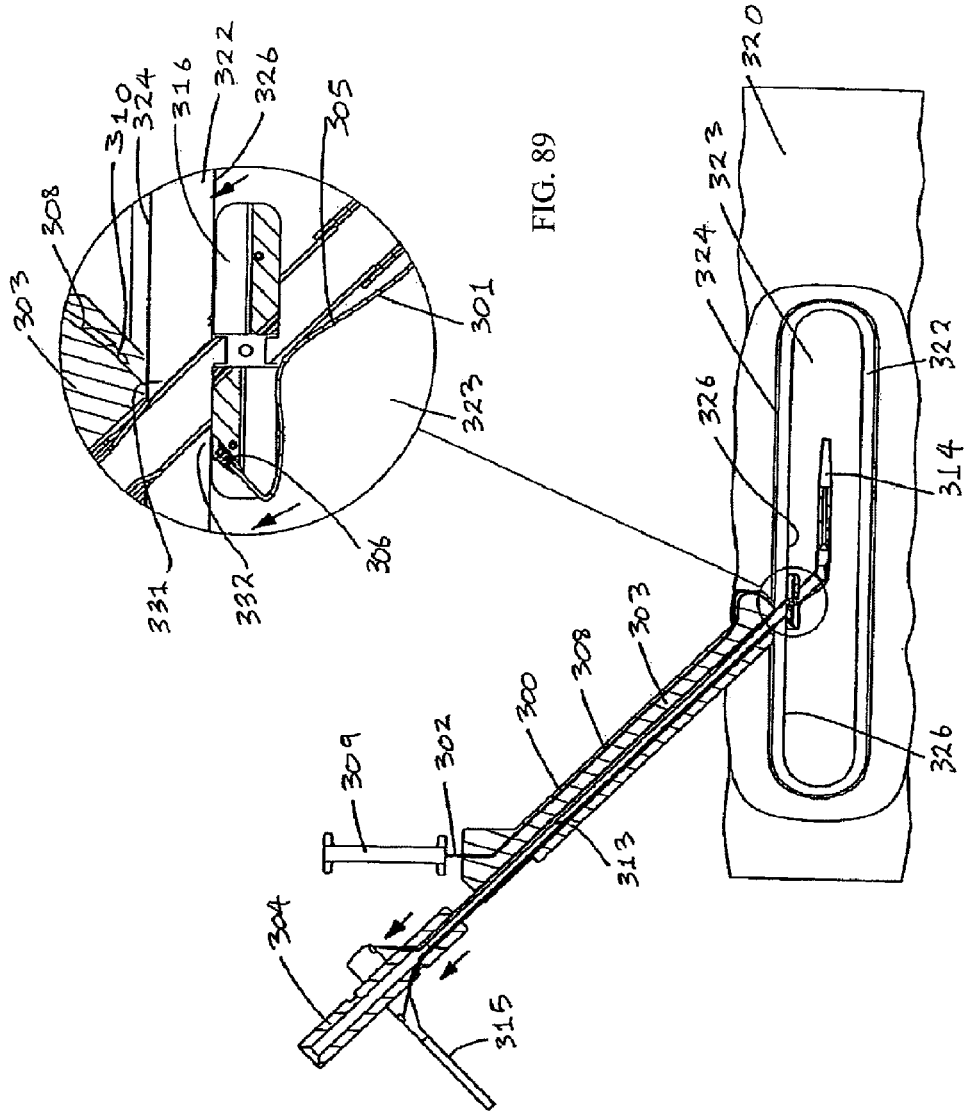

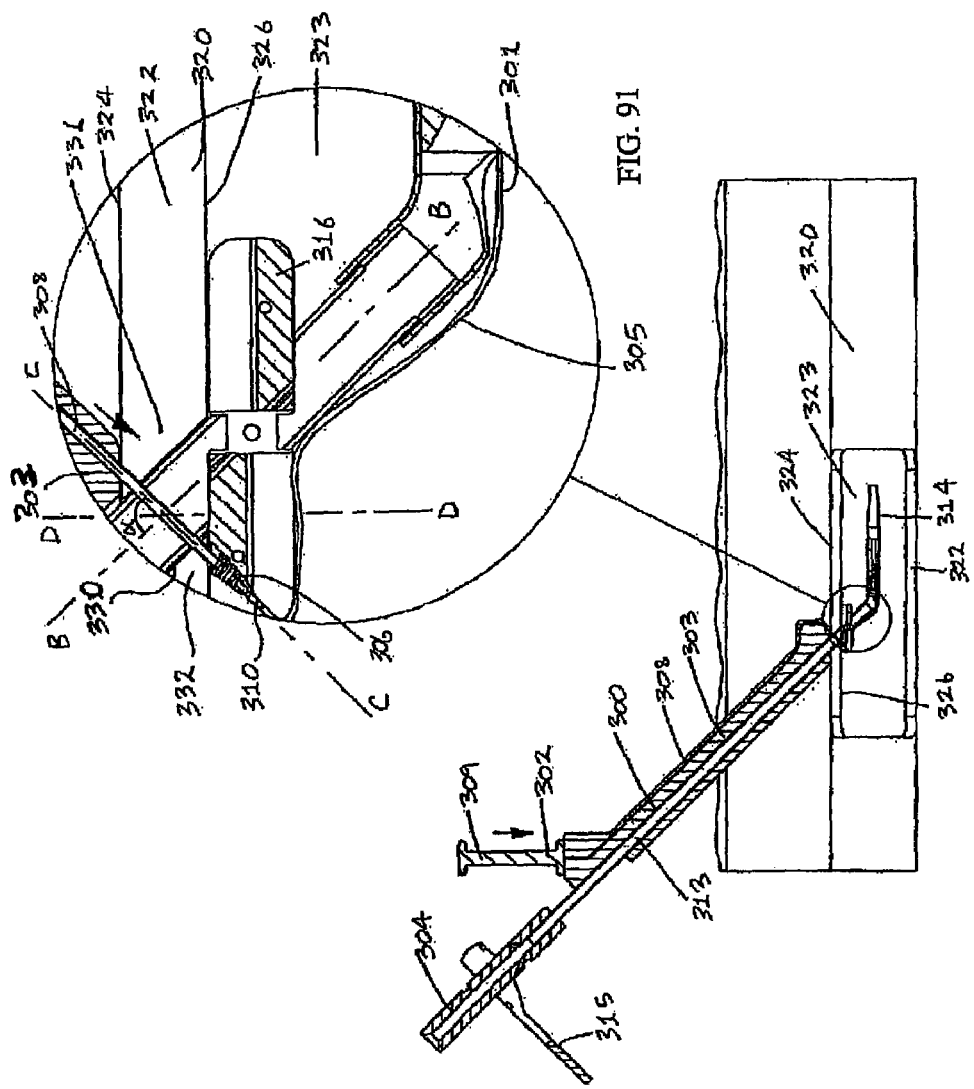

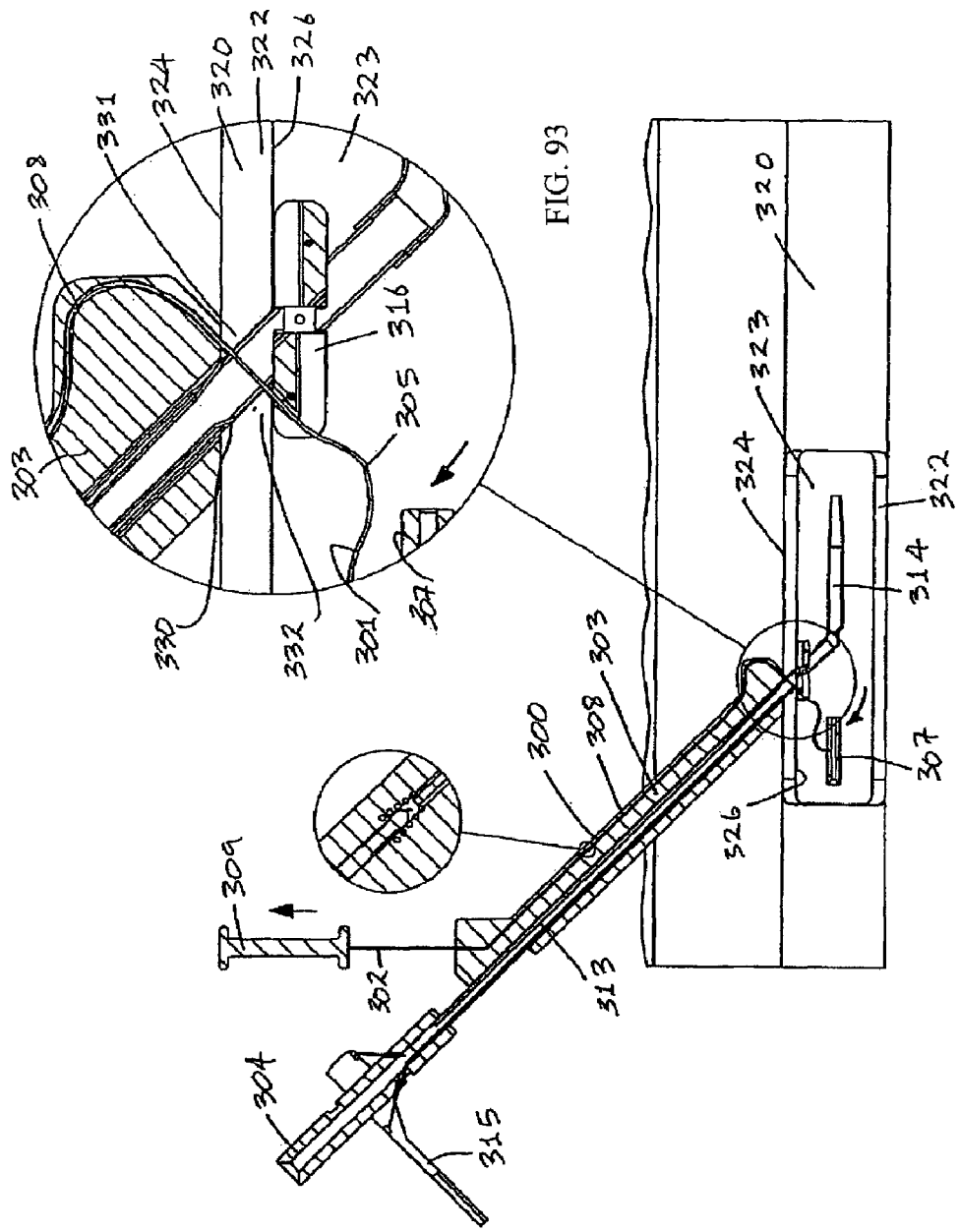

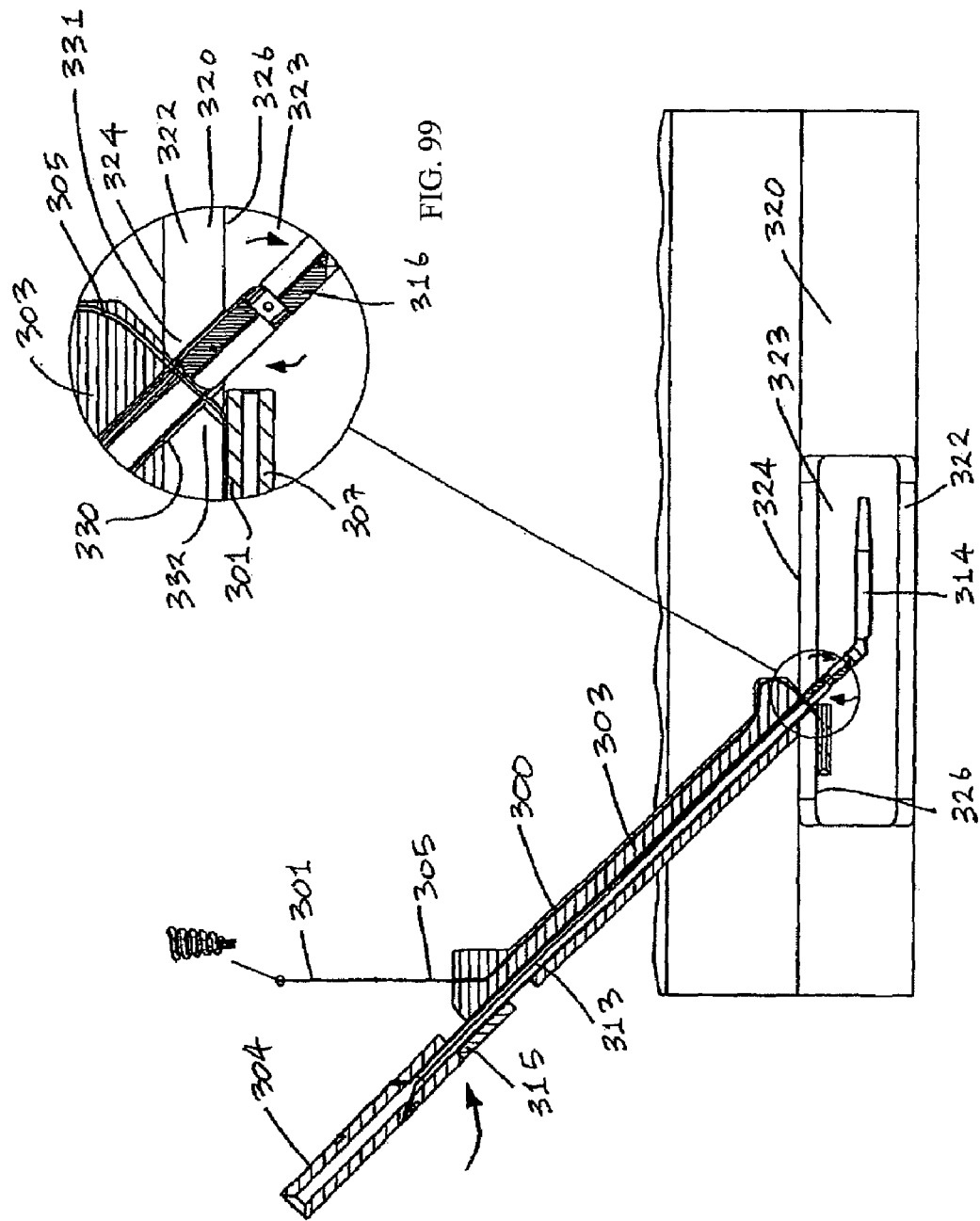

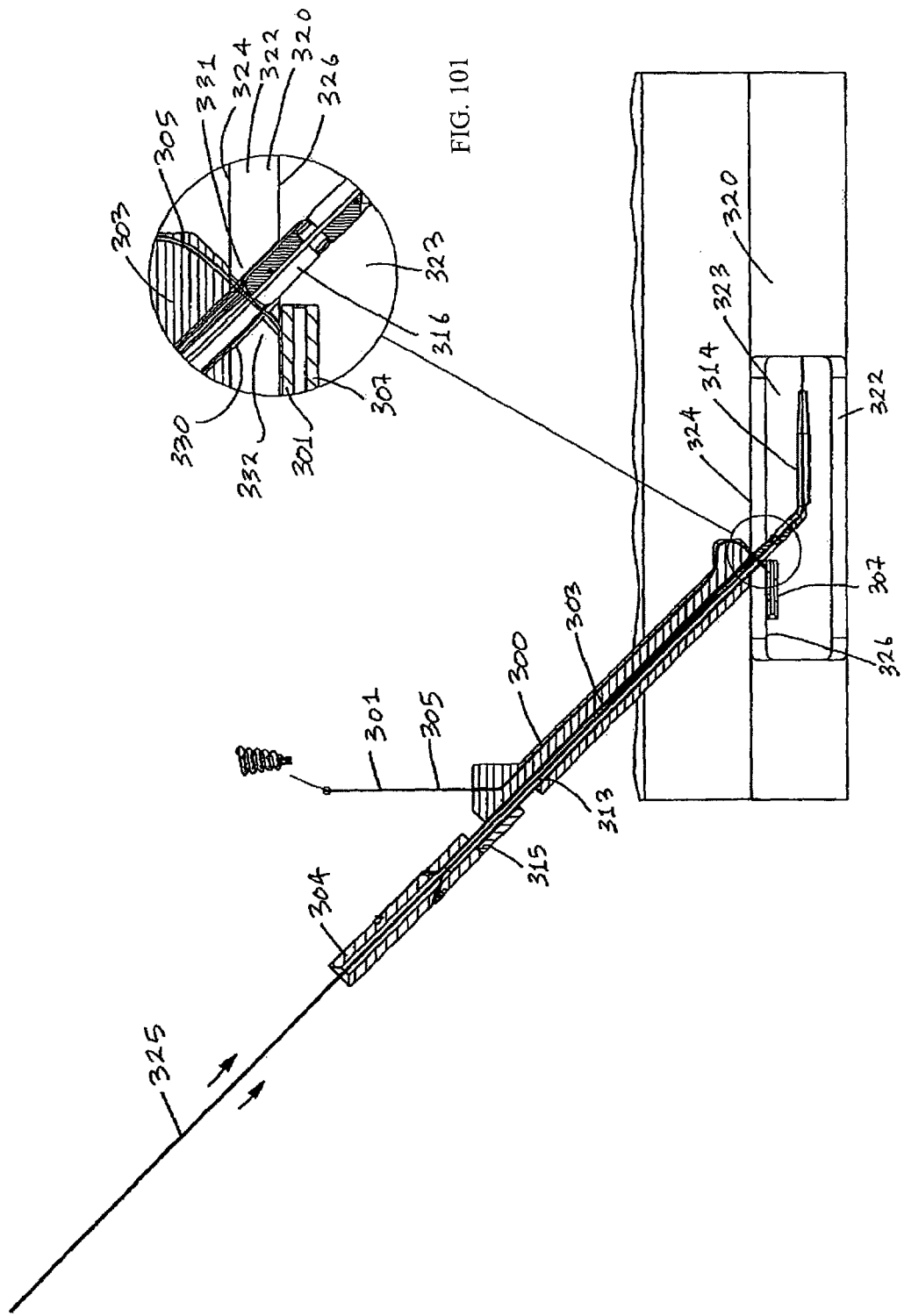

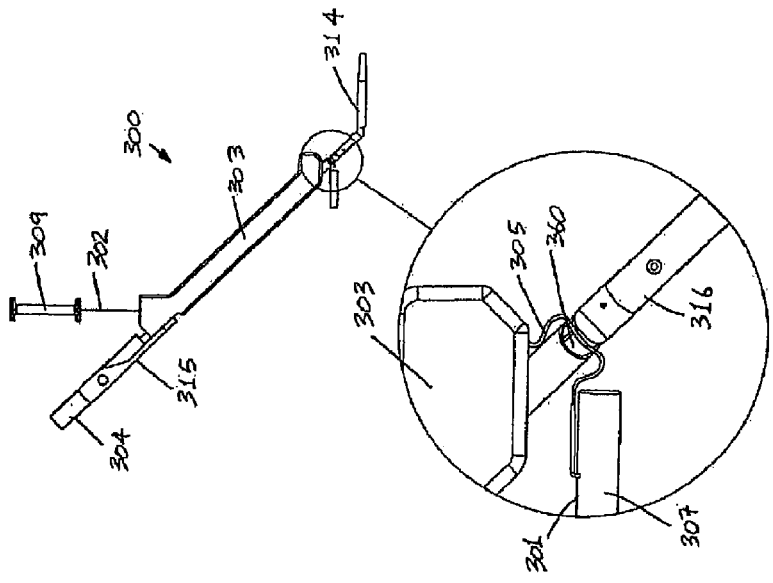
FIG. 102
FIG. 103
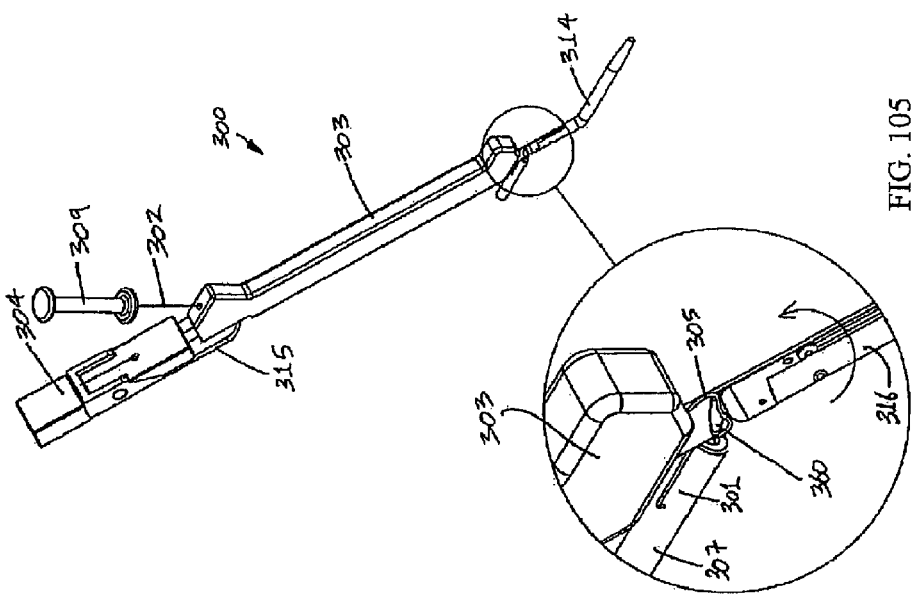
FIG. 104
FIG. 105

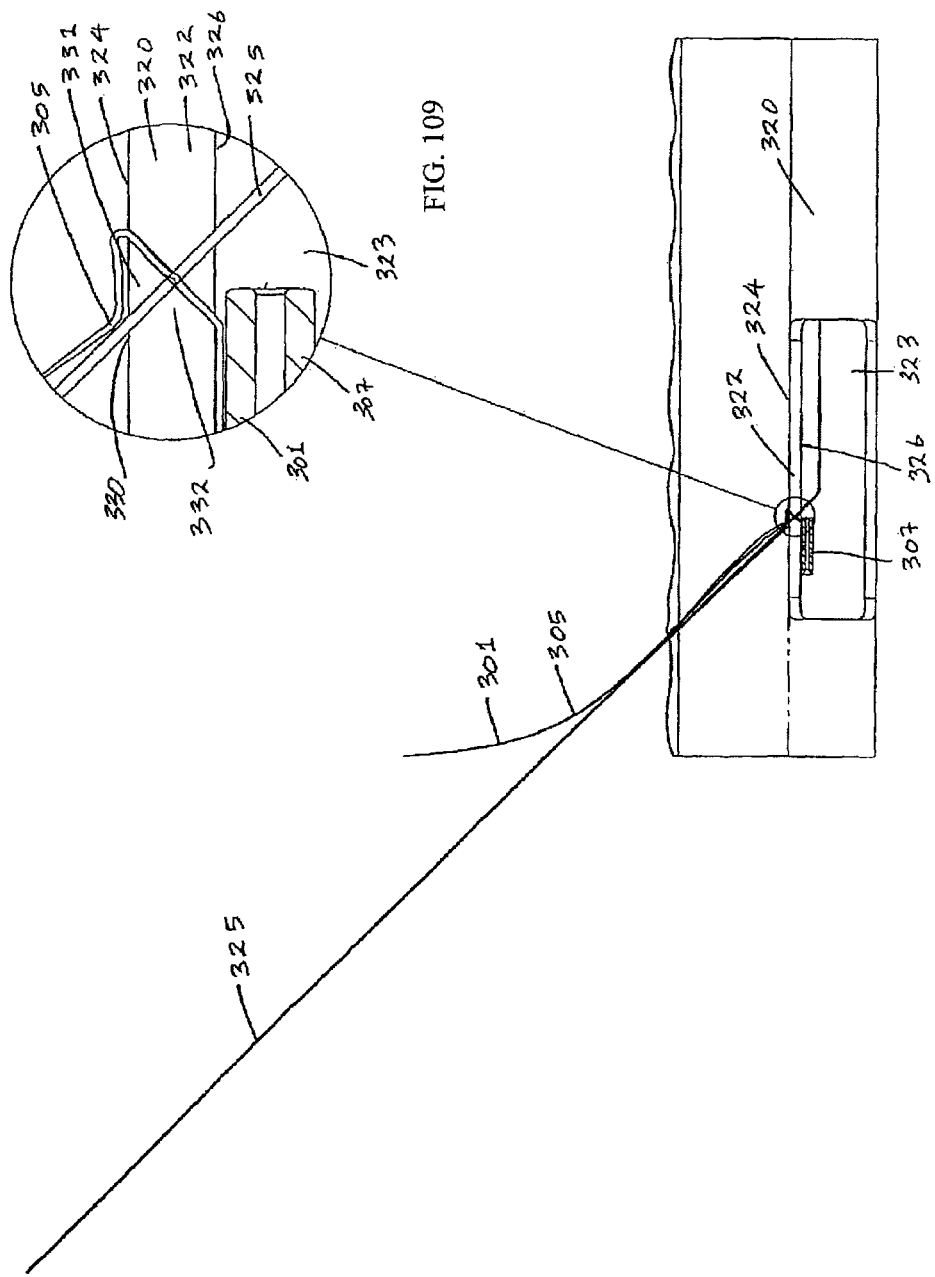

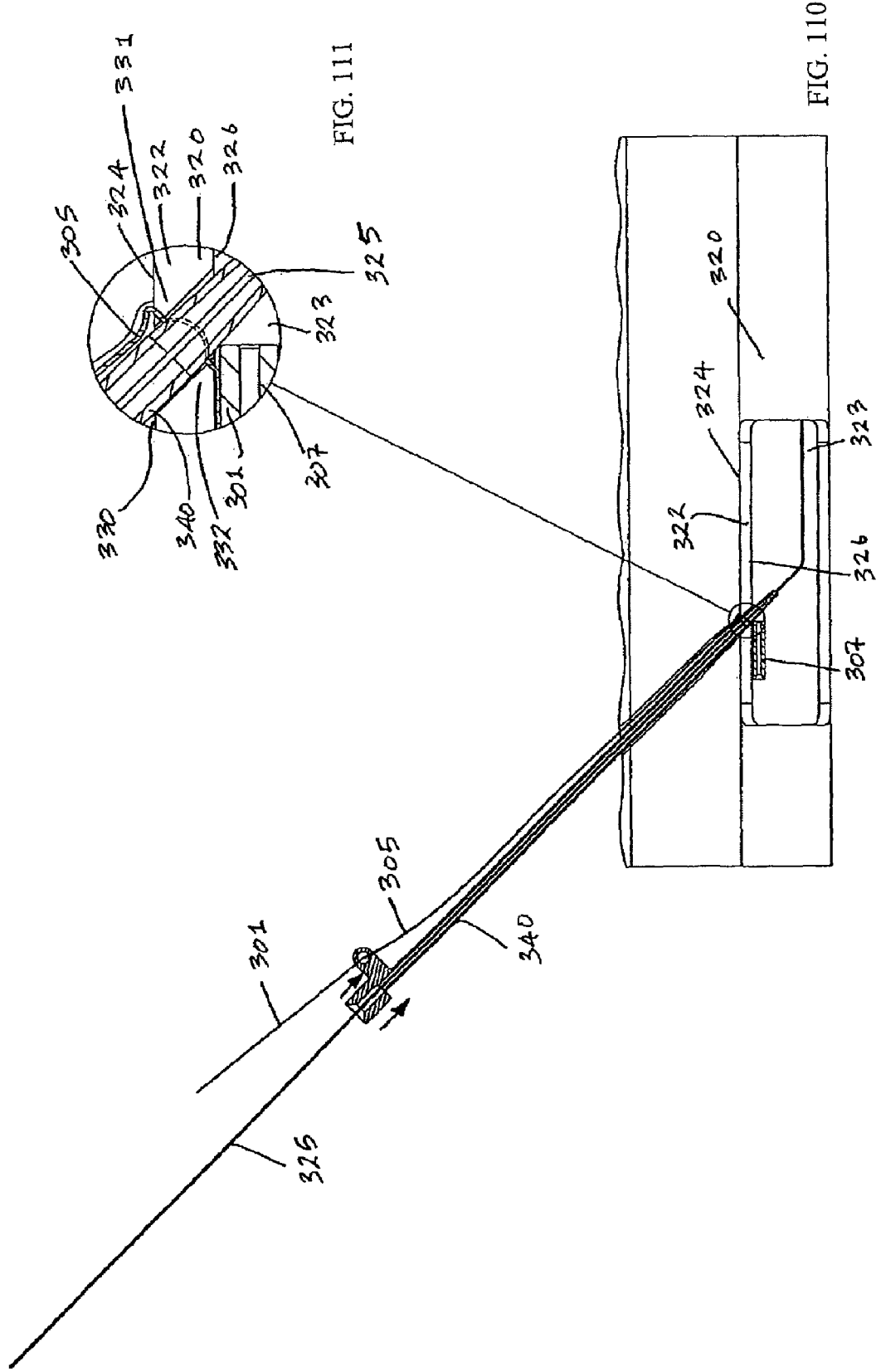

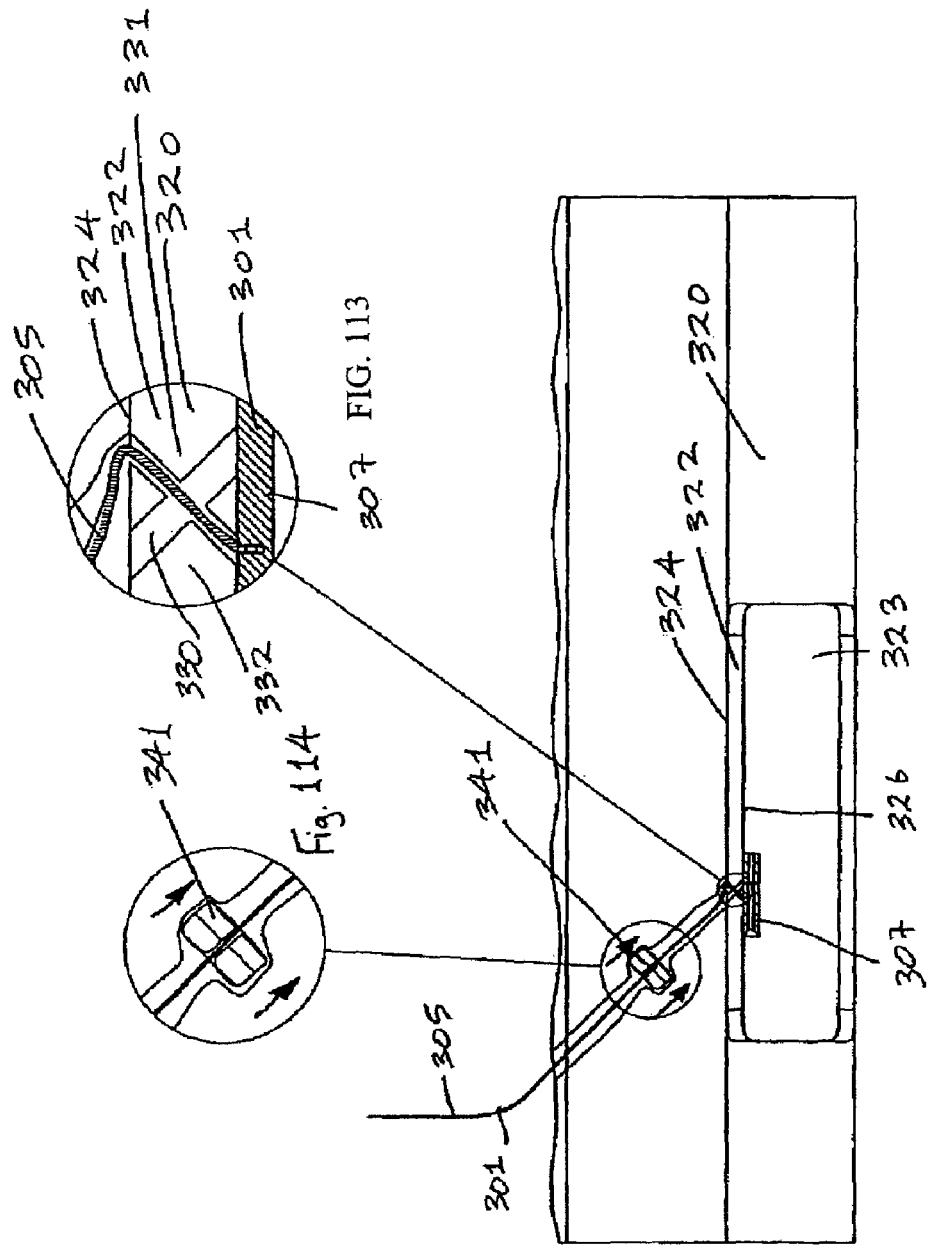

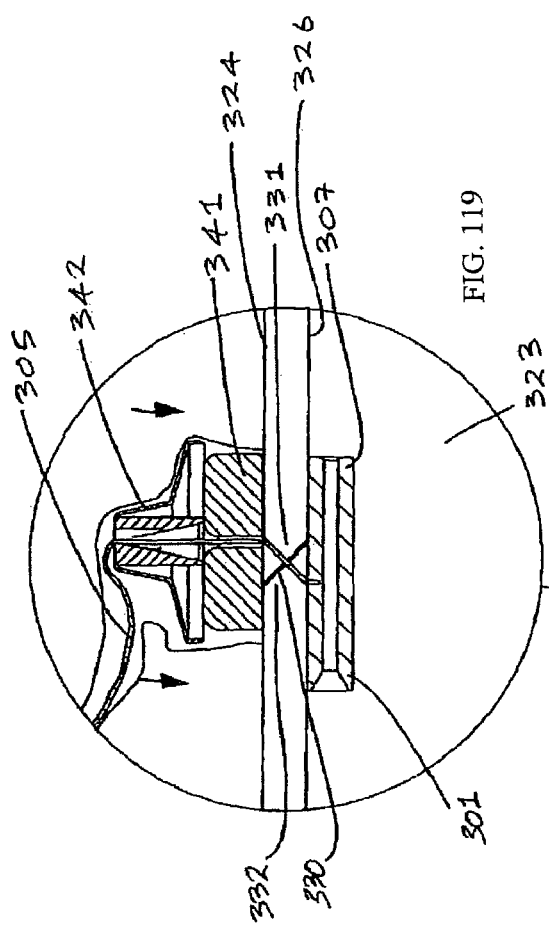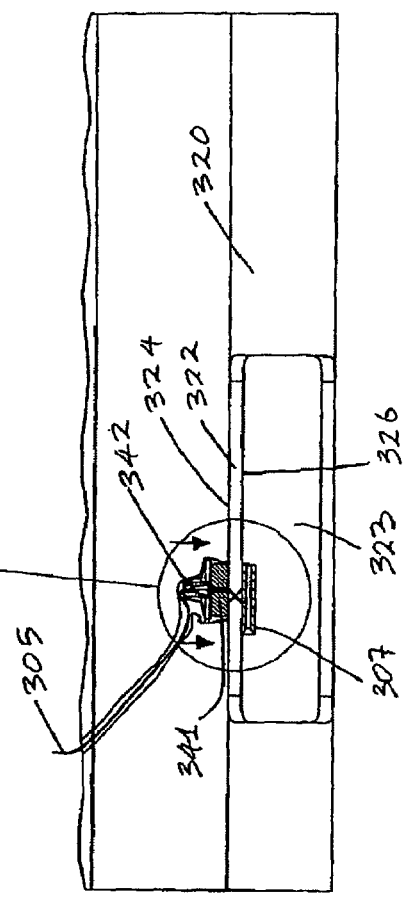
FIG. 119
FIG. 118

INTERVENTIONAL MEDICAL CLOSURE DEVICE

RELATED APPLICATION

This application claims the benefit of U.S. Provisional Patent Application Ser. No. 60/676,279, filed Apr. 29, 2005, the entire content of which are incorporated herein by reference.

FIELD OF INVENTION

This invention relates to an interventional medical closure device, and to a method of performing an interventional procedure. This invention also relates to a medical device suitable for use in accessing an interior of a body part, and to a method of accessing an interior of a body part. In one embodiment this invention relates to a vessel access and closure device for making and closing access sites in human and animal tissue, and to a related method. A particular example of the invention is a vascular lumen access and closure. In further detail, this invention generally relates, in one example, to the field of minimally invasive vascular catheterisation, and more specifically to vascular vessel access and closure methods and devices which are used to access and close the vessel openings created to perform intravascular procedures.

BACKGROUND

With recent advances in medical device technology, there has been a growth in the use of minimally invasive surgical techniques for both diagnostic and therapeutic applications by cardiologists and radiologists. For some classes of vascular procedure, they have become the treatment of choice over conventional surgery. With a minimally invasive procedure, it is often necessary to gain access to the blood vessels in order to deliver various medical devices into the vasculature such as wires, balloon catheters and other medical devices in order to treat a disease.

A commonly used procedure with which to gain access to the vascular system for minimally invasive surgery is known as the Seldinger technique. This technique involves using a small gauge hollow needle to puncture the skin and to enter the desired blood vessel. Then, a small guidewire is introduced through the lumen of the needle into the blood vessel and the needle is removed, leaving the wire in place. An introducer sheath with dilator is inserted over the guidewire and pushed through the puncture into the vessel, opening a hole in the vessel wall by forcing the sides of the puncture laterally apart to accommodate the introducer sheath in the opening. The dilator is removed and the introducer sheath, which usually contains a haemostasis valve to stop bleedback from the blood vessel, is left in place. This provides the access port for delivery of diagnostic and therapeutic catheters and medical devices to the vasculature.

Examples of minimally invasive surgery procedures include angiography, balloon angioplasty and stenting, intravascular imaging and thrombectomy. At the conclusion of the interventional procedure, the medical devices used are removed from the body including the catheters, guidewires and introducer sheaths, and it is necessary to close the puncture in the vessel created at the beginning of the procedure. This is done in order to provide haemostasis and to promote healing of the vessel wall and tissue tract.

One treatment to provide haemostasis at the puncture site post procedure is by applying external manual compression for a period of time to the patient at the site of the puncture. The duration and force required depends on the size and location of the puncture, the patient's anatomy, and the amount of anticoagulation treatment administered to the patient. The time required for the manual compression may be long and this may lead to considerable patient discomfort and extend the time to ambulation and the duration of stay in the hospital. This may increase hospital staff time and the cost of health care for the patient. Often supplemental external compression such as sandbags, body clamps and pneumatic devices are used to promote haemostasis in the vessel wall and tissue tract.

Complications may arise with compressive techniques, as too much pressure may restrict or occlude the blood vessel, potentially leading to ischemia and thrombus formation in the vessel. These techniques can have unpredictable post procedural haemorrhaging requiring additional interventions by the doctors and nurses.

Another known treatment is to employ a wound closure device to facilitate the repair of wounds caused by minimally invasive surgical access of the vasculature of the body. A variety of vascular sealing devices have been developed such as: closure devices which include suture mediated, collagen/gel based and staple devices; and assisted compression devices which include mechanical and pressure-assisted compression devices and topical patches.

However these vascular sealing devices suffer from a number of disadvantages, such as:

It may be necessary to repair a puncture site without having any control on the positioning in the vessel, the size or the shape of the puncture;

These devices may lead to puckering of the vessel wall after deployment, leading to the risk of thrombosis and vessel lumen narrowing;

These devices may leave a permanent implant in the closure site on the vessel wall;

Considerable patient discomfort may be caused during the deployment of the devices;

These devices may require additional dilation of the wound post procedure in order to accommodate the size of a staple/ clip delivery system;

It may be difficult to effect good closure if the device is poorly placed and it restricts access options for repairs;

The sealing element may be deployed inside the vessel thereby restricting or occluding blood flow;

The sealing material may contain thrombogenic material which may form thrombus at the vessel puncture and lead to emboli;

There is a risk of embolisation of the gel or foam material in the blood stream due to inaccurate deployment or migration post delivery to the tissue tract;

Ineffective closure of the puncture wound in the blood vessel may occur as the material is deployed in the tissue tract with an increased risk of haemotoma;

These devices are often designed to leave materials on the inside of the blood vessel, thereby increasing the risk of blood flow restriction or occlusion;

A disk may detach from an anchor element and travel distal to the wound site and cause blood flow restrictions or occlusions, potentially requiring surgical intervention;

There is a risk of haematoma forming in the tissue tract;

There is a risk of haemorrhage due to continued patency of the puncture in the vessel wall;

These devices may require significant manual compression before and during use.

This invention is therefore aimed at providing an improved medical device and method which will address at least some of the disadvantages encountered in conventional treatments.

SUMMARY OF INVENTION

According to the invention there is provided a method of performing an interventional procedure, the method comprising the steps of:
- creating an opening through a tissue wall, the opening extending from an external surface of the tissue to an internal lumen of the tissue;
- grasping a closure element within the lumen; and
- moving the closure element through a first part of the tissue wall on a first side of the opening, across the opening, and through a second part of the tissue wall on a second side of the opening to assist in closure of the opening.

By grasping the closure element within the lumen, this arrangement allows for a smaller profile grasping element to be used. In particular it is not necessary to deliver the closure element through a hollow needle. Practically this may allow a relatively large needle to be avoided, and makes the grasping easier to achieve. The lower profile grasping element may allow a greater variety of vessel wall thicknesses to be captured. Delivery of the lower profile grasping element may be easier due to improved track and a smaller force requirement to make the opening. This arrangement may provide greater design flexibility on the design of the closure element as it does not need to be delivered over a small wire through the tissue wall.

Retracting the closure element across the opening provides direct compression to the tissue wall at the faces of the opening which results in a lower force requirement to achieve more effective sealing of the opening. The invention minimises the force required which may minimise the pain experienced by the patient. In particular the invention does not rely on a bunching effect by 'puckering' the sides of the opening to provide sealing.

In one embodiment of the invention the method comprises the step of passing a grasping element through the tissue wall to grasp the closure element within the lumen. The grasping element may be passed across the opening. The grasping element may be passed through the second part of the tissue wall on the second side of the opening, across the opening, and through the first part on the first side of the opening.

In one case the longitudinal axis of the opening subtends an acute angle with the longitudinal axis of the lumen. The longitudinal axis of the opening may subtend an angle of approximately 45° with the longitudinal axis of the lumen. The axis along which the closure element is moved may subtend an acute angle with the longitudinal axis of the lumen. The axis along which the closure element is moved may subtend an angle in the range of from 5° to 65° with the longitudinal axis of the lumen. The axis along which the closure element is moved may subtend an angle in the range of from 15° to 55° with the longitudinal axis of the lumen. The axis along which the closure element is moved may subtend an angle of approximately 30° with the longitudinal axis of the lumen.

In another case the longitudinal axis of the opening intersects the external surface of the tissue at a first intersection point, the axis along which the closure element is moved intersects the external surface of the tissue at a second intersection point, the longitudinal axis of the opening intersects the axis along which the closure element is moved at a third intersection point, and a transverse axis of the lumen extends perpendicular to the longitudinal axis of the lumen through the third intersection point, the first intersection point and the second intersection point being on opposite sides of the transverse axis.

The axis along which the closure element is moved may subtend an angle in the range of from 70° to 130° with the longitudinal axis of the opening. The axis along which the closure element is moved may subtend an angle in the range of from 80° to 120° with the longitudinal axis of the opening. The axis along which the closure element is moved may subtend an angle of approximately 105° with the longitudinal axis of the opening.

In one embodiment the opening comprises a puncture opening. The method may comprise the step of dilating the opening. The method may comprise the step of inserting the closure element into the lumen. The closure element may be inserted through the opening into the lumen.

In one case the method comprises the step of maintaining the position of the closure element substantially fixed within the lumen prior to grasping. By maintaining the position of the closure element substantially fixed, this arrangement provides for an easier and more reliable means for grasping the closure element. The method may comprise the step of passing one or more medical devices through the opening into the lumen to perform at least one interventional procedure within the lumen.

In another case the closure element is moved to engage an internal surface of the tissue. The closure element may engage the internal surface of the tissue on the first side of the opening and on the second side of the opening. The method may comprise the step of engaging the external surface of the tissue. The external surface of the tissue may be engaged on the first side of the opening and on the second side of the opening. The method may comprise the step of applying a compressive force to the external surface of the tissue and/or to the internal surface of the tissue. The compressive force may be applied on the first side of the opening and on the second side of the opening.

In a further aspect of the invention there is provided a method of performing an interventional procedure, the method comprising the steps of:
- creating an opening through a tissue wall;
- moving a closure element through a first part of the tissue wall on a first side of the opening, across the opening, and through a second part of the tissue wall on a second side of the opening to assist in closure of the opening.

In one embodiment the longitudinal axis of the opening intersects an external surface of the tissue at a first intersection point, the axis along which the closure element is moved intersects the external surface of the tissue at a second intersection point, the longitudinal axis of the opening intersects the axis along which the closure element is moved at a third intersection point, and a transverse axis of the lumen extends perpendicular to the longitudinal axis of the lumen through the third intersection point, the first intersection point and the second intersection point being on opposite sides of the transverse axis.

The invention also provides in another aspect an interventional medical closure device comprising:
- a closure element; and
- a grasping element for grasping the closure element whtin an internal lumen of a tissue;
- the grasping element being configured to move the closure element through a first part of the tissue wall on a first side of an opening through the tissue wall, across the opening, and through a second part of the tissue wall on a second side of the opening to assist in closure of the opening.

In one embodiment of the invention the grasping element is engageable with the closure element to grasp the closure element. The grasping element may be engageable with the closure element in a snap-fit manner. A distal end of the grasping element may be engageable with a proximal end of the closure element. The device may comprise a guide element for guiding passage of the grasping element. The guide element may be configured to guide passage of the grasping element across an opening through a tissue wall. The guide element may be configured to guide passage of the grasping element through a second part of a tissue wall on a second side of an opening through the tissue wall, across the opening, and through a first part of the tissue wall on a first side of the opening. The guide element may comprise an outlet part out of which the grasping element may pass. The outlet part may be movable relative to a main body portion of the guide element. The outlet part may be movable between a delivery configuration and a guiding configuration.

In one case the device comprises an introducer sheath to dilate an opening through a tissue wall.

In another embodiment the device comprises a delivery element to deliver the closure element into an internal lumen of a tissue. The delivery element may be engageable with an internal surface of a tissue to maintain the position of the closure element substantially fixed within an internal lumen of the tissue prior to grasping. The delivery element may comprise an engagement element for engagement with an internal surface of a tissue. The engagement element may be movable relative to a main body portion of the delivery element. The engagement element may be movable between a delivery configuration and an engagement configuration.

In one case the closure element is engageable with an internal surface of a tissue. The closure element may comprise an engagement element for engagement with an internal surface of a tissue. The device may comprise an external engagement element for engagement with an external surface of a tissue.

According to the invention there is provided a method of accessing an interior of a body part, the method comprising the steps of:
  creating an incision in a wall of the body part with at least one flap of tissue wall at a side of the incision;
  moving the flap aside to form an opening to the interior of the body part; and
  inserting at least one medical device through the opening to access the interior of the body part.

The opening to the interior of the body part is created by moving the flap aside. In the invention, it is therefore not necessary to force the sides of a puncture laterally apart to form an opening to the interior of the body part. The invention therefore reduces the trauma caused upon creation of the opening to the interior of the body part.

In addition, less difficulties arise when attempting to close over and seal the opening after completion of a medical procedure within the interior of the body part. In particular the flap may be moved back to seal across the opening, and thus provides a convenient means of sealing the opening. The invention therefore provides a simple yet effective means of avoiding the disadvantages encountered using conventional treatments.

In one embodiment the longitudinal axis of the incision is inclined relative to the plane of the wall of the body part. The flap may be created by means of inclining the longitudinal axis of the incision.

In another embodiment the angle subtended between the longitudinal axis of the incision and the plane of the wall of the body part is in the range of from 10° to 80°.

In a further embodiment the angle subtended between the longitudinal axis of the incision and the plane of the wall of the body part is approximately 45°.

In one embodiment the method comprises the step of engaging the flap to move the flap aside to form the opening.

In another embodiment the flap is pushed distally to form the opening.

In a further embodiment the flap is engaged by an introducer sheath, and/or a delivery catheter, and/or a guide catheter.

In one embodiment the method comprises the step of performing a medical procedure using the medical device.

In another embodiment the method comprises the step of withdrawing the medical device from the interior of the body part.

In a further embodiment the method comprises the step of sealing across the opening.

In one embodiment the flap is moved back to seal across the opening. The flap effectively acts as a gate and may be moved aside to reveal the opening. Subsequent to completion of a medical procedure performed within the interior of the body part, the flap may be moved back to seal across the opening.

In another embodiment the method comprises the step of engaging the flap to move the flap back to seal across the opening. The positive engagement of the flap ensures that the opening is quickly and effectively sealed to minimise blood loss.

In a further embodiment the flap is pulled proximally to seal across the opening.

In one embodiment the flap is engaged by a part of an engagement element.

In another embodiment the method comprises the step of moving the part of the engagement element from a delivery configuration to a deployed configuration before engaging the flap. In the delivery configuration, the engagement element has a relatively low profile for passing through the flap/wall of the body part, and for subsequent withdrawal from the flap/wall of the body part. In the deployed configuration, the engagement element may be engaged with the flap to control movement of the flap.

In a further embodiment the part of engagement element is expanded from the delivery configuration to the deployed configuration.

In one embodiment the part of the engagement element is inflated from the delivery configuration to the deployed configuration.

In another embodiment the method comprises the step of moving the part of the engagement element from the deployed configuration to the delivery configuration after sealing across the opening.

In a further embodiment the part of the engagement element is contracted from the deployed configuration to the delivery configuration.

In one embodiment the part of the engagement element is deflated from the deployed configuration to the delivery configuration.

In another embodiment the method comprises the step of piercing the engagement element through the flap.

In a further embodiment the method comprises the step of piercing the engagement element through the wall of the body part at the opposite side of the incision. By piercing the engagement element through both the flap and the opposite wall of the body part, the flap may be drawn into contact with the wall in the manner of a suture to seal across the opening.

In one embodiment the engagement element is pierced through the flap and/or through the wall of the body part by piercing the flap and/or the wall of the body part with a needle and passing the engagement element through the needle.

In another embodiment the method comprises the step of removing the needle from the flap and/or from the wall of the body part to leave the engagement element pierced therethrough.

In a further embodiment the engagement element is pierced through the flap and/or through the wall of the body part before the incision is created.

In one embodiment the incision is created around the engagement element pierced through the flap and/or through the wall of the body part.

In another embodiment the method comprises the step of protecting the engagement element during the step of creating the incision. Protecting the engagement element ensures that the engagement element is not inadvertently damaged during creation of the incision. Protecting the engagement element with a protective sheath deployed over the trapping element prior to activating the vessel wall cutting mechanism, ensures that the engagement element is not inadvertently damaged during creation of the incision.

In a further embodiment the method comprises the step of withdrawing the engagement element from the flap after sealing across the opening.

In one embodiment the method comprises the step of withdrawing the engagement element from the wall of the body part at the opposite side of the incision after sealing across the opening.

In another embodiment the flap moves between a sealing configuration, in which the flap seals across the opening, and an access configuration, in which the flap is moved aside to reveal the opening.

In a further embodiment the flap moves relative to the wall of the body part.

In one embodiment the flap moves in a substantially hinging manner.

In another embodiment the axis of hinging is substantially parallel to the plane of the wall of the body part.

In a further embodiment in the access configuration, the flap is located substantially within the interior of the body part.

In one embodiment in the sealing configuration, the flap engages the wall of the body part at the opposite side of the incision.

In another embodiment the flap is anchored in the sealing configuration.

In a further embodiment the medical device comprises a guidewire, and/or an introducer sheath, and/or a delivery catheter, and/or a guide catheter.

In one embodiment the body part comprises a blood vessel.

In another embodiment the incision is substantially arch-shaped in profile.

According to another aspect of the invention there is provided a medical device comprising an incising element for creating an incision in a wall of a body part with at least one flap of tissue wall at a side of the incision.

In one embodiment the incising element is configured to create an incision with the longitudinal axis of the incision inclined relative to the plane of a wall of a body part.

In another embodiment the incising element is configured to create an incision in a wall of a body part, the wall having a medical element pierced through the wall.

In a further embodiment the incising element is configured to create the incision around the medical element pierced through the wall of the body part.

In one embodiment the incising element is movable between an open configuration and a closed configuration to create the incision around the medical element.

In another embodiment in the closed configuration, the incising element has an opening for receiving the medical element therethrough. The opening through the incising element ensures that the incision is created around the medical element without inadvertently causing damage to the medical element.

In a further embodiment the incising element is configured to create an incision having an arch-shape in profile.

In one embodiment the incising element has a cutting part movable between a first configuration and a second configuration.

In another embodiment the cutting part is biased towards the second configuration.

In a further embodiment the incising device has a restraining part to restrain the cutting part in the first configuration.

In one embodiment the cutting part is movable relative to the restraining part to release the cutting part to move to the second configuration.

In another embodiment the restraining part comprises an outer sheath.

In a further embodiment the first configuration is a contracted configuration.

In one embodiment in the first configuration, the cutting part is substantially tubular.

In another embodiment the second configuration is an expanded configuration.

In a further embodiment in the second configuration, the cutting part is at least partially substantially frusto-conical.

In one embodiment the cutting part is substantially frusto-conical around only part of the circumference of the part.

In another embodiment the cutting part has a recess around part of the circumference of the part.

In a further embodiment the device comprises an engagement element, a part of the engagement element being engagable with a flap of tissue wall at a side of an incision to move the flap to seal across the opening through the incision.

According to a further aspect the invention provides a medical device comprising an engagement element, a part of the engagement element being engagable with a flap of tissue wall at a side of an incision to move the flap to seal across an opening through the incision.

In one embodiment the part of the engagement element is movable between a delivery configuration and a deployed configuration.

In another embodiment the part of the engagement element is expandable/contractible between the delivery configuration and the deployed configuration.

In a further embodiment the part of the engagement element is inflatable/deflatable between the delivery configuration and the deployed configuration.

In one embodiment the part of the engagement element is biodegradable.

In another embodiment the device comprises one or more protective elements for protecting at least part of the engagement element during creation of an incision.

In a further embodiment the protective element is configured to cover at least part of the engagement element.

In one embodiment the protective element comprises a protective sheath extendable over the engagement element.

In another embodiment the protective element is movable relative to the engagement element between a protecting configuration, in which the protective element covers at least part of the engagement element, and an uncovered configuration.

In a further embodiment the engagement element is piercable through a flap of tissue wall.

In one embodiment the engagement element is substantially elongate.

In another embodiment the device comprises an anchor to anchor the flap sealed across the opening.

In a further embodiment the engagement element carries the anchor.

In one embodiment the anchor is configured to be located on an external surface of the flap.

In one aspect the invention provides a method and a device for accessing the vascular system through a controlled incision of a vessel wall, and then closing and sealing the vessel wall incision to provide haemostasis and promote healing of the access site.

The invention is applicable in vascular access procedures as well as in other percutaneous procedures requiring access to hollow internal organs in the body.

The invention enjoys a number of advantages over conventional treatments.

To gain access to the vasculature, the invention creates a controlled surgical incision at the vessel wall. This is in contrast with the conventional practice of forcing a blunt dilator through the vessel wall, which may cause trauma and possible tearing, and which may make subsequent closure a more difficult process.

During the vessel entry procedure, a trapping element may be deployed in the vessel to secure both leaves of the incision. This effectively, at the beginning of the procedure, provides the mechanism for subsequently closing the vessel wall opening at the end of the procedure, without having to use another closure device. This contrasts with conventional devices which address the problem of the puncture wound, created by the blunt introducer/dilator combination, at the end of the procedure.

The invention is designed to provide a positive closure mechanism, whereby the leaves of the access incision are individually secured by a trapping element.

The invention may have a trapping element, which may be in one embodiment, removable after sealing of the puncture.

The invention may have a trapping element, which may be in one embodiment, biodegradable/bioresorbable after sealing of the puncture.

BRIEF DESCRIPTION OF THE DRAWINGS

The invention will be more clearly understood from the following description of some embodiments thereof, given by way of example only, with reference to the accompanying drawings, in which:

FIGS. 5(a) to 5(d) are partially cross-sectional, side views illustrating introduction of the engagement element of FIG. 1 into an interior of a body part;

FIGS. 10 to 12 are views similar to FIGS. 6 to 8 of the engagement element and the incising element of FIG. 6, in use at a second step of the method.

FIGS. 13 to 16 are views similar to FIGS. 6 to 9 of the engagement element and the incising element of FIG. 6, in use at a third step of the method;

FIGS. 17 to 20 are views similar to FIGS. 6 to 9 of the engagement element and the incising element of FIG. 6, in use at a fourth step of the method;

FIGS. 21 to 23 are views similar to FIGS. 6 to 8 of the engagement element and the incising element of FIG. 6, in use at a fifth step of the method;

FIGS. 24 to 27 are views similar to FIGS. 6 to 9 of the engagement element of FIG. 6, in use at a sixth step of the method;

FIGS. 35 and 35(a) are partially cross-sectional, side views illustrating anchoring of the flap;

FIGS. 56(a) to 56(e) are perspective views of an incising element of another medical device according to the invention;

FIGS. 74 to 93 are partially cross-sectional, side views illustrating steps in a method of performing an interventional procedure according to the invention using the device of FIGS. 70 and 71;

FIGS. 96 to 101 are partially cross-sectional, side views illustrating further steps in the method of performing an interventional procedure according to the invention using the device of FIGS. 70 and 71;

FIG. 102 is a side view of the device of FIGS. 70 and 71 in the step illustrated in FIGS. 100 and 101;

FIG. 103 is an enlarged, side view of a part of the device of FIG. 102;

FIG. 104 is a perspective view of the device of FIGS. 70 and 71 in the step illustrated in FIGS. 100 and 101;

FIG. 105 is an enlarged, perspective view of a part of the device of FIG. 104;

FIGS. 106 to 121 are partially cross-sectional, side views of further steps in the method of performing an interventional procedure according to the invention using the device of FIGS. 70 and 71;

DETAILED DESCRIPTION

Figure 1:
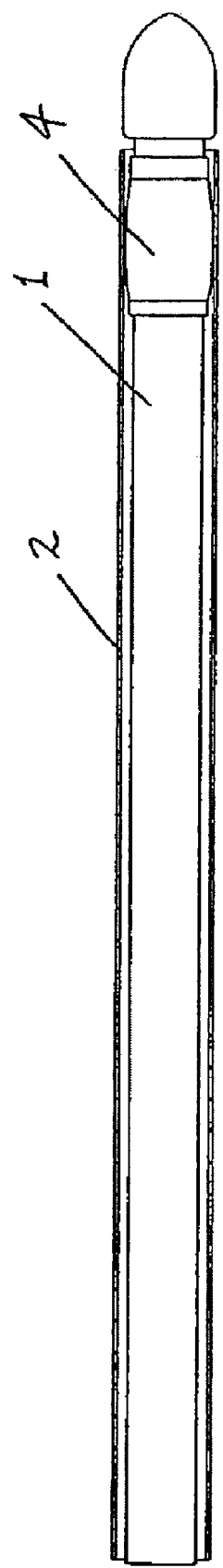
FIG. 1 is a partially cross-sectional, side view of a distal end of an engagement element of a medical device according to the invention.

Referring to the drawings and initially to FIGS. 1 to 35(a) thereof, there is illustrated a medical device according to the invention, which is suitable for use in accessing an interior of a body part. The device is particularly suitable for accessing the interior of a blood vessel 6. The medical device comprises an elongate engagement element 1, a protective sheath 2, as illustrated in FIGS. 1 to 5, and an incising element 3, as illustrated in FIGS. 6 to 9.

Figure 4:
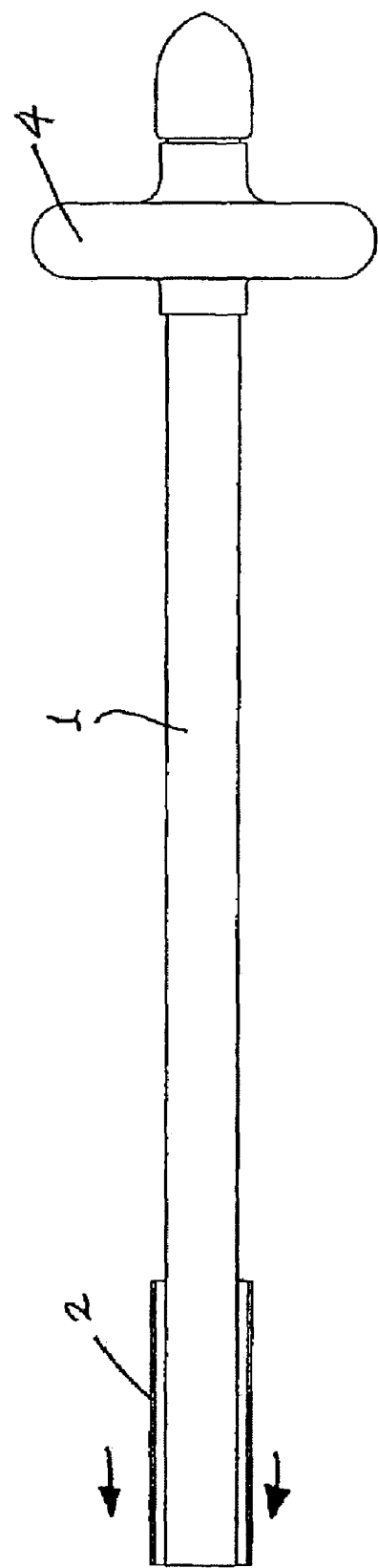
Figure 5:
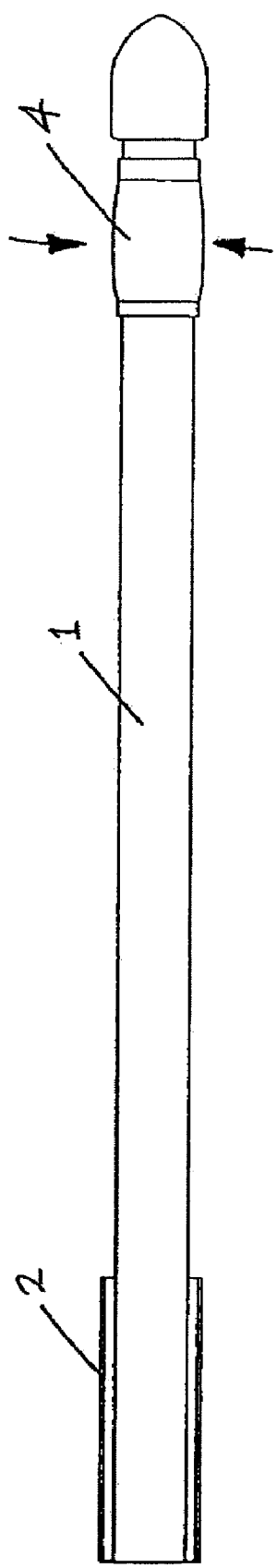
Figure 5:
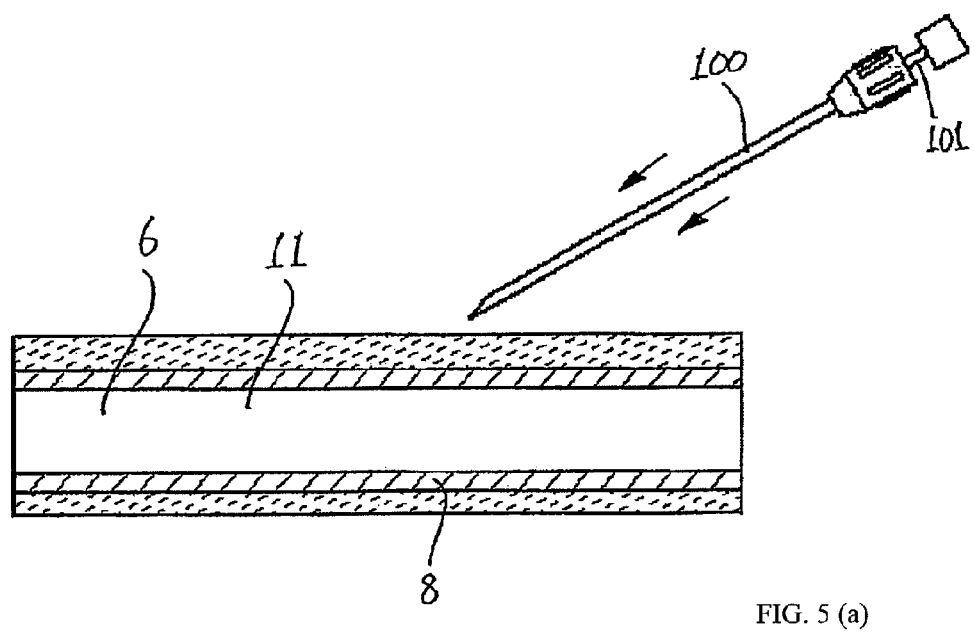
Figure 5:
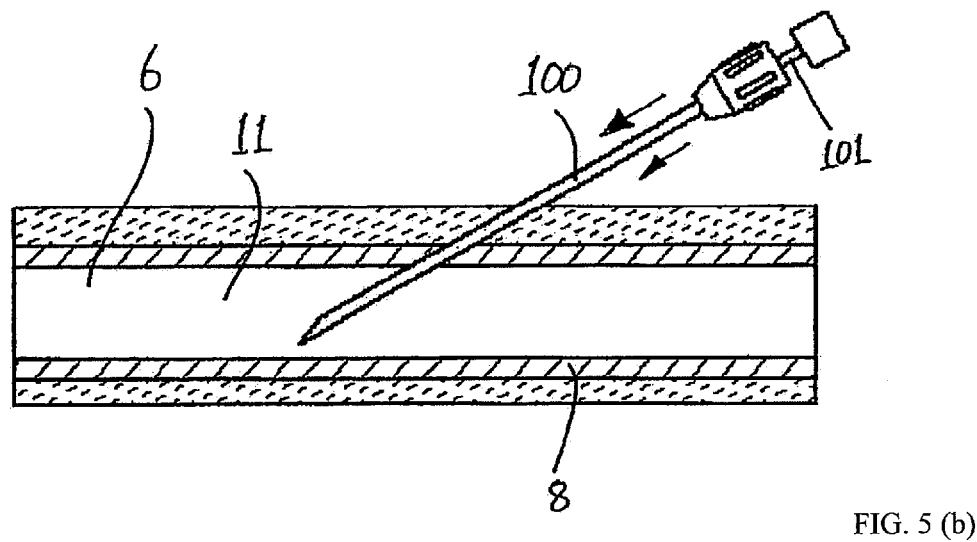
Figure 5:
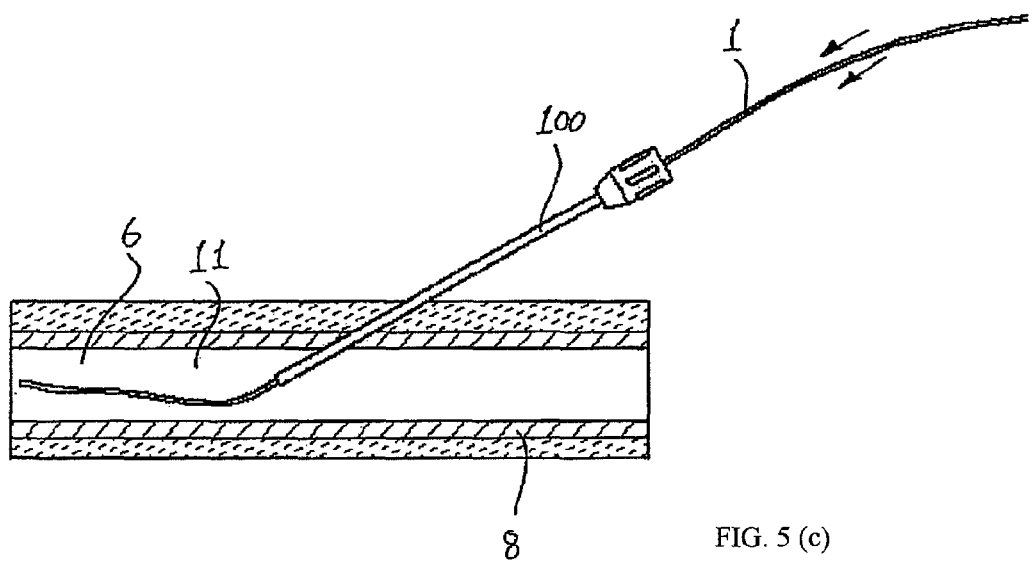
Figure 5:
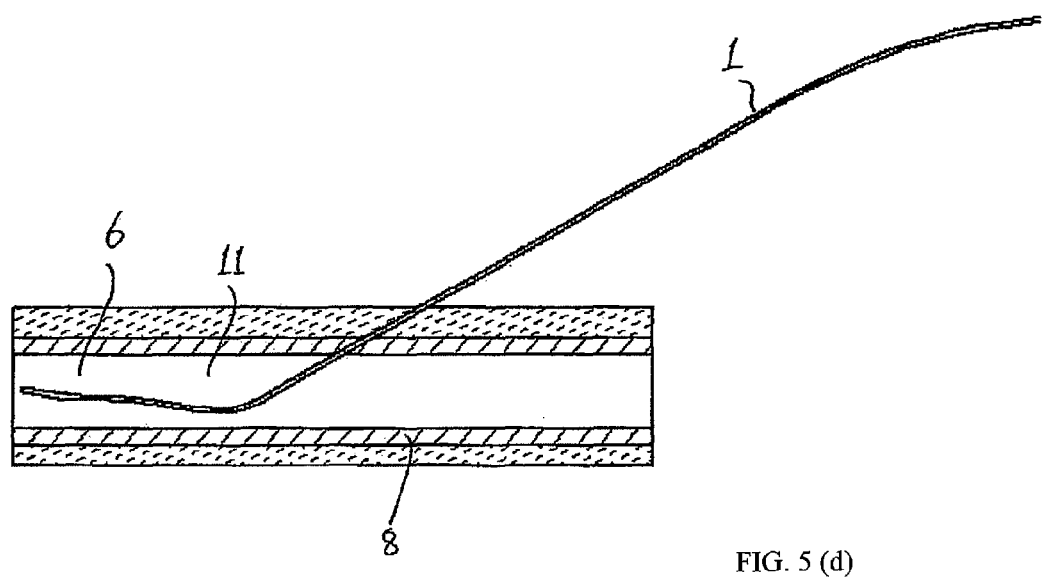
Figure 33:
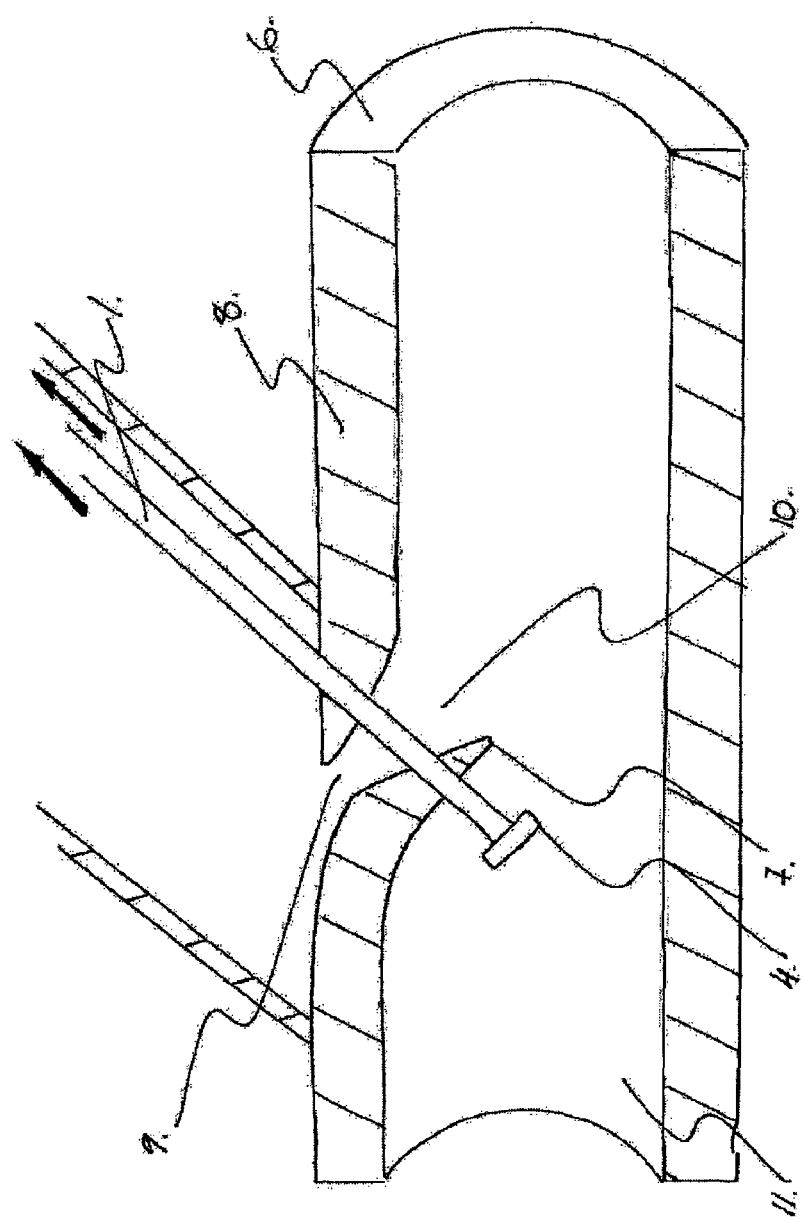
FIG. 33 is a partially cross-sectional, side view illustrating trapping of a flap using the engagement element of FIG. 6.

The engagement element 1 comprises a retaining element, which is provided in this case as a balloon part 4, which is expandable, in this case inflatable, from a low-profile delivery configuration (FIGS. 1 and 2) to a deployed configuration (FIGS. 3 and 4), and is returnable, in this case deflatable, from the deployed configuration to the delivery configuration (FIG. 5). In the delivery configuration, the engagement element 1 is pierceable through a flap 7 of tissue wall and through a wall 8 of the blood vessel 6. In the deployed configuration the retaining element part 4 is engagable with the flap 7 of tissue wall at a side of an incision 9 (FIG. 33). The engagement element 1 may thus be employed to move the flap 7 to seal across an opening 10 through the incision 9. In the delivery configuration, the engagement element 1 may be withdrawn from the flap 7 and from the wall 8 of the blood vessel 6.

Figure 2:
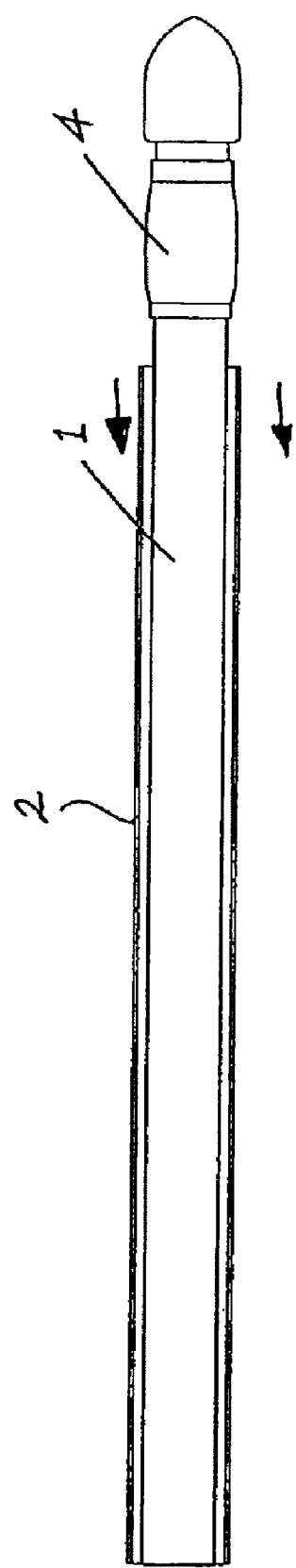
FIGS. 2 to 5 are partially cross-sectional, side views of the engagement element of FIG. 1, in use.
Figure 3:
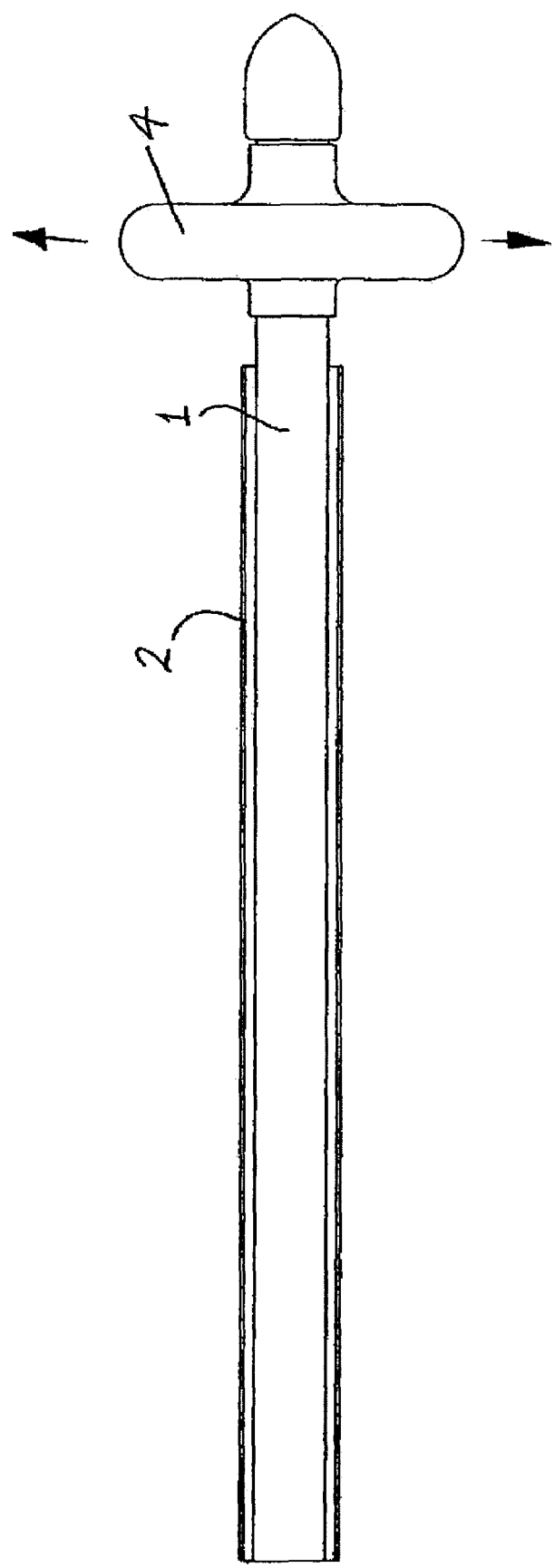

The engagement element deployment technique is illustrated in FIGS. 1 to 5: FIG. 1 illustrates the undeployed engagement element 1; FIG. 2 illustrates the sheath 2 retracted to allow deployment; FIG. 3 illustrates the retaining element 4 inflation/expansion phase; FIG. 4 illustrates the sheath 2 retracted to leave the engagement element 1 in place; and FIG. 5 illustrates the retaining element 4 deflated to allow engagement element 1 removal.

The protective sheath 2 is slidably movable relative to the engagement element 1 between a protecting configuration (FIG. 1) and an uncovered configuration (FIGS. 4 and 5). In the protecting configuration, the sheath 2 extends over the engagement element 1 and covers the retaining element part 4 to protect the engagement element 1 and the balloon part 4.

Figure 20:
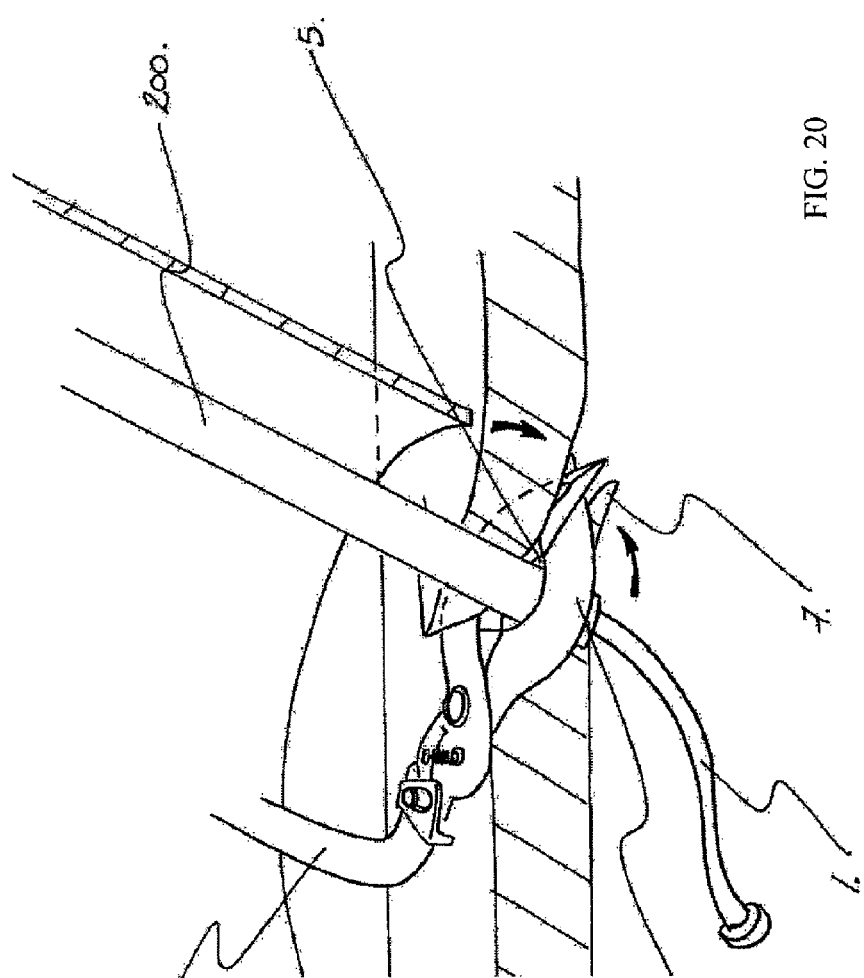

The medical device also comprises an outer sheath 200, which is extendable over the protective sheath 2 and over the engagement element 1 in a sliding co-axial manner. The outer sheath 200 is slidably movable relative to the protective sheath 2/engagement element 1 between an uncovered configuration (FIG. 9) and a protecting configuration (FIG. 20).

The sheath 200 is especially useful for protecting the engagement element 1 during creation of the incision 9 in the wall of the blood vessel 6. In the uncovered configuration, the sheath 200 is retracted.

A modified Seldinger technique is used to introduce the engagement element 1. When using devices of the invention to access vessels such as arteries 6, it is necessary to use a modified Seldinger technique in order to introduce the engagement element 1 into the interior or vessel inner lumen 11 from the skin. The starting position with the needle 100 positioned above the skin ready for incision is illustrated in FIG. 5(a). The needle 100 is used to puncture the skin and gain access to the vessel inner lumen 11 (FIG. 5(b)). With the needle 100 in place, the needle inner core 101 is removed and the engagement element 1 is introduced through the needle lumen and into the vessel 6 (FIG. 5(c)). Finally the needle 100 is withdrawn from the vessel 6 and body, and the engagement element 1 is left in place in the lumen 11 (FIG. 5(d)).

This then forms the guidance system for the delivery of the devices of the invention to the vessel wall for subsequent operations.

The incising element 3 is suitable for creating the incision 9 in the wall 8 of the blood vessel 6 through which the engagement element 1 has been pierced. In particular the incising element 3 creates the incision 9 around the engagement element 1 and the protective sheath 2 pierced through the wall 8 (FIG. 20).

Figure 8:
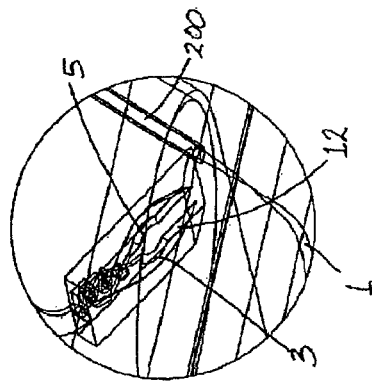
FIGS. 8 and 9 are enlarged, cut-away, perspective views of the engagement element and the incising element of FIG. 6.
Figure 9:
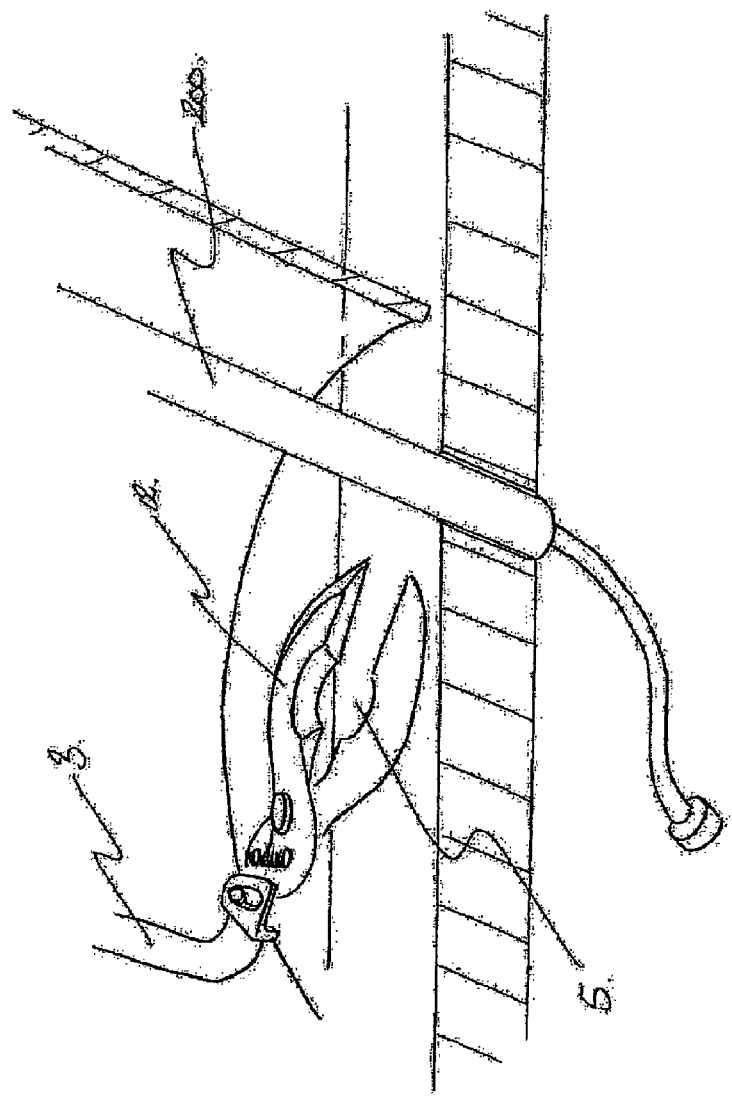
Figure 16:
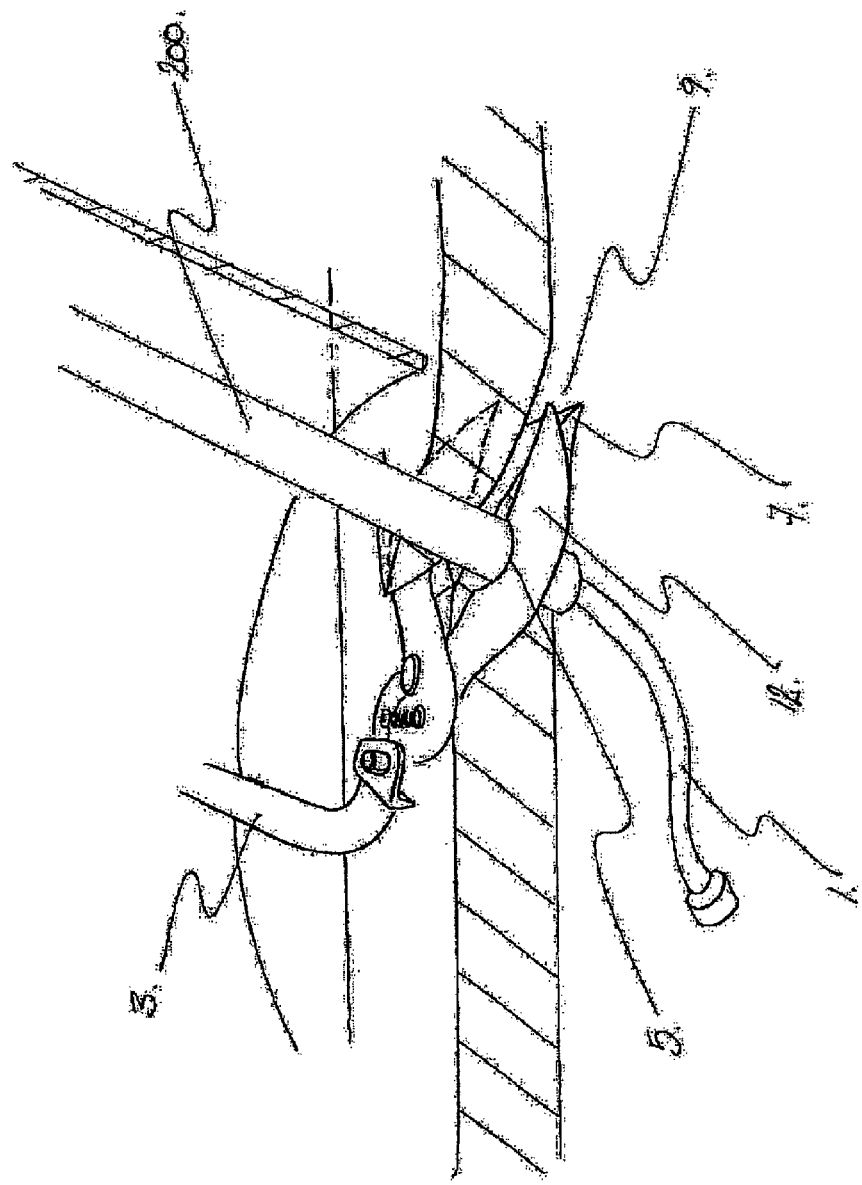

In this case, the incising element 3 is provided in the form of a scissors-like arrangement 12 (FIGS. 8 and 9). The scissors 12 is movable between an open configuration (FIG. 16) and a closed configuration (FIG. 20) to create the incision 9 in the wall 8 of the blood vessel 6 around the engagement element 1 and the outer sheath 200. In the closed configuration, the scissors 12 has an opening 5 for receiving the engagement element 1 and the outer sheath 200 extending through the incising device 3 (FIG. 20).

Figure 28:
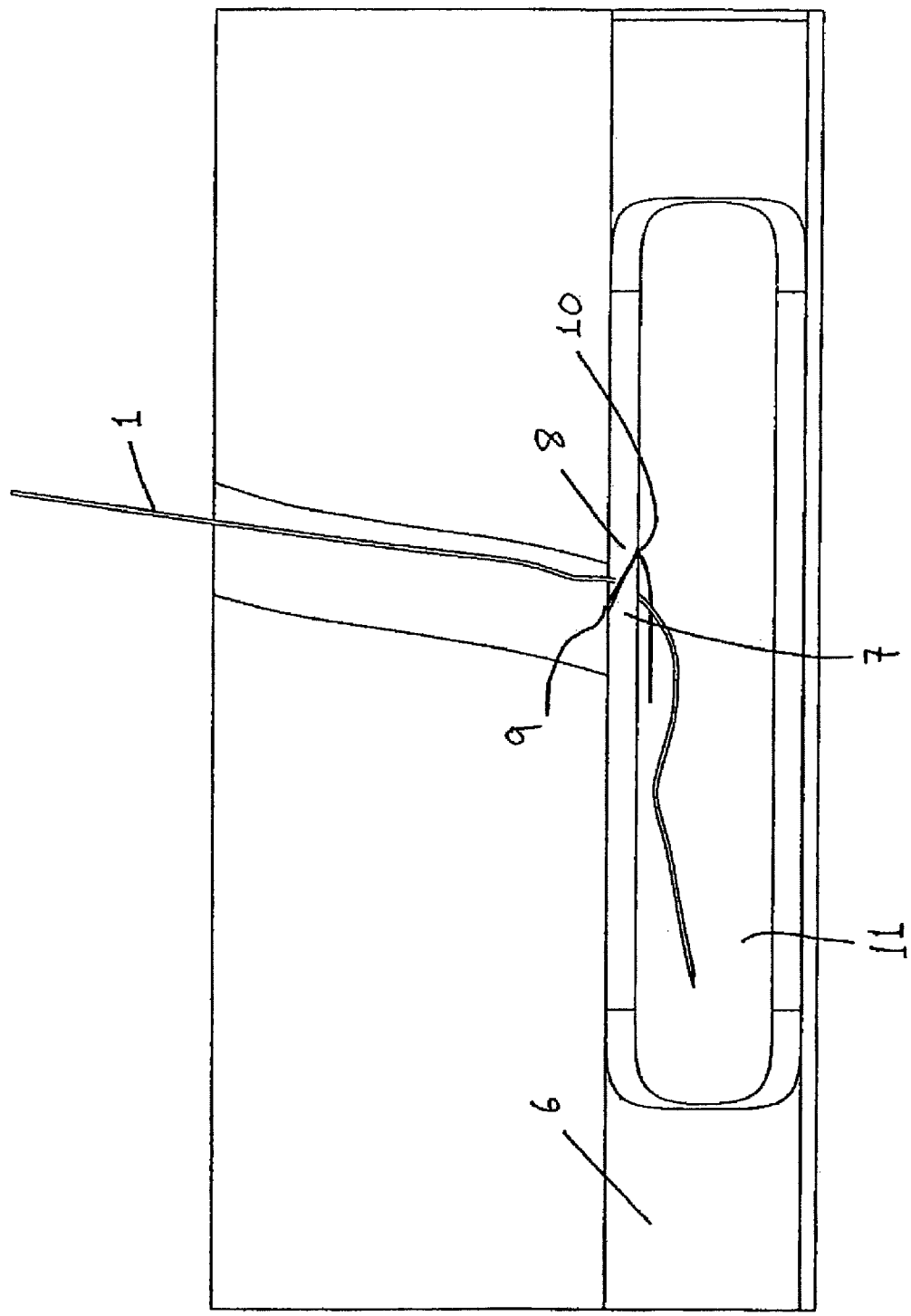
FIGS. 28 to 30 are partially cross-sectional, side views illustrating introduction of an introducer sheath and a guidewire.
Figure 28:
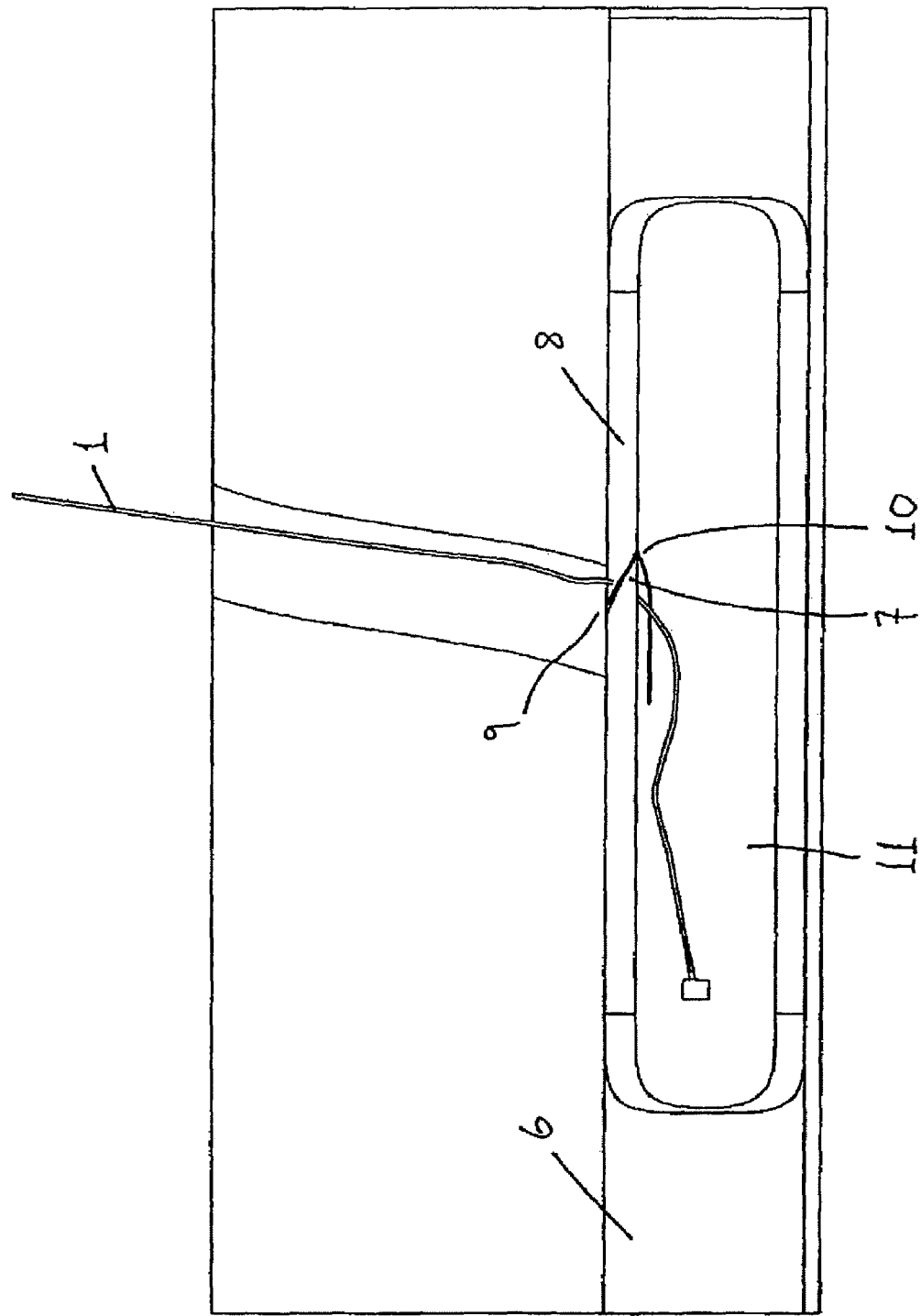

As illustrated in FIGS. 22 and 25, the incising element 3 creates the incision 9 with the longitudinal axis A-A of the incision 9 inclined relative to the plane of the wall 8 of the blood vessel 6. The inclined incision 9 ensures that the flap 7 of tissue wall is created at the side of the incision 9, as illustrated in FIGS. 25 and 28.

The longitudinal axis A-A may be inclined at an angle in the range of from 10° to 80° relative to the plane of the wall 8, and is, in one embodiment, inclined at an angle of approximately 45°.

The medical device of the invention may be employed in performing a method of accessing an interior 11 of the blood vessel 6. In use, the engagement element 1 is pierced through the wall 8 of the blood vessel 6, and the incising element 3 is positioned exterior of the blood vessel 6 with the scissors 12 inclined relative to the plane of the wall 8 of the blood vessel 6 (FIGS. 6 to 9). The outer sheath 200 is then pushed distally over the engagement element 1 to cover the retaining element part 4 (FIGS. 10 to 12).

To create the incision 9 in the wall 8 of the blood vessel 6, the scissors 12 in the open configuration is pushed distally through the wall 8 (FIGS. 13 and 16), and the scissors 12 is moved from the open configuration to the closed configuration (FIGS. 17 to 20). In this manner the incision 9 through the wall 8 is created around the engagement element 1 and the outer sheath 200 both of which extend through the opening 5 in the closed scissors 12 (FIG. 20). The incision 9 is created inclined to the plane of the wall 8, with the flap 7 of tissue wall formed at the side of the incision 9.

Figure 27:
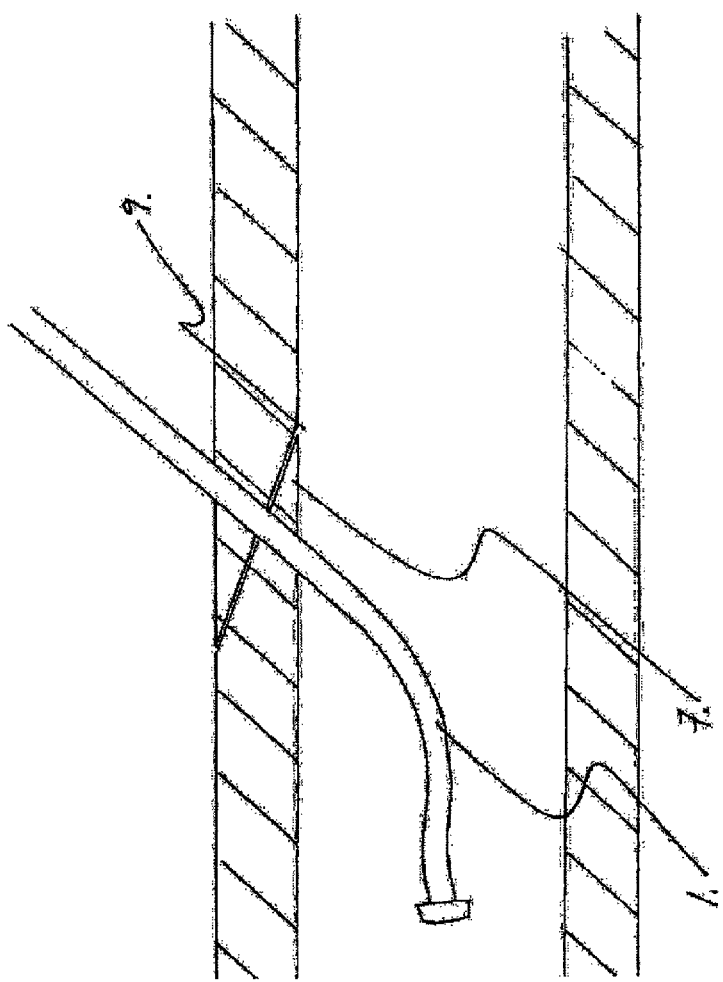

The scissors 12 may then be moved from the closed configuration to the open configuration and pulled proximally out of the incision 9 (FIGS. 21 to 23). The incising element 3 and the outer sheath 200 may be withdrawn (FIGS. 24 to 26). As illustrated in FIGS. 25 to 27, the engagement element 1 is pierced through the flap 7 of tissue wall and through the wall 8 of the blood vessel 6 at the opposite side of the incision 9.

The guidewire 14 is introduced into the interior 11 through the incision 9 prior to the introduction of the introducer sheath 13.

Figure 29:
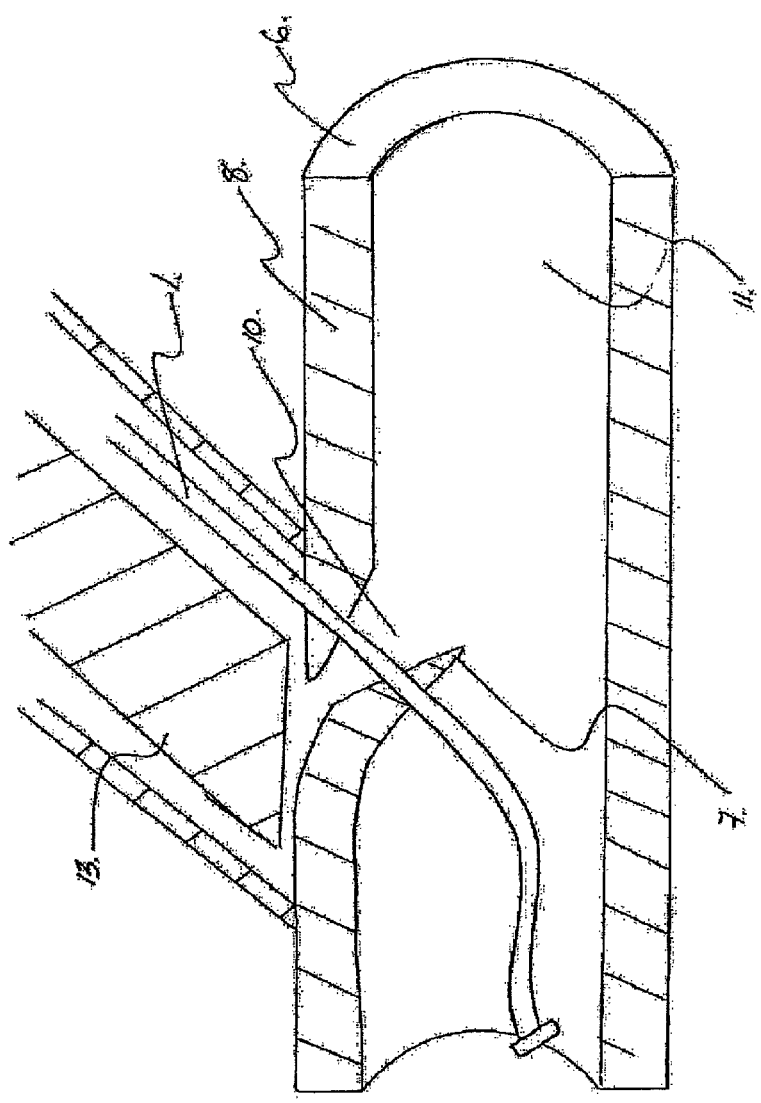
Figure 30:
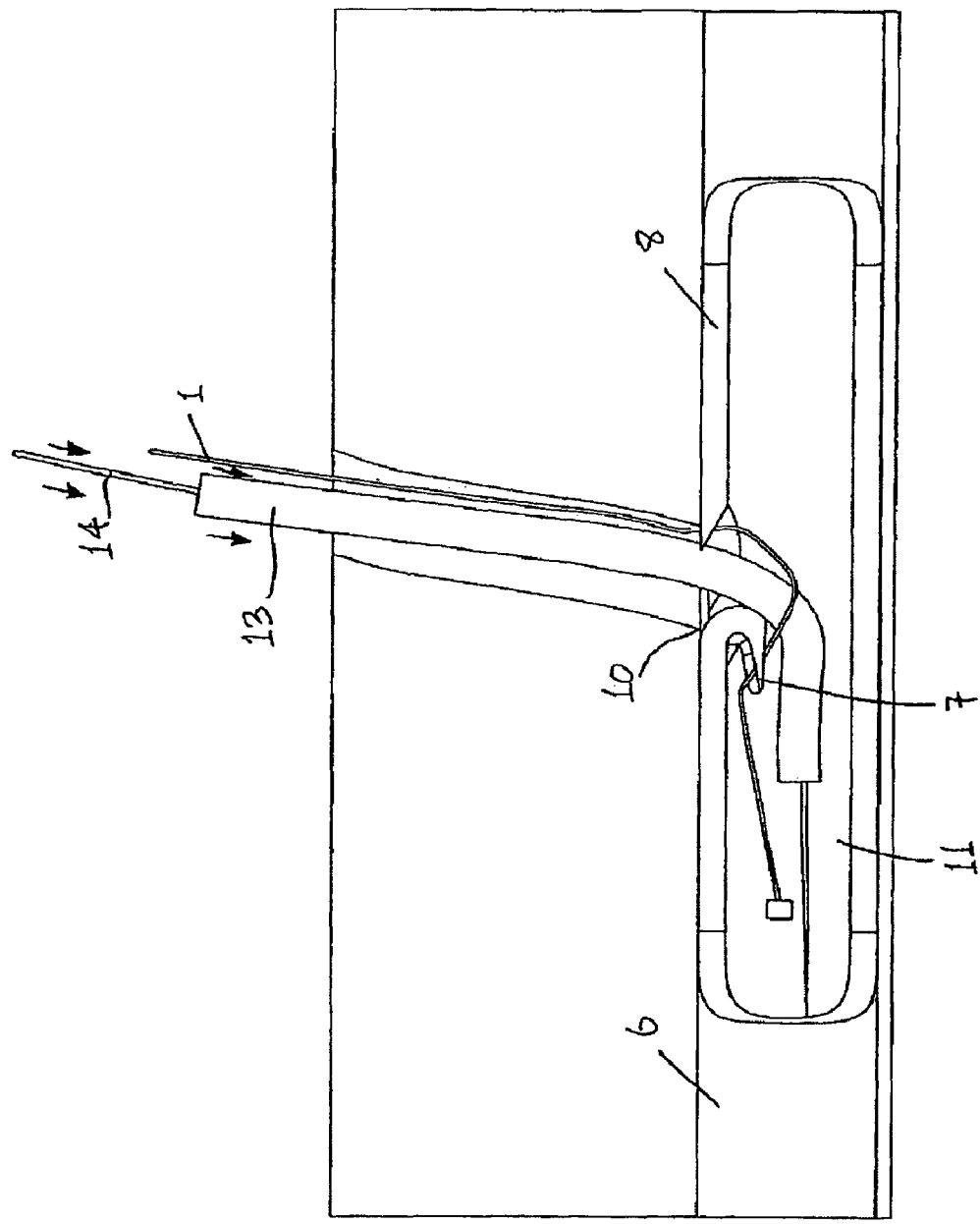

To access the interior 11 of the blood vessel 6, an introducer sheath 13 engages the flap 7 and pushes the flap 7 distally (FIG. 29). By pushing the flap 7 distally, the flap 7 is moved aside to form the opening 10 to the interior 11 of the blood vessel 6 (FIG. 30). The flap 7 moves relative to the wall 8 of the blood vessel 6 in a substantially hinging manner from a sealing configuration, in which the flap 7 seals across the opening 10 (FIG. 28), to an access configuration, in which the flap 7 is moved aside to reveal the opening 10 (FIG. 30). The axis of hinging of the flap 7 is substantially parallel to the plane of the wall 8. In the access configuration, the flap 7 is located within the interior 11 of the blood vessel 6.

One or more medical devices, such as the introducer sheath 13, and/or a guidewire 14, and/or a guide catheter, and/or a delivery catheter may therefore be inserted into the interior 11 of the blood vessel 6 through the opening 10 to access the interior 11, and a medical procedure may be performed within the interior 11 of the blood vessel 6 using the introducer sheath 13/guidewire 14/guide catheter/delivery catheter.

Figure 31:
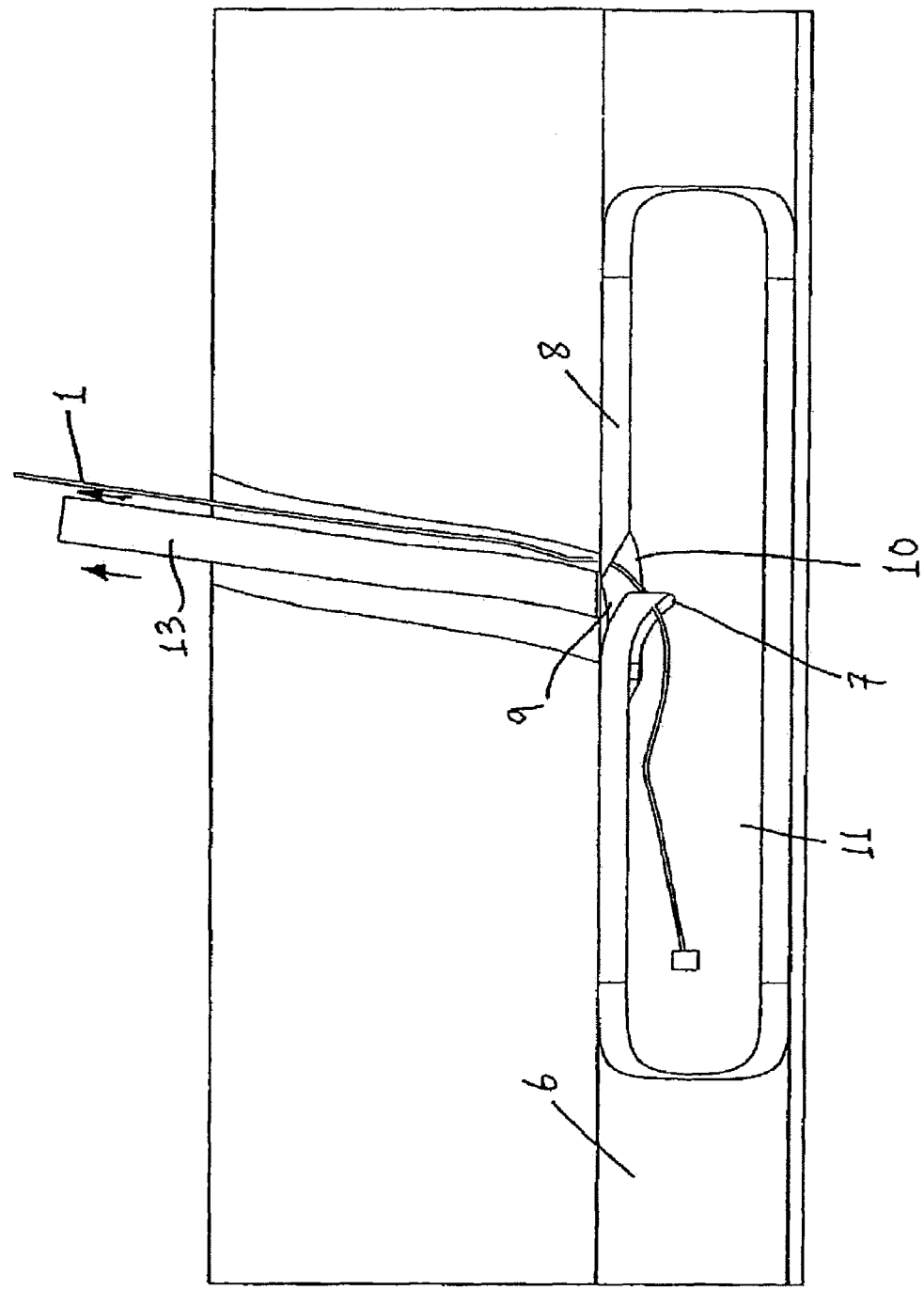
FIG. 31 is a partially cross-sectional, side view illustrating removal of the introducer sheath and the guidewire.
Figure 32:
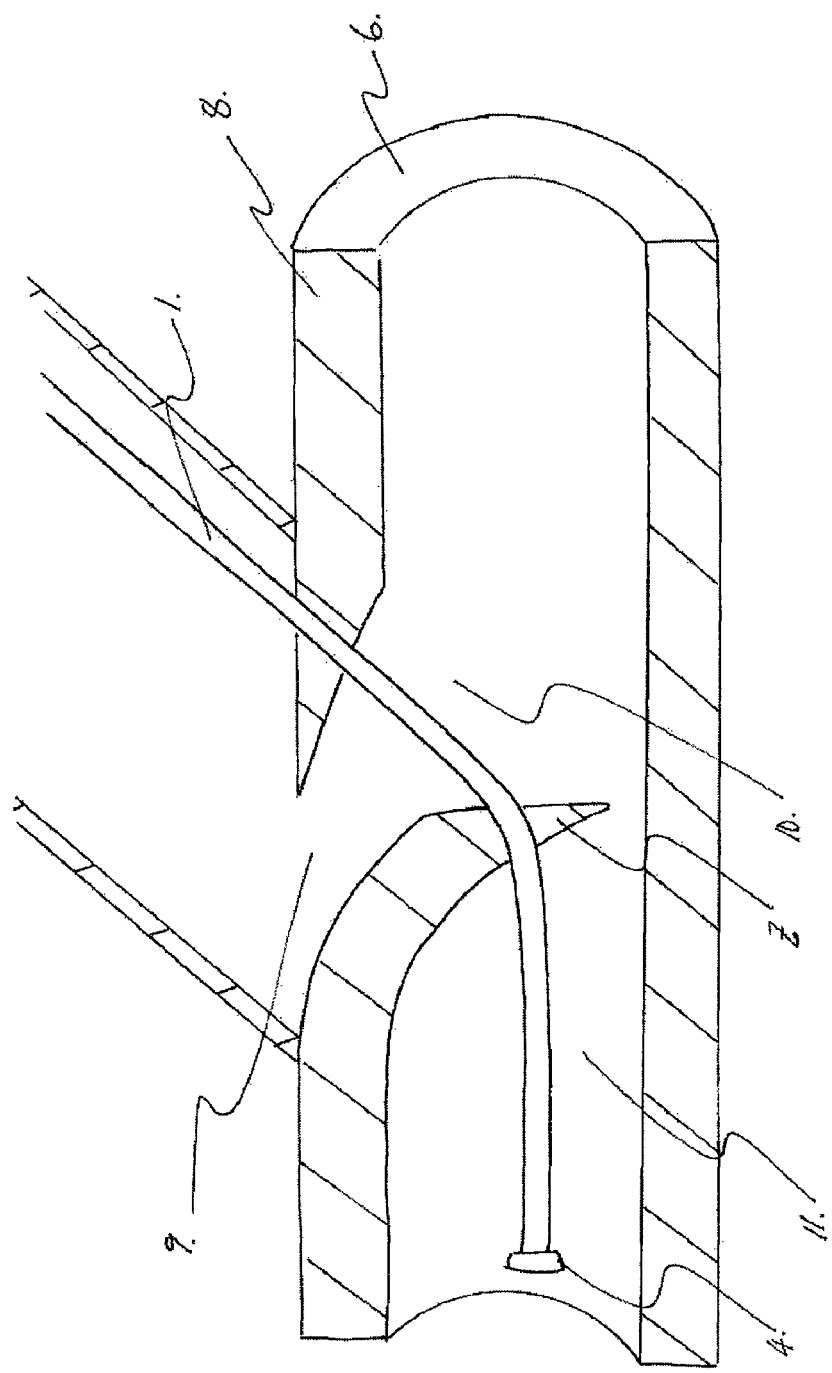
FIG. 32 is a partially cross-sectional, side view illustrating activation of a trapping matter of the engagement element of FIG. 6.
Figure 34:
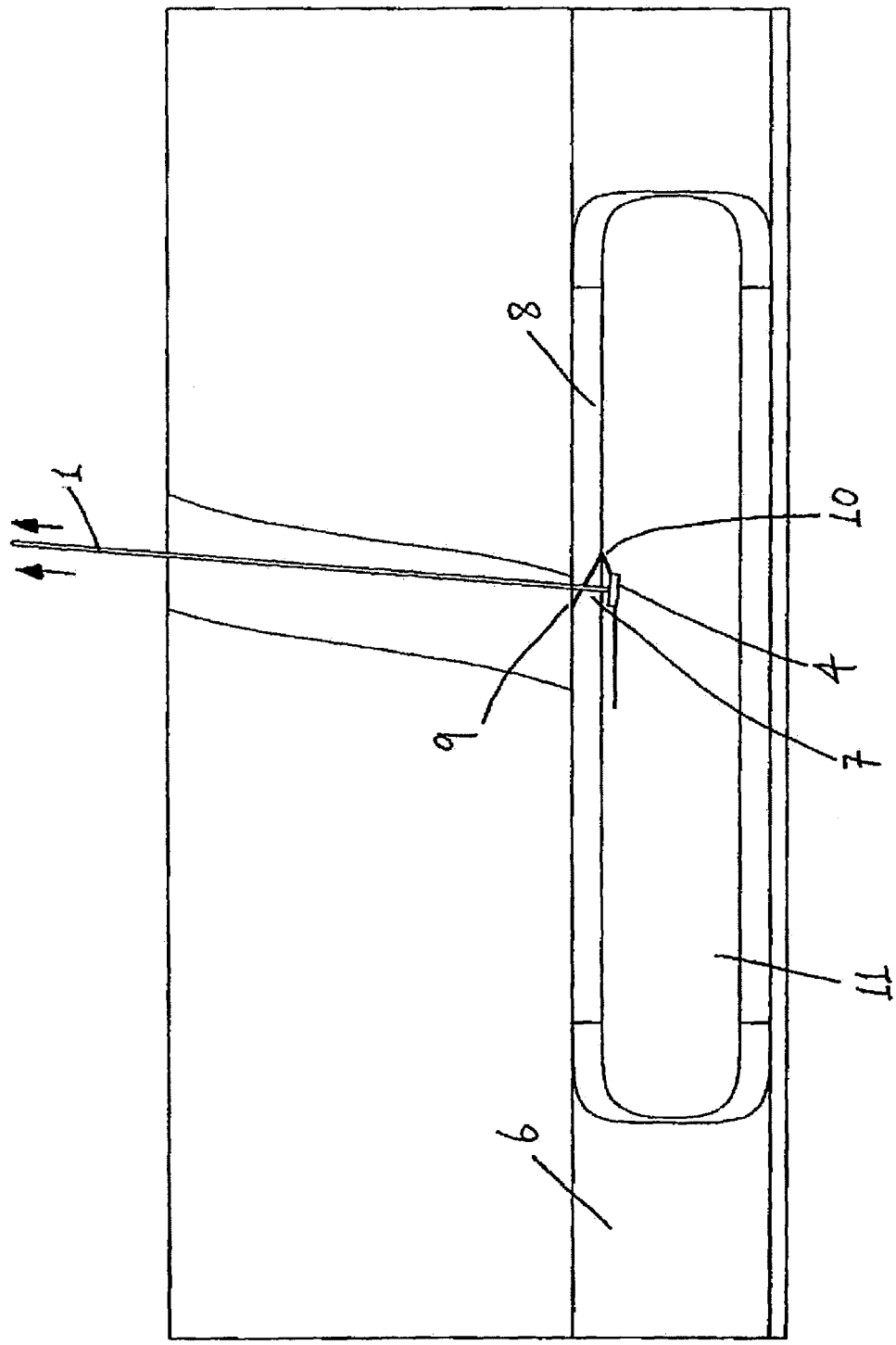
FIG. 34 is a partially cross-sectional, side view illustrating closure of the flap using the engagement element of FIG. 6.

After completion of the medical procedure, the introducer sheath 13, and/or any other medical devices, are withdrawn from the interior 11 of the blood vessel 6 through the opening 10 (FIG. 31). To seal across the opening 10, the retaining element part 4 is inflated from the delivery configuration to the deployed configuration (FIG. 32), and the engagement element 1 is pulled proximally until the balloon part 4 engages the flap 7 (FIG. 33). By further pulling of the engagement element 1 proximally, the flap 7 is pulled proximally until the flap 7 moves back across the opening 10 to seal across the opening 10 (FIG. 34). The flap 7 moves relative to the wall 8 of the blood vessel 6 in a substantially hinging manner from the access configuration (FIG. 30) to the sealing configuration (FIG. 34). In the sealing configuration, the flap 7 engages the wall 8 of the blood vessel 6 at the opposite side of the incision 9.

Figure 35:
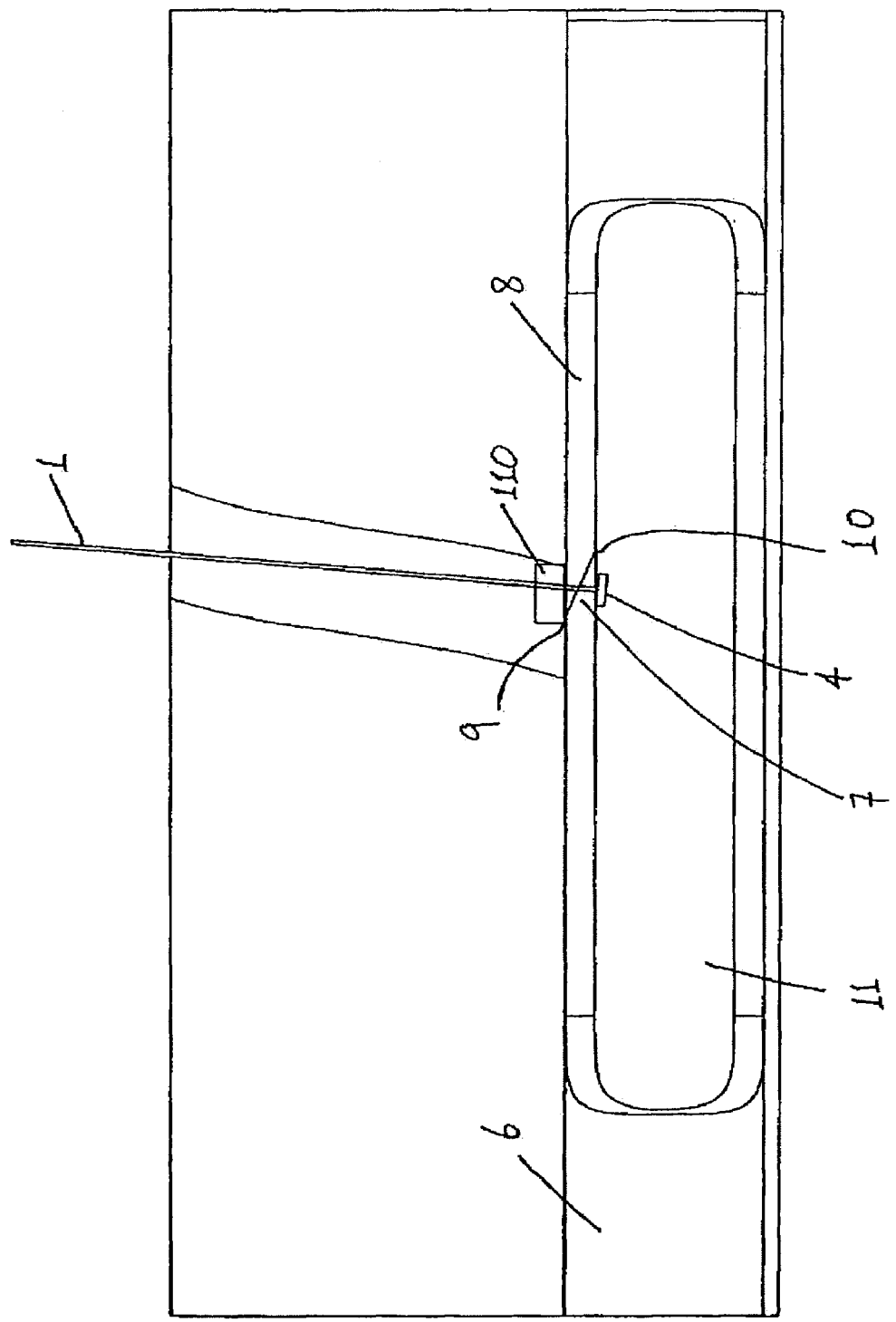
Figure 35:
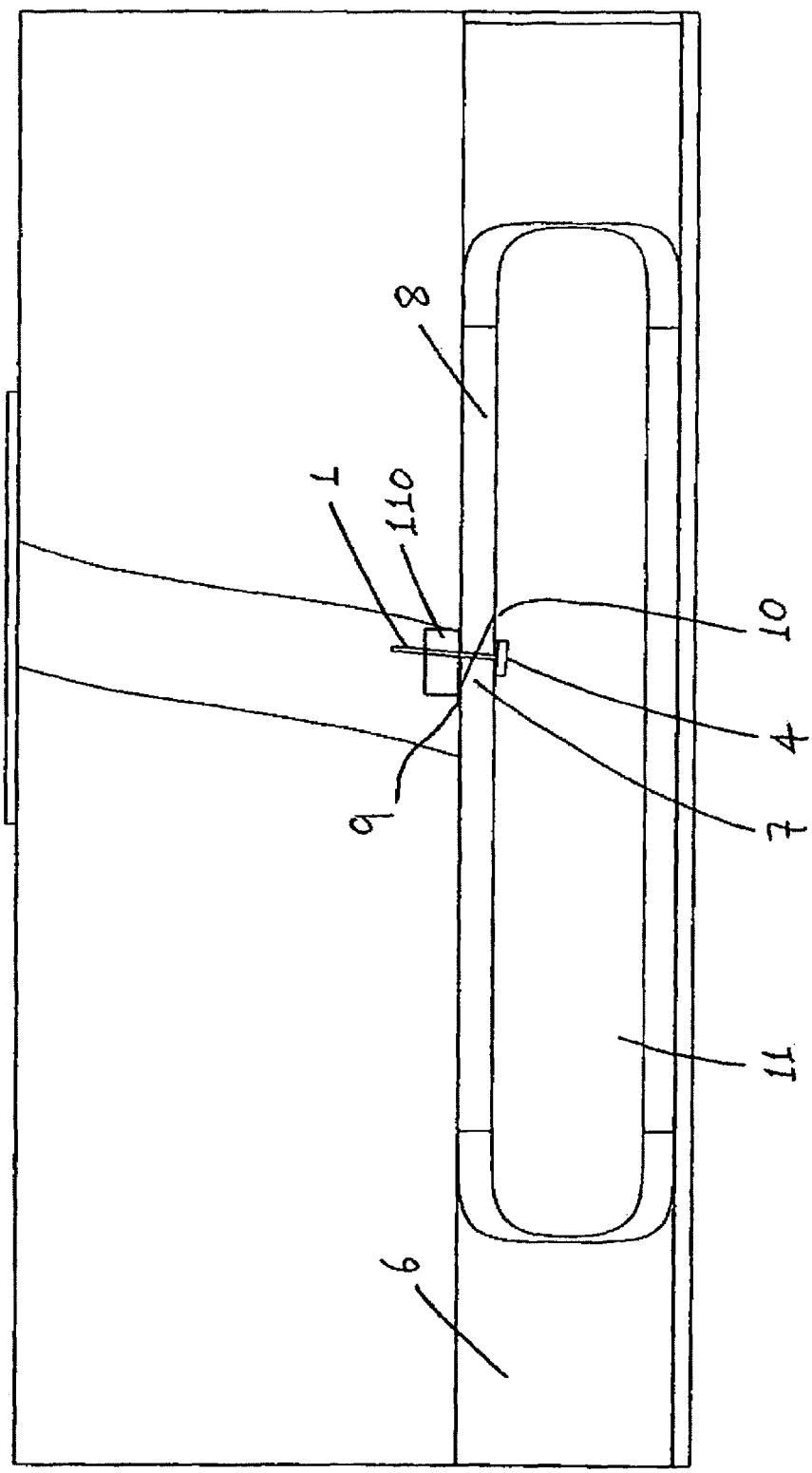

After sealing across the opening 10, the engagement element 1 may remain in position (FIG. 35). An anchoring element 110 is threaded onto the engagement element 1 and positioned on the external wall of the vessel 6. The anchoring element 110 serves to secure the incision area 10 and seal the vessel wall 8. The anchoring element 110 may be of a biodegradable polymer which slides down over the engagement element 1. Alternatively the retaining element part 4 may be deflated from the deployed configuration to the delivery configuration, and the engagement element 1 may be withdrawn from the flap 7 and from the wall 8 of the blood vessel 6.

It will be appreciated that the engagement element 1 may be provided with alternative means of engaging the flap 7. For example alternative means of moving a part of the engagement element 1 between the delivery configuration and the deployed configuration may be employed, for example, by expanding / contracting the part of the engagement element, instead of employing the expandable retaining element part 4.

As a further alternative, the part of the engagement element 1 may be moved from the delivery configuration to the deployed configuration to engage the flap 7. After sealing across the opening 10, the engagement element 1 may remain in position. The part of the engagement element may be biodegradable/bioresorbable.

The medical device of FIGS. 1 to 35 is an example of the double trap system which captures both sides/vessel wall flaps of the incision site 9 with a threaded through element, for example, the engagement element 1 with the expandable retaining element 4. The cutter 3 makes the incision 9 without cutting through the engagement element 1 which is put in place in the vessel wall 8 prior to the cutting step. This is accomplished by deploying a protective sheath 2 to cover and protect the engagement element 1 before the cutting plunger 3 is activated. Once activated the scissors 12 cuts through the vessel wall 8 with the scissor blades opened. When the blades encounter the sheath 2 protecting the engagement element 1, they 'scissor' around the protective sheath 2 and cleanly cut the tissue 8 leaving a smooth incision 9 in the vessel 6. When the device is withdrawn, the scissors 12 opens and is retracted into the body of the cutting device 3.

To start the procedure, the first operation used is the Seldinger technique. Here a needle is used to puncture the vessel wall 8 and deliver a device such as an engagement element through the lumen of the needle into the vessel 6. Once this is completed, the needle is removed from the patient and the engagement element is left in place.

Figure 6:
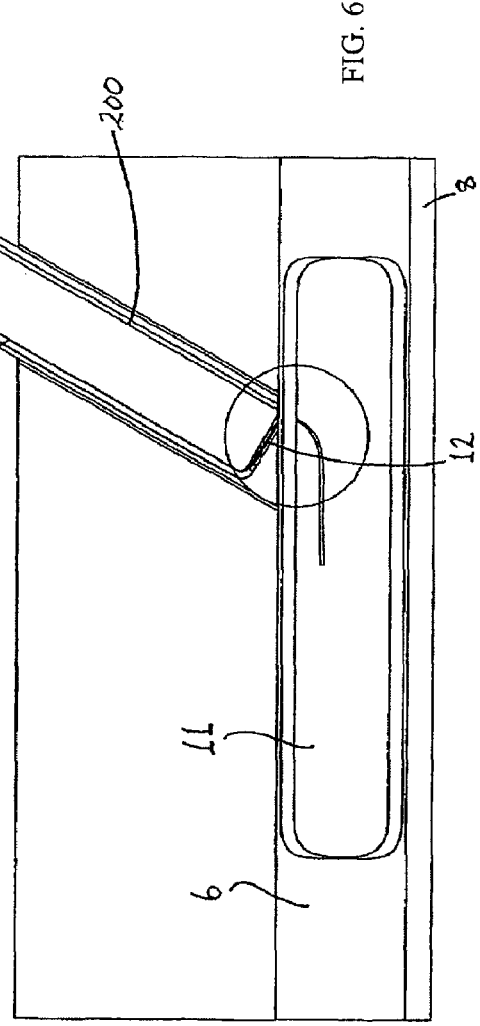
FIG. 6 is a partially cross-sectional, side view of the engagement element of FIG. 1 and an incising element of the medical device, in use at a first step of a method of accessing an interior of a body part according to the invention.
Figure 7:
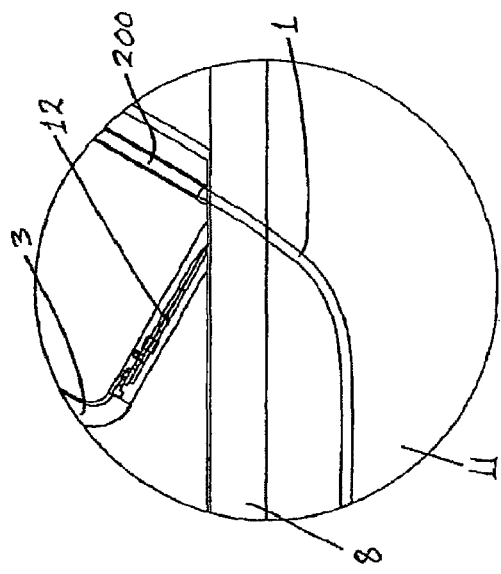
FIG. 7 is an enlarged, cross-sectional, side view of the engagement element and the incising element of FIG. 6.

The sequence of FIGS. 6 to 30 shows the following:

Step 1: The cutting device 3 is delivered down the tissue tract from the skin to the outside of the vessel wall 8 over the engagement element which directs the cutter 3 to its correct location on the vessel wall 8 (FIGS. 6 to 8).

FIG. 9 shows an exploded view of the scissors component 12 seated in its pocket in the cutting device 3.

Step 2: The protective sheath 2 is deployed over the guidewire and the guidewire is exchanged with an engagement element 1 (FIGS. 10 to 12).

Step 3: The plunger is activated and the cutter 3 is delivered into the vessel wall 8 and around the protective sheath 2 (FIGS. 13 to 16).

Step 4: The plunger is pushed fully down and the scissors 12 has wrapped around the protective sheath 2, effecting a clean cut through the vessel wall 8 (FIGS. 17 to 20).

Step 5: The plunger is retracted and the cutting blades 12 are returned to their starting location in the cutting device body 3 (FIGS. 21 to 23).

Step 6: The cutting device 3 is withdrawn from the tissue tract and the engagement element 1 is left in the incision 9 (FIGS. 24 to 27).

The next sequence of events is for the delivery of the introducer sheath 13 and the guidewire 14. This sequence is shown in FIGS. 29 and 30.

Figure 40:
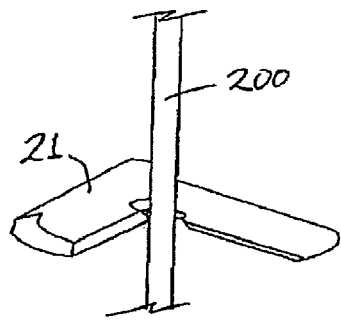
FIGS. 40 and 41 are views similar to FIGS. 36 and 37 of an incising element and an engagement element of another medical device according to the invention.
Figure 41:
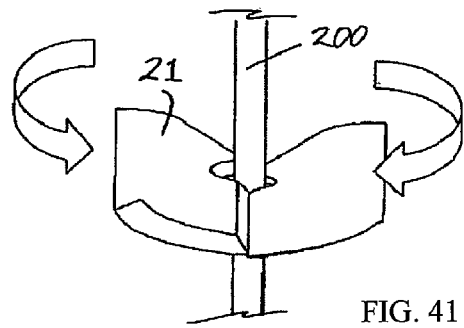
Figure 36:
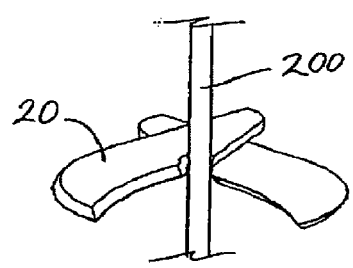
FIG. 36 is a perspective view of an incising element in an open configuration and an engagement element of another medical device according to the invention.
Figure 37:
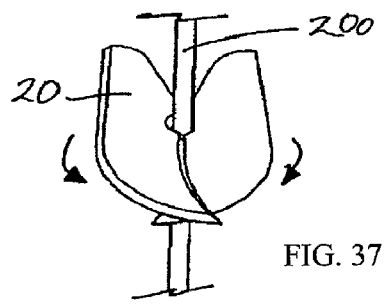
FIG. 37 is a perspective view of the incising element of FIG. 36 in a closed configuration and the engagement element of FIG. 36.
Figure 38:
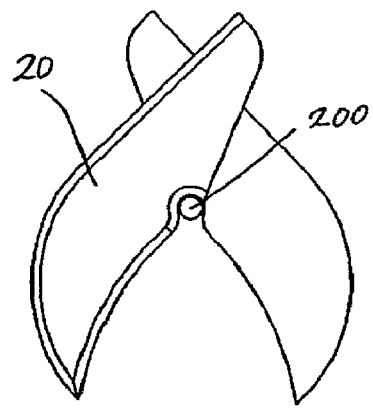
FIG. 38 is a plan view of the incising element of FIG. 36 in the open configuration and the engagement element of FIG. 36.
Figure 39:
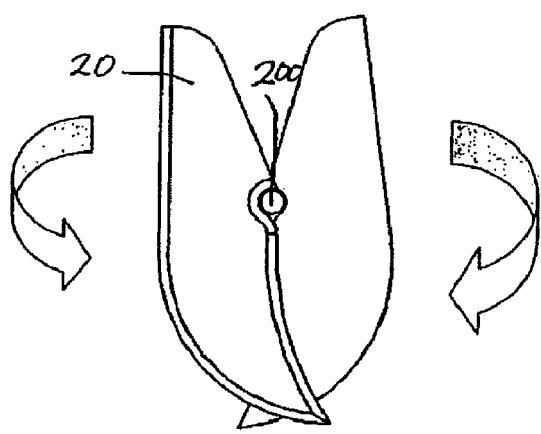
FIG. 39 is a plan view of the incising element of FIG. 36 in the closed configuration and the engagement element of FIG. 36.
Figures 44, 45:
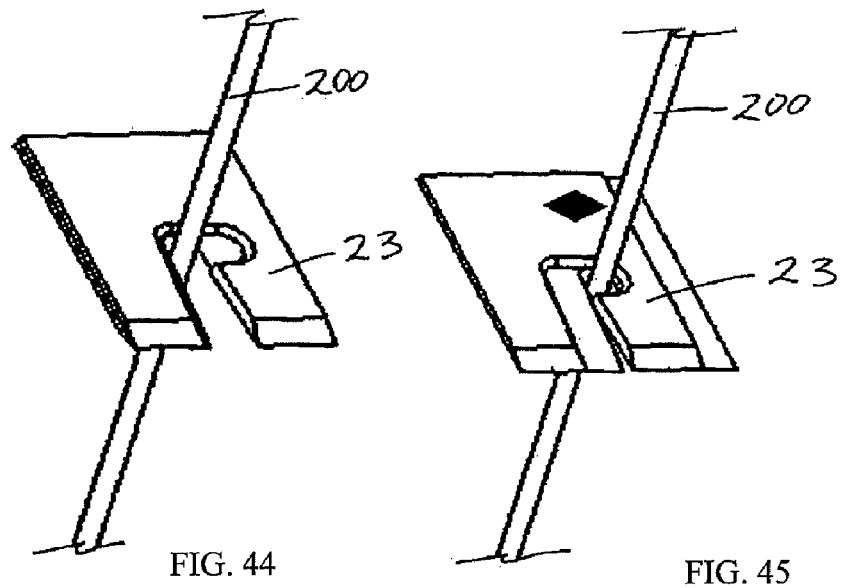
FIGS. 44 and 45 are views similar to FIGS. 36 and 37 of an incising element and an engagement element of another medical device according to the invention.
Figures 42, 43:
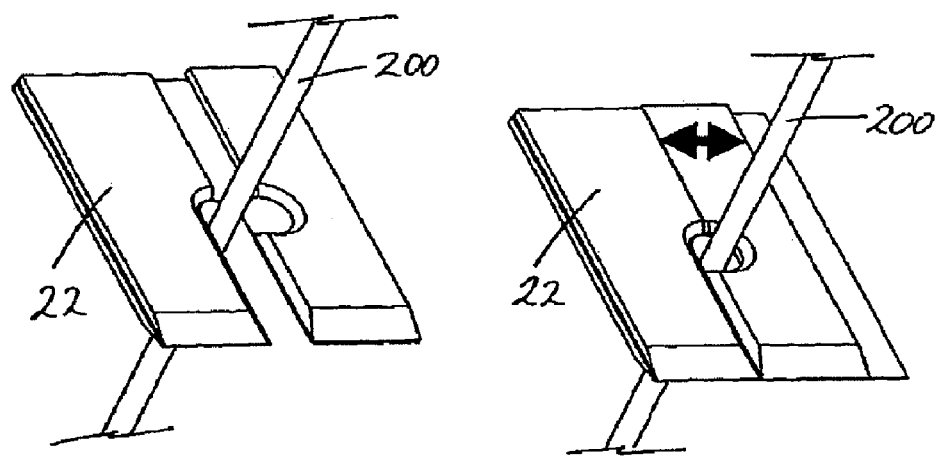
FIGS. 42 and 43 are views similar to FIGS. 36 and 37 of an incising element and an engagement element of another medical device according to the invention.
Figure 46:
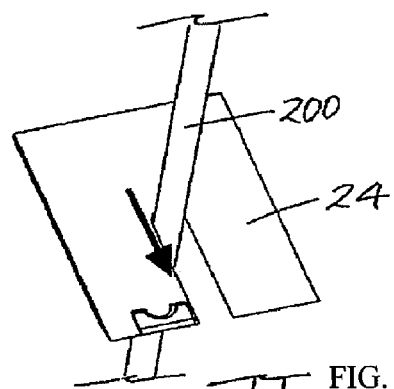
FIGS. 46 to 48 are perspective views of an incising element and an engagement element of another medical device according to the invention, in use.
Figure 47:
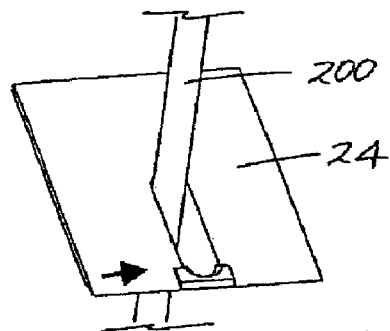
Figure 48:
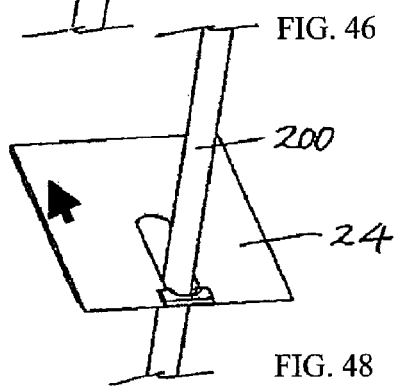
Figure 49:
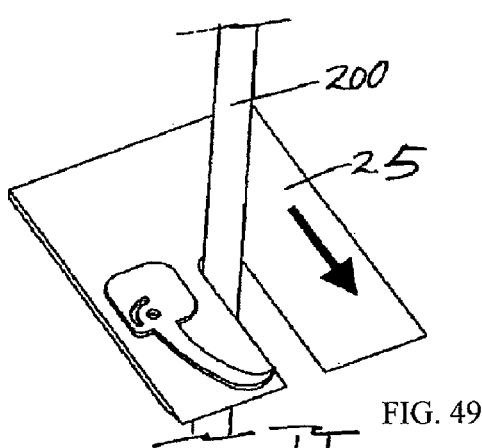
FIGS. 49 to 52 are perspective views of an incising element and an engagement element of a further medical device according to the invention, in use.
Figure 50:
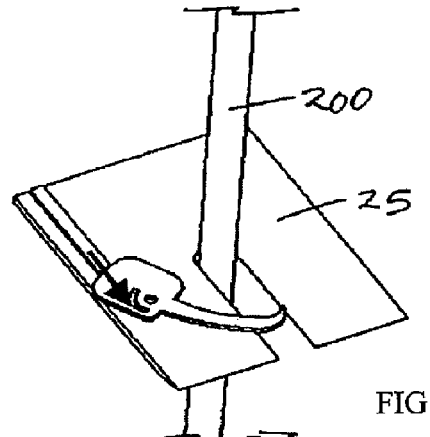
Figure 51:
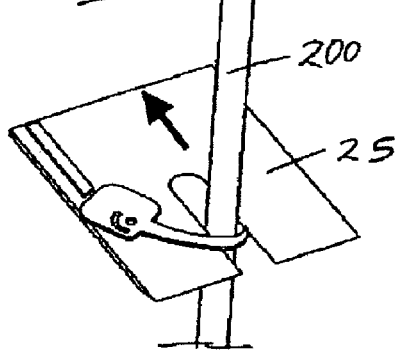
Figure 52:
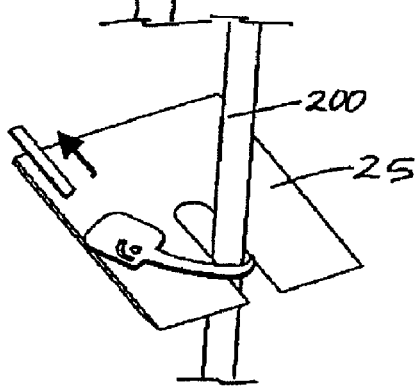

The incising element of the medical device may be provided in a number of possible configurations. For example, the incising element may have a scissors type cutter arrangement 20, as illustrated in FIGS. 36 to 39, or an alternative scissors type cutter arrangement 21, as illustrated in FIGS. 40 and 41, or the incising element may have a sliding type cutter arrangement 22, as illustrated in FIGS. 42 and 43, or an alternative sliding type cutter arrangement 23, as illustrated in FIGS. 44 and 45, or the incising element may have a push/pull type cutter arrangement 24, as illustrated in FIGS. 46 to 48, or an alternative push/pull type cutter arrangement 25, as illustrated in FIGS. 49 to 52.

Figure 53:
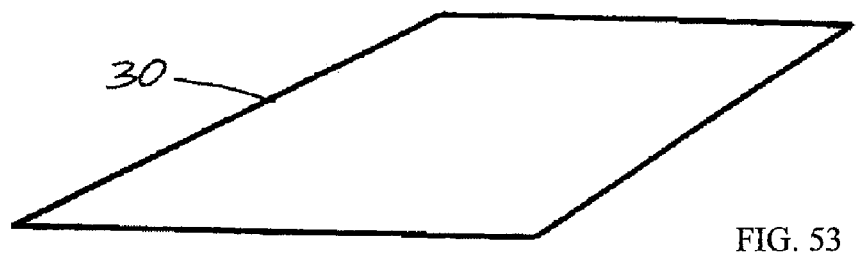
FIG. 53 is a perspective view illustrating the profile of an incision in a method of accessing an interior of a body part according to the invention.
Figure 54:
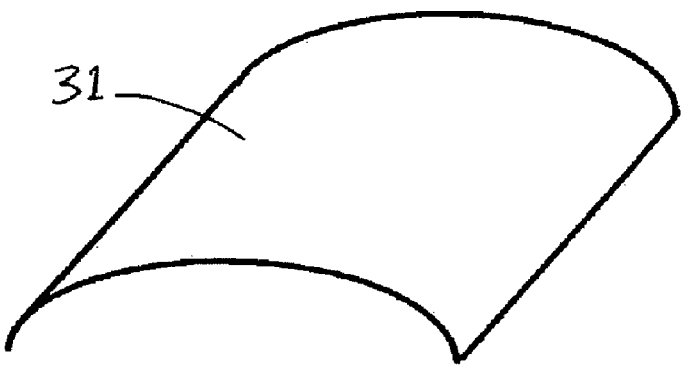
FIGS. 54 to 56 are perspective views illustrating alternative incision profiles.
Figure 55:
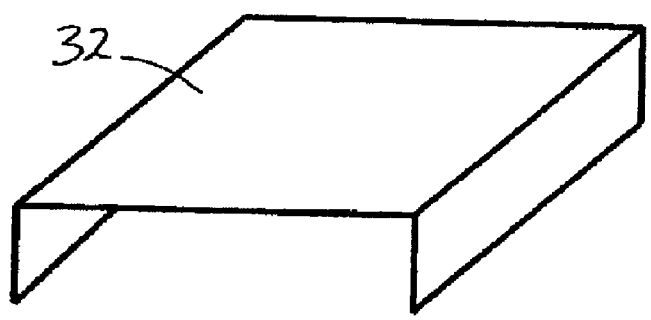
Figure 56:
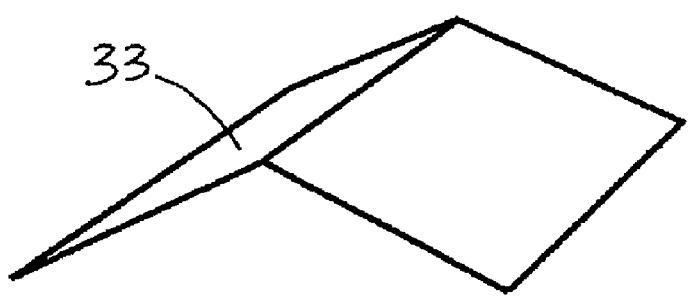
Figure 56:
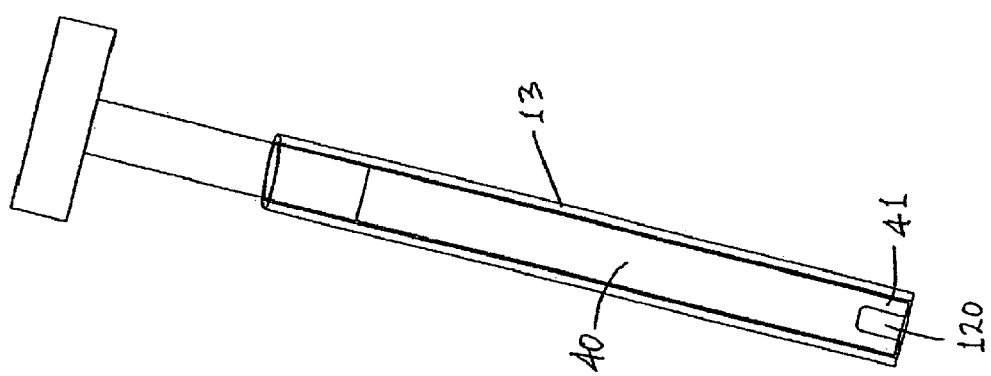
Figure 56B:
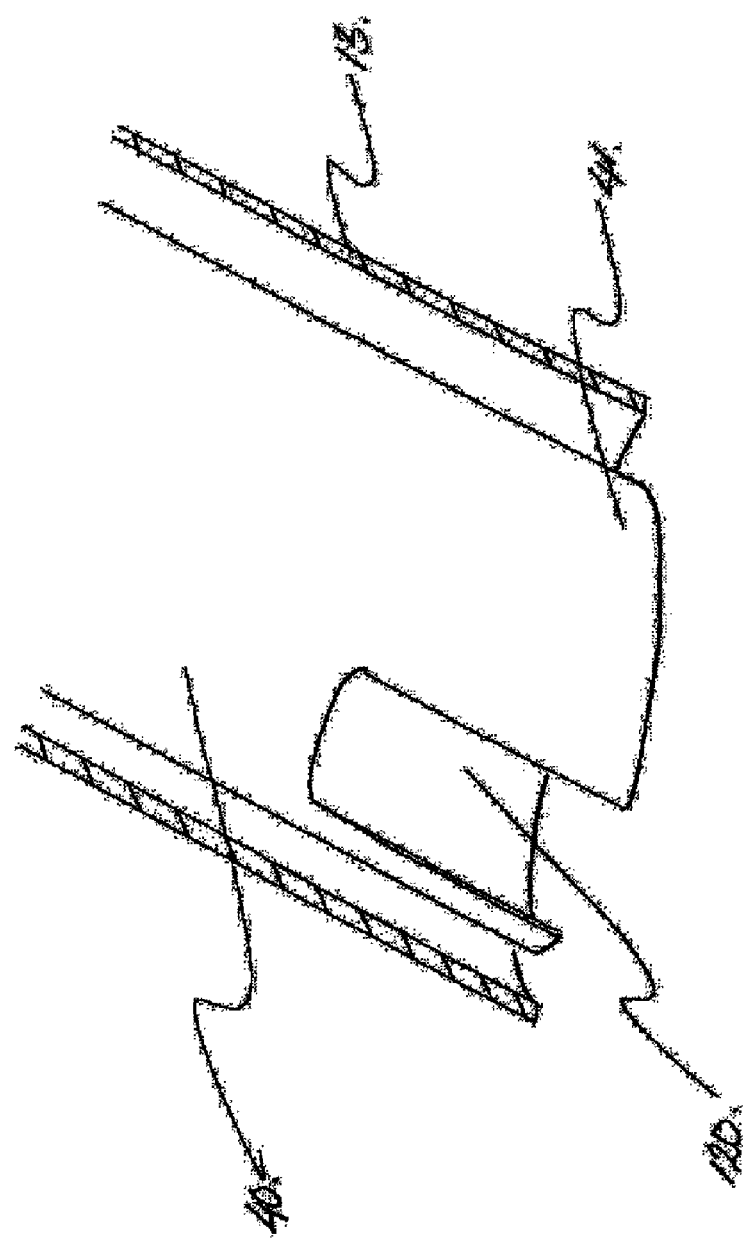
Figure 56:
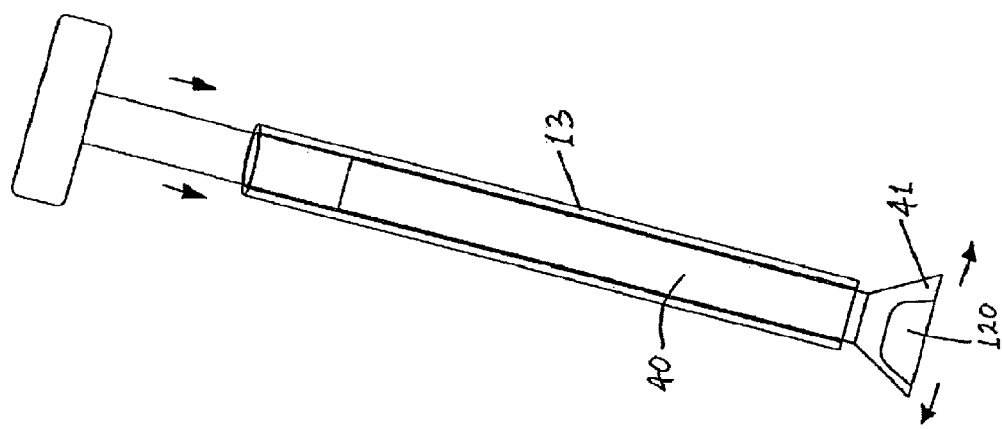
Figure 56:
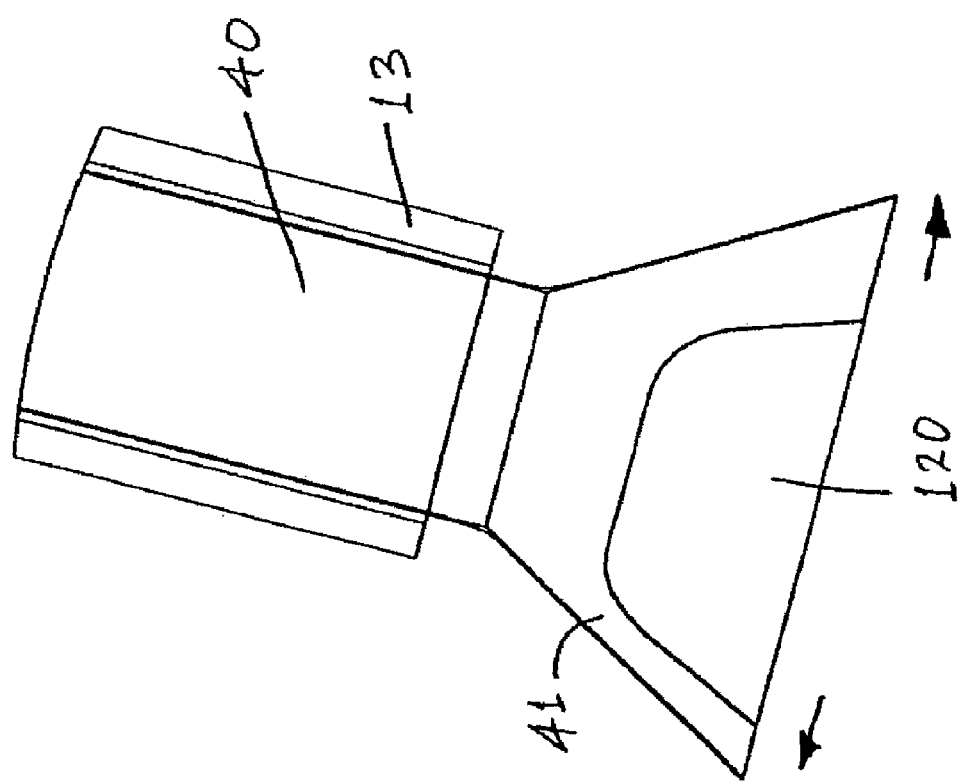
Figure 56:
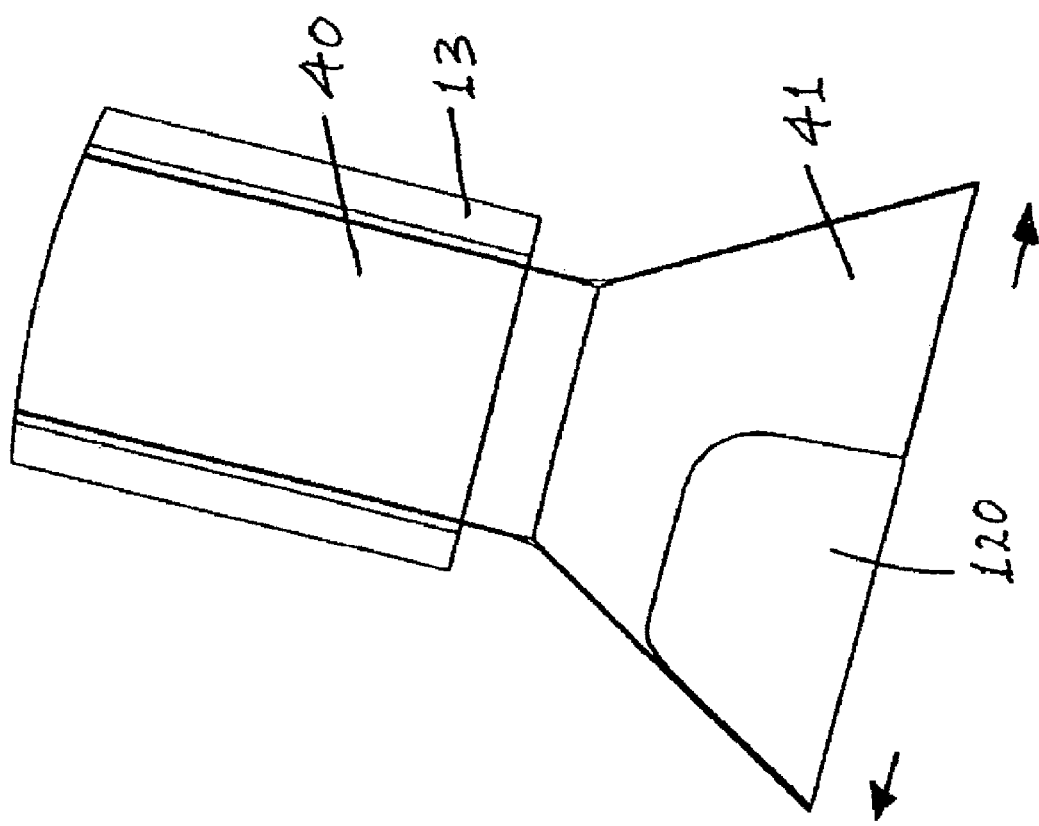

The incision created in the wall 8 of the blood vessel 6 may have one of a variety of possible profiles. For example, the incision may have a linear profile 30 (FIG. 53), or an arch profile 31 (FIG. 54), or a channel profile 32 (FIG. 55), or a triangular profile 33 (FIG. 56). These incision profiles may be achieved by suitable profiles on the incising element. It will be appreciated that a broad range of shapes from linear to angled, such as square, pentagon, dodecahedron, to a smooth curved arch may be employed.

In FIGS. 56(*a*) to 68, there is illustrated another medical device according to an aspect of the invention, which is similar to the medical device described previously with reference to FIGS. 1 to 35, and similar elements in FIGS. 56(*a*) to 68 are assigned the same reference numerals.

In this case, the incising element 40 comprises a frustoconical catheter 41 at the distal end of the incising element 40.

The engagement element 1 is introduced into the interior 11 in a manner similar to that described previously with reference to FIGS. 5(*a*) to 5(*d*).

The incising element 40 is advanced concentrically over the engagement element 1 which is pierced through the wall 8 of the blood vessel 6, in this case, to create the incision 9 in the wall 8. The protective sheath is therefore not required in this case.

Referring to FIGS. 56(*a*) to 56(*d*), the punch cut device comprises an outer sheath element 13, within which is housed an expandable cutting element 41 and mechanisms 40 to activate and withdraw the cutting element 41.

The cutting element blade system 41 will expand outwardly, increasing its diameter when pushed distally from the outer protective sheath 13 (FIGS. 56(*c*) and 56(*d*)).

This design of cutting element 41 can be accomplished by, for example, using a shape memory system with metal and polymer components, which when unrestrained expand radially to take the shape of a cone.

Figure 61:
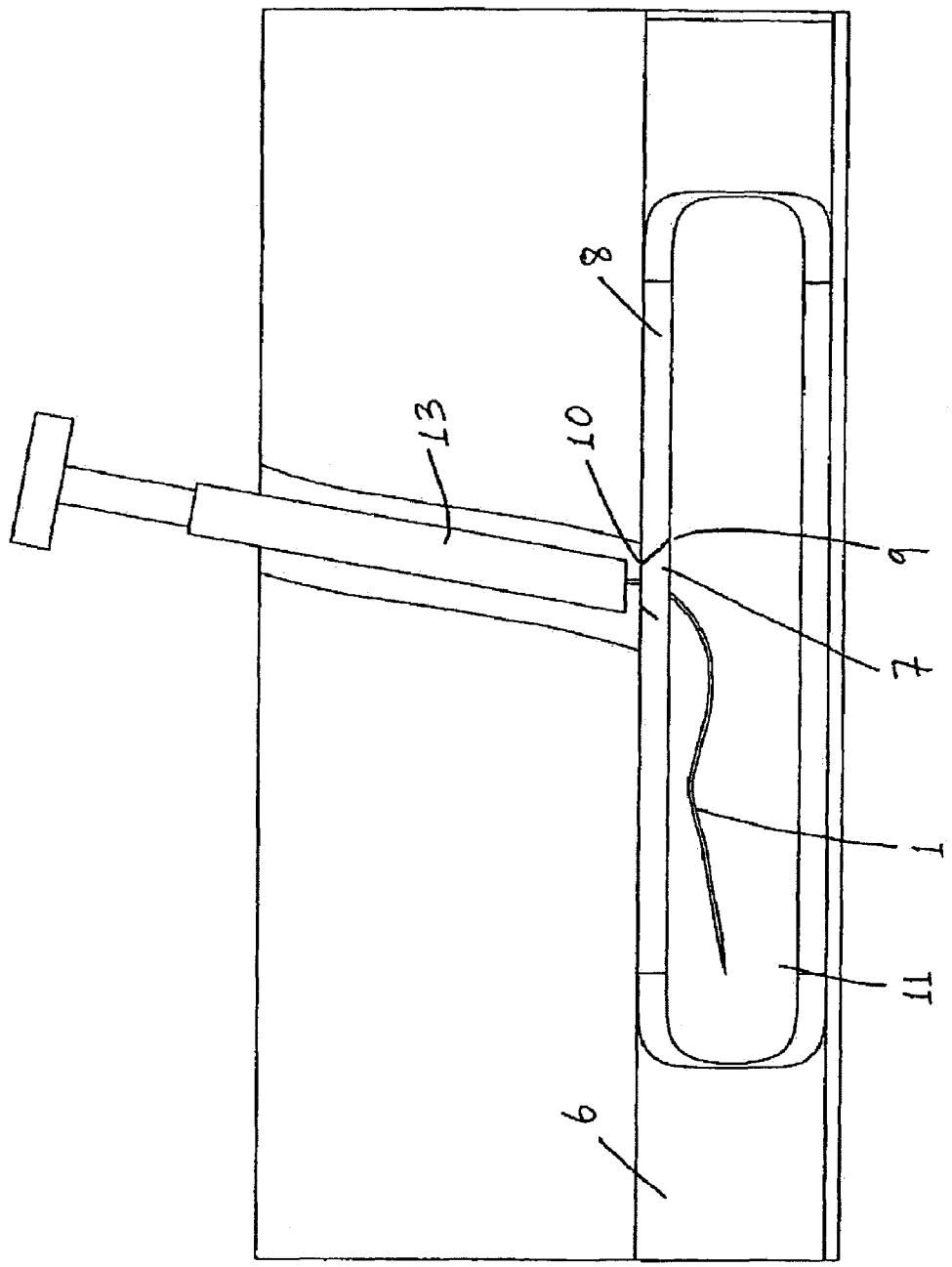

When used to make an incision 9 on a vessel wall 8, this results in a cone shaped cut 9 being formed in the vessel wall 8, with the smaller diameter cut on the outer wall of the vessel 6 and the larger diameter cut on the inside wall of the vessel 6 (FIG. 61).

The cutting element blade 41 is designed with a recessed notch 120 at which the vessel wall 8 is not cut. This ensures that there is a secure connection of the vessel wall 8 to the cut wall flap 7.

The punch cut device has internal lumens which can accommodate guidewires, engaging elements or similarly dimensioned devices.

The mode of operation of the punch cut device is as follows:

In its starting position, the cutting element 41 is retracted in its protective sheath 13 (FIGS. 56(*a*) and 56(*b*)).

As the cutting element 41 is activated, it emerges from the distal end of the protective sheath 13 and exposes the cutting element 41 which expands radially.

As the cutter 41 is pushed further distally to the end-stop, it continues to expand radially to its pre-set size and shape (FIGS. 56(*c*) to 56(*e*)).

When used to make an incision 9 in a hollow vessel 6, the shape of the cutting element 41 is such as to allow a portion of the vessel wall 8 to remain un-cut even when it is activated fully. This uncut portion forms the anchor for the tissue flap 7 and is an integral part of the system. Another embodiment of this cutter is shown in FIG. 56(*e*) where the non-cutting slot 120 is extended the full length of the cutting blade 41. This will allow the device to be used with thin vessel walls.

The longitudinal axis of the incising element 40 is not necessarily inclined relative to the plane of the wall 8 of the blood vessel 6.

Figure 58:
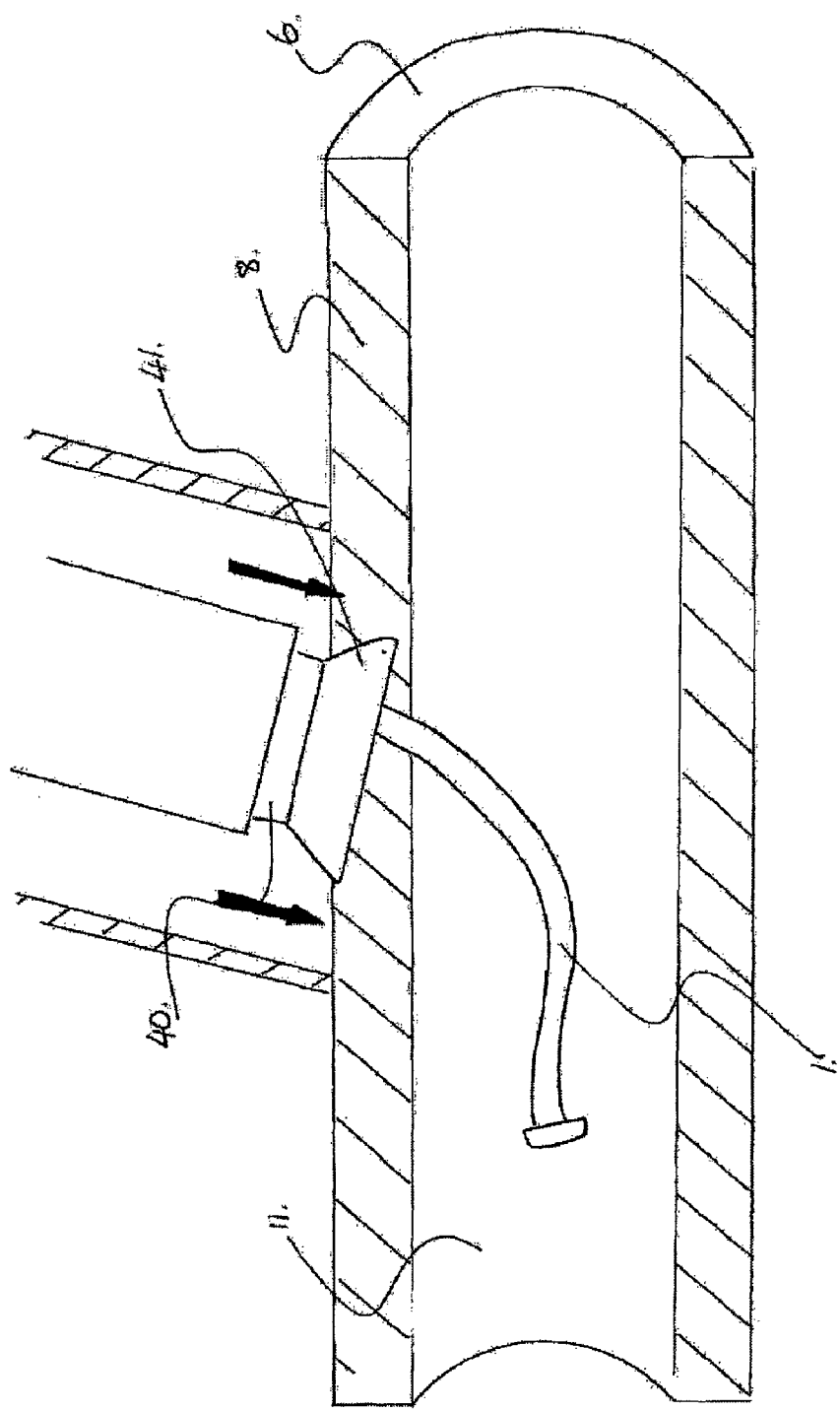
Figures 59, 60:
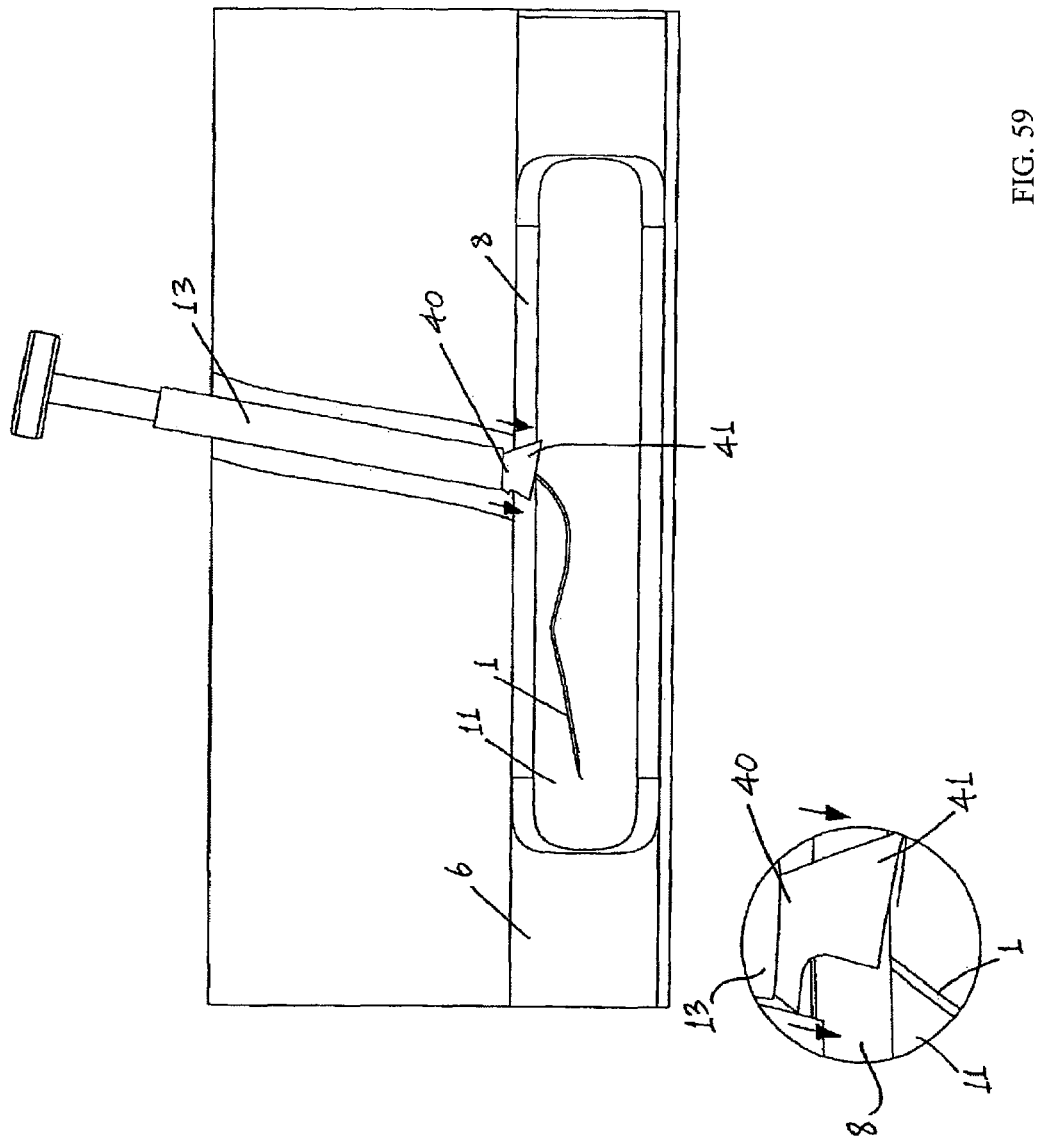

To create the incision 9 in the wall 8 of the blood vessel 6, the access channel is initially formed using the modified Seldinger technique, where the trapping element 1 acts as a guidewire for the introduction of the cutting device 40. The cutting device 40, unlike in the normal Seldinger technique which uses a dilator tip with the introduction sheath to open the channel and push through the vessel, will have a flat tip introducer system which will butt up against the wall of the vessel 6. Often surgeons use a scalpel to nick the skin at the initial puncture site so as to allow easier entry of the introducer sheath through the skin in through the tissue of the vessel 6. The cutter 41 is then pushed distally through the wall 8 (FIGS. 58 to 60). The incision 9 is created inclined to the plane of the wall 8, with the flap 7 of tissue wall formed at the side of the incision 9. The cutter 41 may then be pulled proximally out of the incision 9 (FIG. 61). The engagement element 1 is pierced through the flap 7 of tissue wall only, in this case, and is not pierced through the wall 8 of the blood vessel 6 at the opposite side of the incision 9.

FIGS. 57 to 68 illustrate the wedge/inverted cone device, which is an example of a single trap system where the cutter 41 is an inverted cone, with a slot removed, which is housed in the introducer sheath 13. The engagement element device 1 is in place prior to insertion of the cutter device 41, and the cutter device 41 is guided down the tissue channel over the engagement element 1 for placement of the device on the outside of the vessel wall 8. The cutter 41 will cut through the vessel wall 8 while leaving a strip of wall uncut and attached to the body of the vessel wall 8. This strip acts as an anchor tag which, along with the engagement element 1, guides the sealing element 7 back accurately into the opening 10 created by the cutting blade 41 in the vessel wall 8.

To start the procedure, the first operation used is the Seldinger technique. Here a needle is used to puncture the vessel wall 8 and deliver a guidewire through the lumen of the needle into the vessel 6. Once this is completed, the needle is removed from the patient and the guidewire is left in place.

The engagement element 1 is introduced into the interior 11 in a manner similar to that described previously with reference to FIGS. 5(*a*) to 5(*d*).

Figure 57:
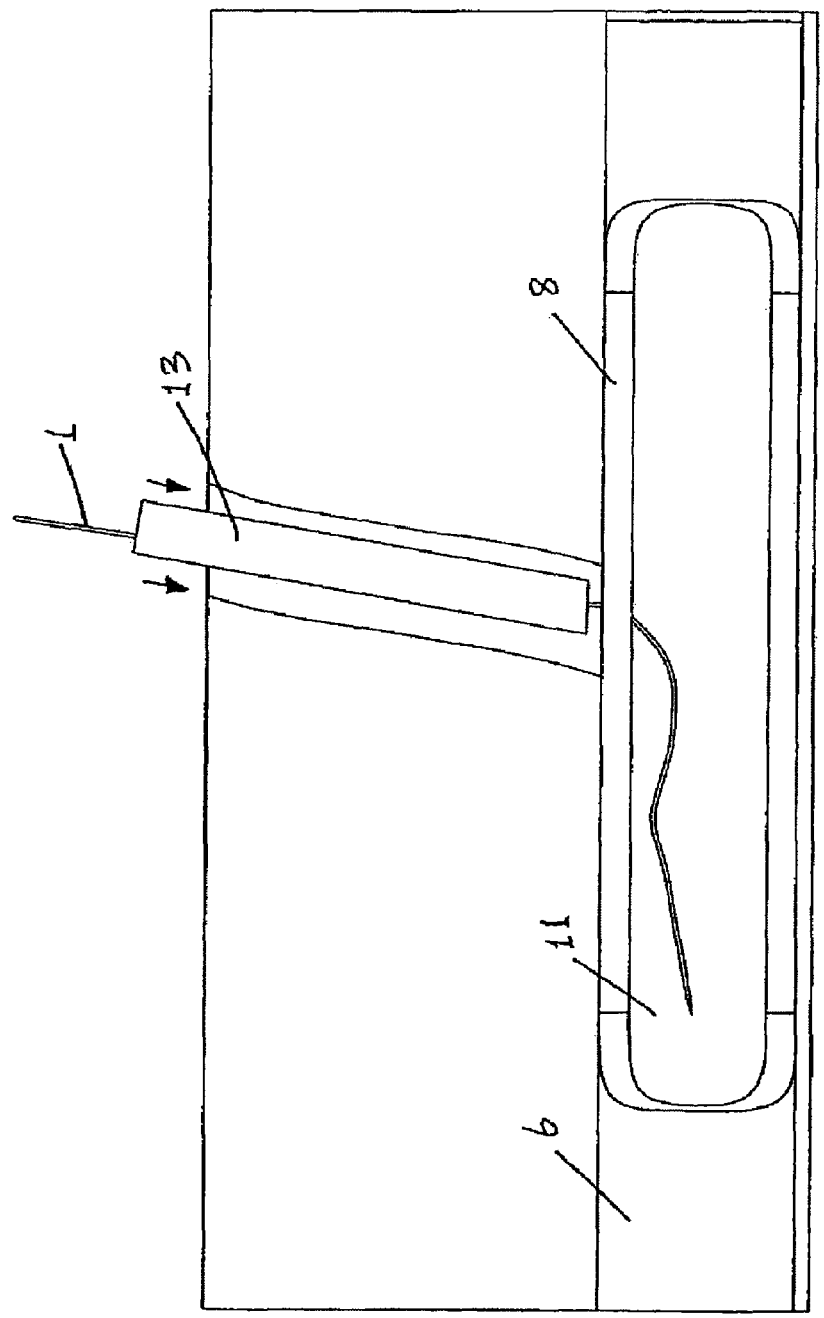
FIGS. 57 to 69 are partially cross-sectional, side views illustrating another method of accessing an interior of a body part according to the invention using the incising element of FIGS. 56(a) to 56(e)

The sequence of FIGS. 57 to 68 shows the following:

Step 1: The introducer sheath 13/cutting device 40 being guided over the engagement element 1 through the tissue channel to the outside wall 8 of the vessel 6 (FIG. 57).

Steps 2 & 3: The cutter 41 is activated and shown with a partial cut (FIG. 58) and a full incision (FIGS. 59 and 60) made through the vessel wall 8.

Step 4: Cutter 40 is removed from the introducer sheath 13 (FIG. 61).

Figure 62:
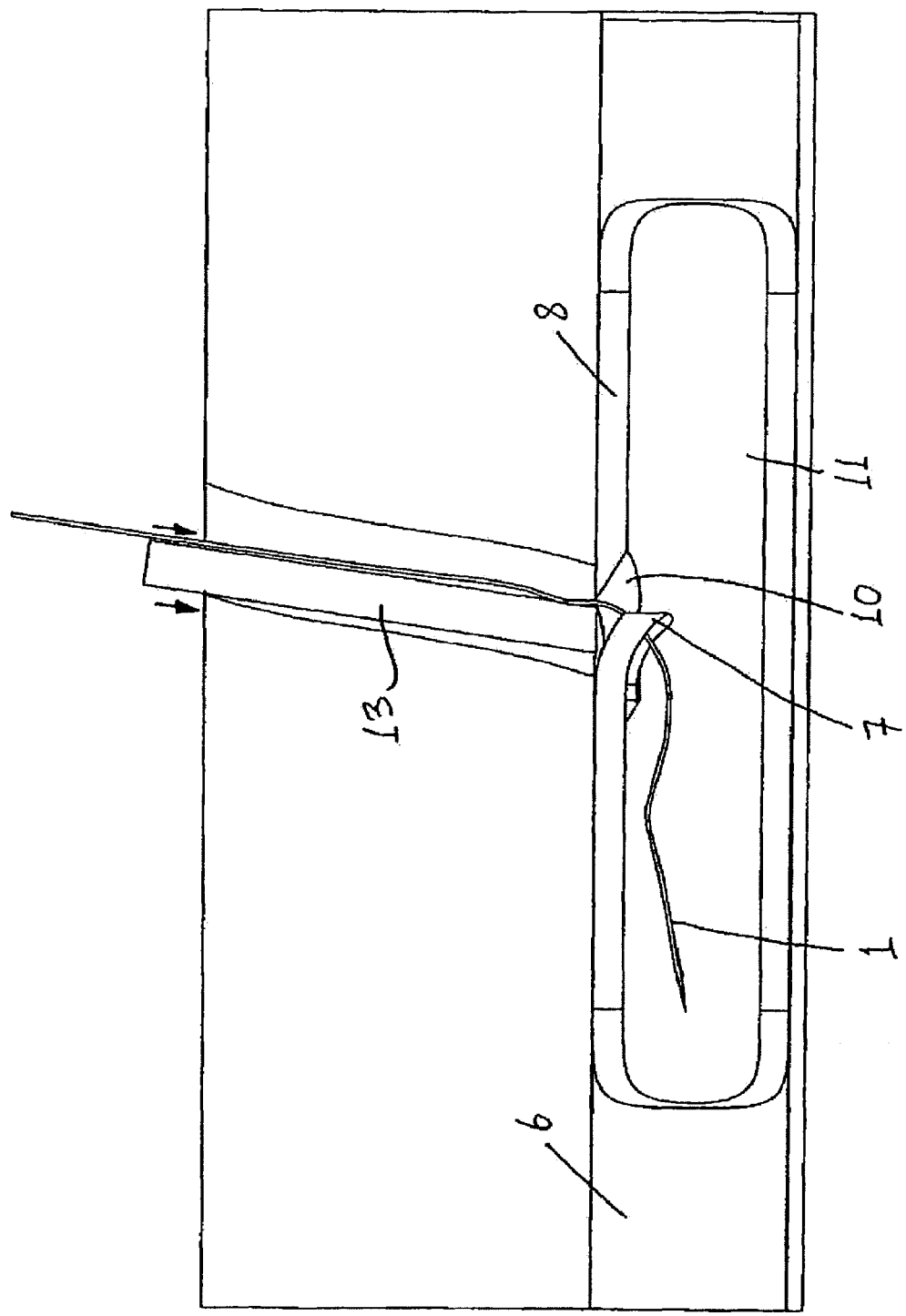

Step 5: The introducer sheath 13 is being pushed through the incision 9 and pushing the anchored tissue 7 out of its path (FIG. 62).

Figure 63:
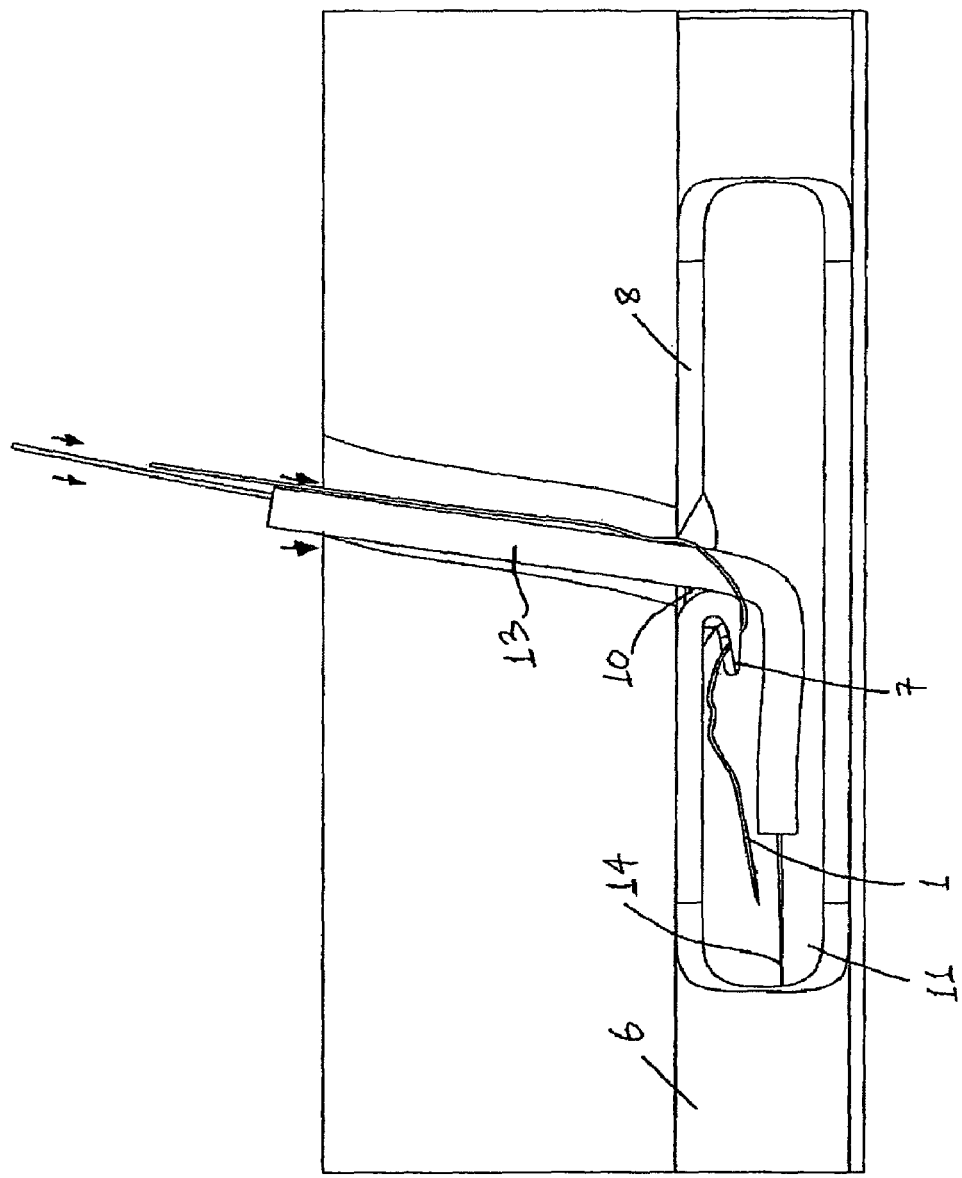
Figure 64:
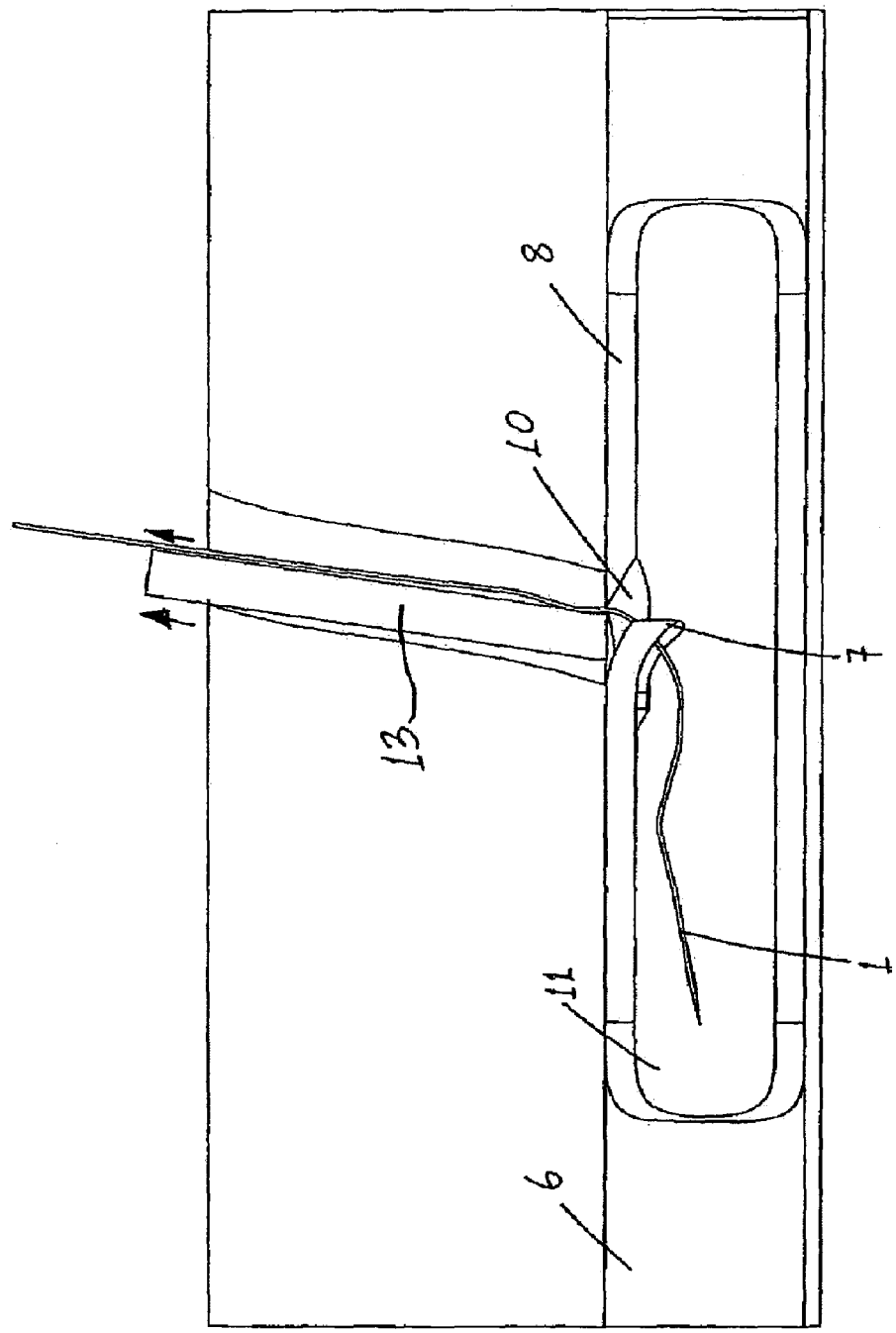

Step 6: The introducer sheath 13 is progressed into its final position in the vessel lumen 11 and the interventional procedure is completed (FIG. 63).

Figure 65:
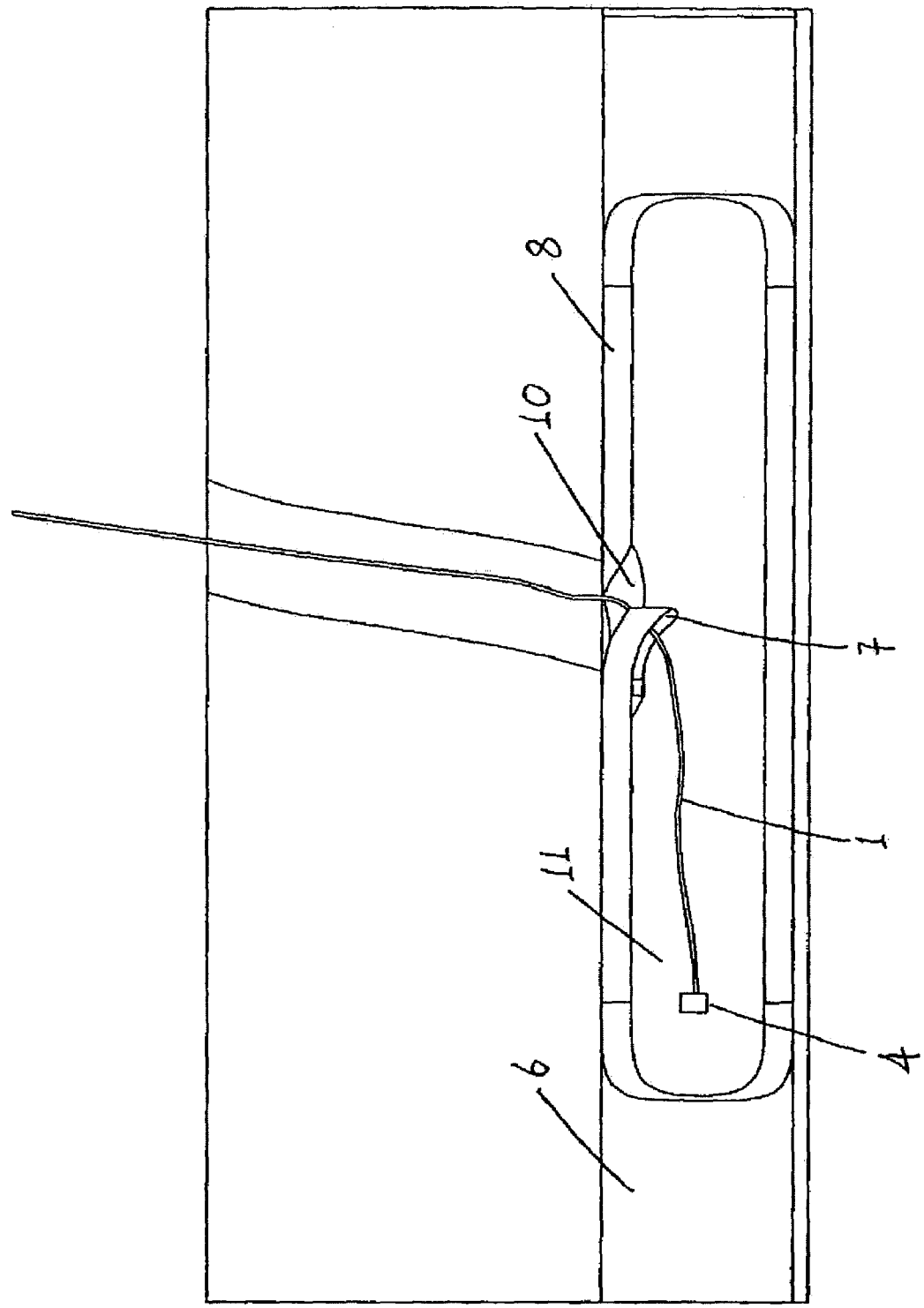

Steps 7 & 8: The introducer sheath 13 is withdrawn from the vessel 6 (FIG. 64) and the engagement element expandable element 4 is activated (FIG. 65).

Figure 66:
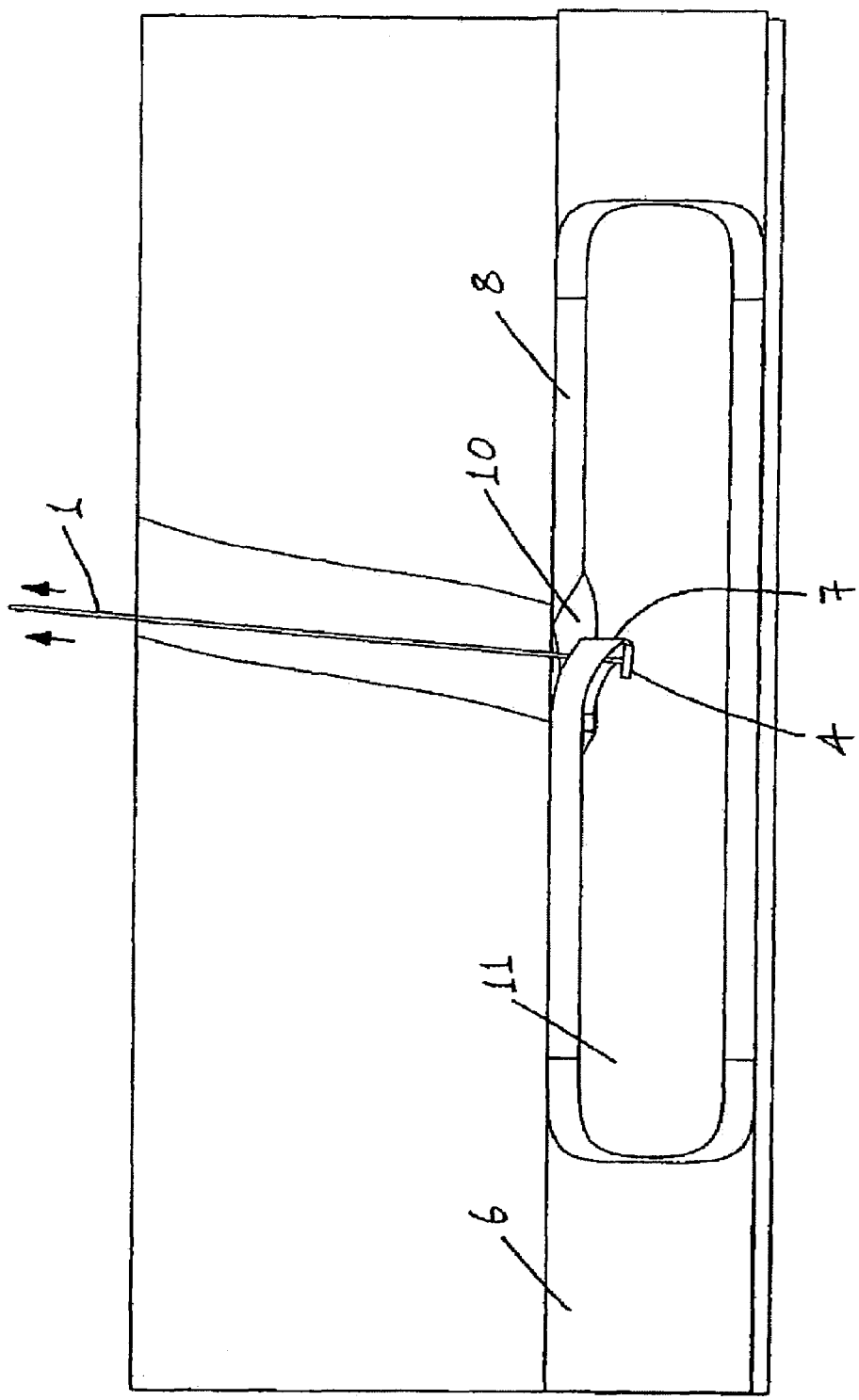
Figure 67:
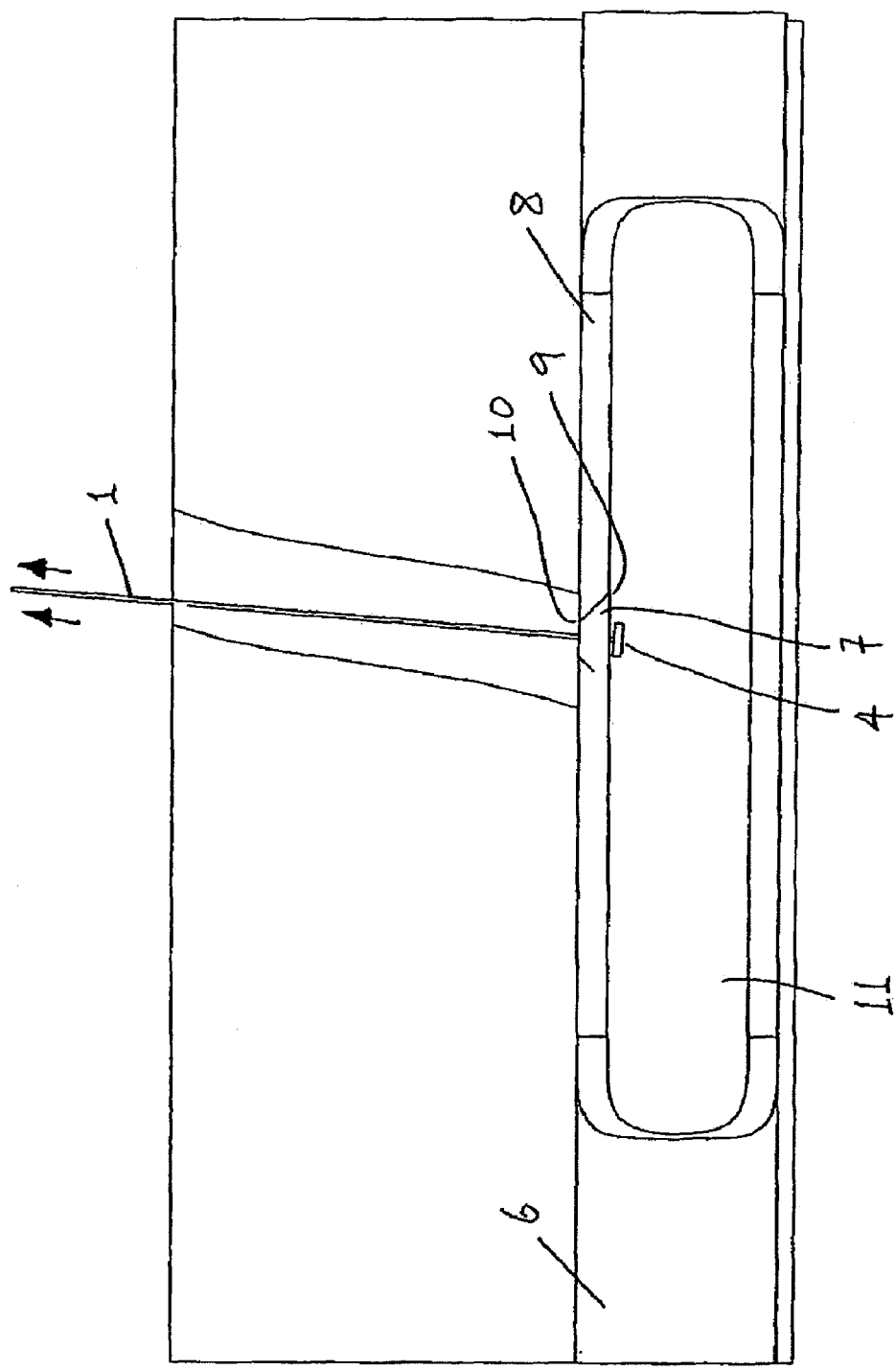

Steps 9 & 10: The engagement element 1 is withdrawn and begins to pull the flap 7 closed (FIGS. 66 and 67).

Figure 68:
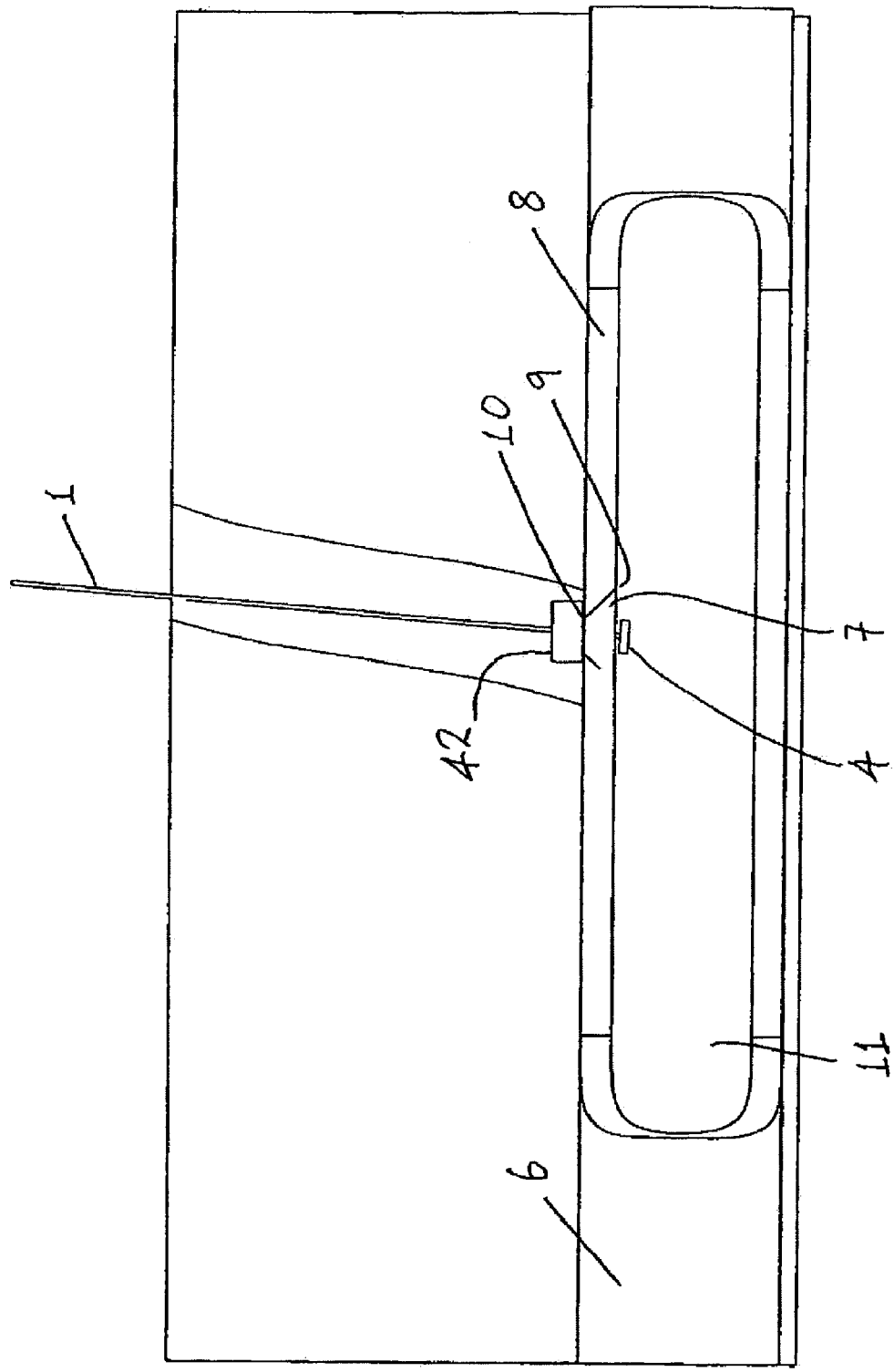

Step 11: The flap 7 is secured with an anchor device 42 on the outside of the vessel wall 8 (FIG. 68).

Figure 69:
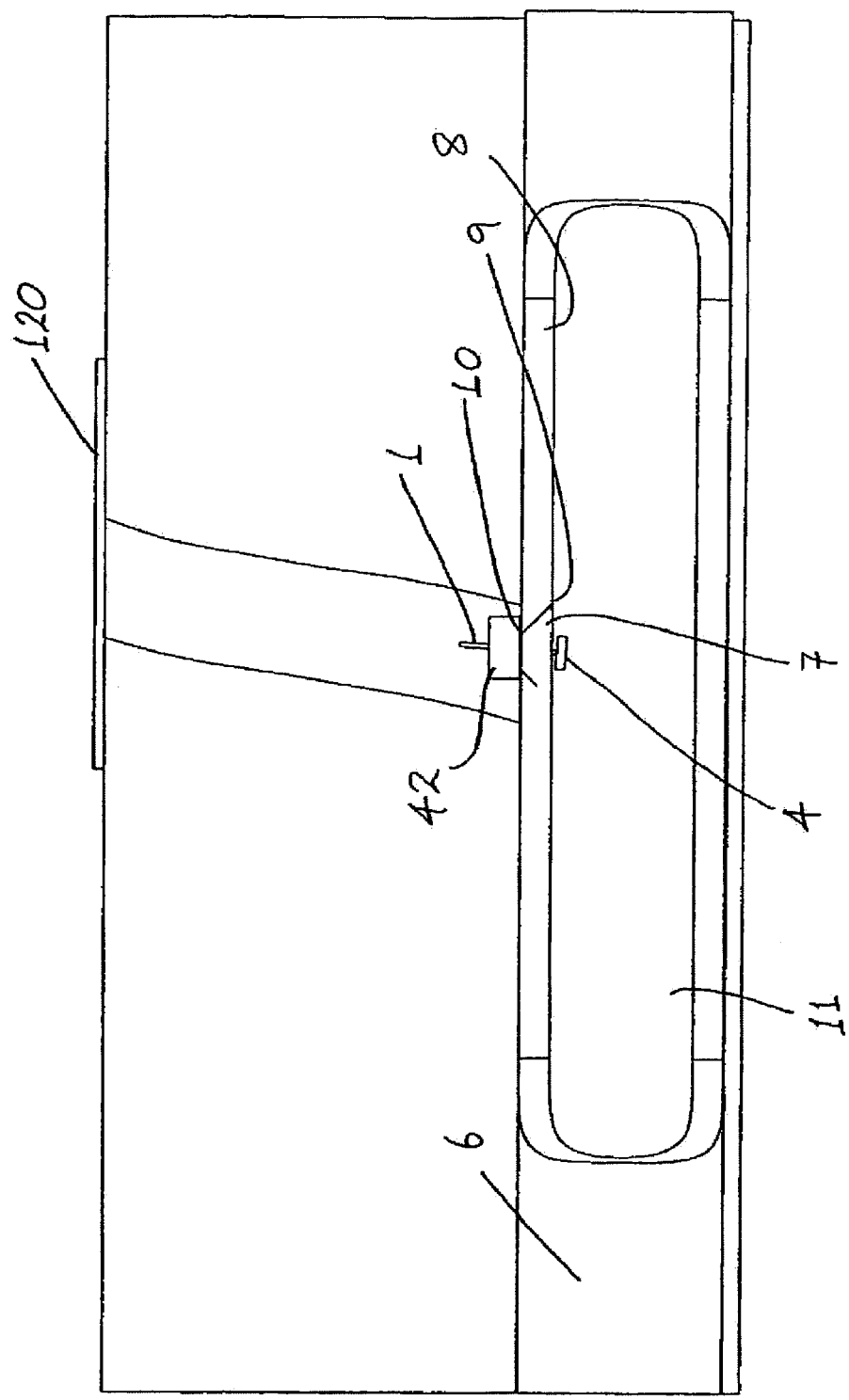

FIG. 69 illustrates the tissue tract closure step. At the conclusion of the procedure, either after the anchoring element 42 is in place in the bio absorbable system, or the engagement element 1 is ready for removal from the body, the tissue tract can be protected using an adhesive pad element 120 which can include some antibiotic and thrombogenic substances and may be biodegradable. When used in conjunction with the bioabsorbable engagements element 1, the engagement element 1 may be trimmed to below the skin surface and the adhesive pad 120 would be placed over the tissue tract opening to the skin, securing the site from contamination and promoting healing (FIG. 69).

The device of the invention may have a precise marking on it to clearly indicate the correct positioning of the cutting device 40 once it is butted up to the outside of the artery wall 8. Also, the direction of intended travel of the cutting blade 41 may be clearly marked on the device.

Referring to FIGS. 70 to 73 there is illustrated an interventional medical closure device 300 according to the invention. The device 300 comprises a closure element 301, a grasping element 302 for grasping the closure element 301, a guide element 303 for guiding passage of the grasping element 302, and a delivery element 304 for delivering the closure element 301 into an internal lumen 323 of a blood vessel 320.

The closure element 301 comprises a suture 305, a snap-fit engagement feature 306 at a proximal end of the suture 305, and an engagement foot 307 at a distal end of the suture 305. The engagement foot 307 may be made up of a bioabsorbable material, such as polyglycolic acid (PGA), polylactic acid (PLA), Polyethylene Glycol (PEG), polydioxanone bioabsorbable Polyurethane, or combinations or copolymers thereof. The suture 305 may be made up of a biodegradable polymer suture, such as polyglycolic acid (PGA), polylactic acid (PLA), polydioxanone, or combinations or copolymers thereof.

The grasping element 302 comprises a flexible, elongate member 308, a handle 309 at a proximal end of the elongate member 308, and a snap-fit engagement feature 310 at a distal end of the elongate member 308. The engagement feature 310 of the grasping element 302 is inter-engageable with the engagement feature 306 of the closure element 301 in a snap-fit manner to enable the grasping element 302 to grasp the closure element 301. The grasping element 302 may be made of a superelastic material, such as nitinol, or may be made from stainless steel, or a kink resistant stiff polymer, such as PEEK.

The delivery element 304 comprises a main body portion 313, a distal nose 314 at a distal end of the main body portion 313, and a proximal handle 315 at a proximal end of the main body portion 313.

The distal nose 314 is rotatably movable relative to the main body portion 313 in a hinging manner. The distal nose 314 defines a reception space for carrying the engagement foot 307 of the closure element 301.

Figures 72, 73:
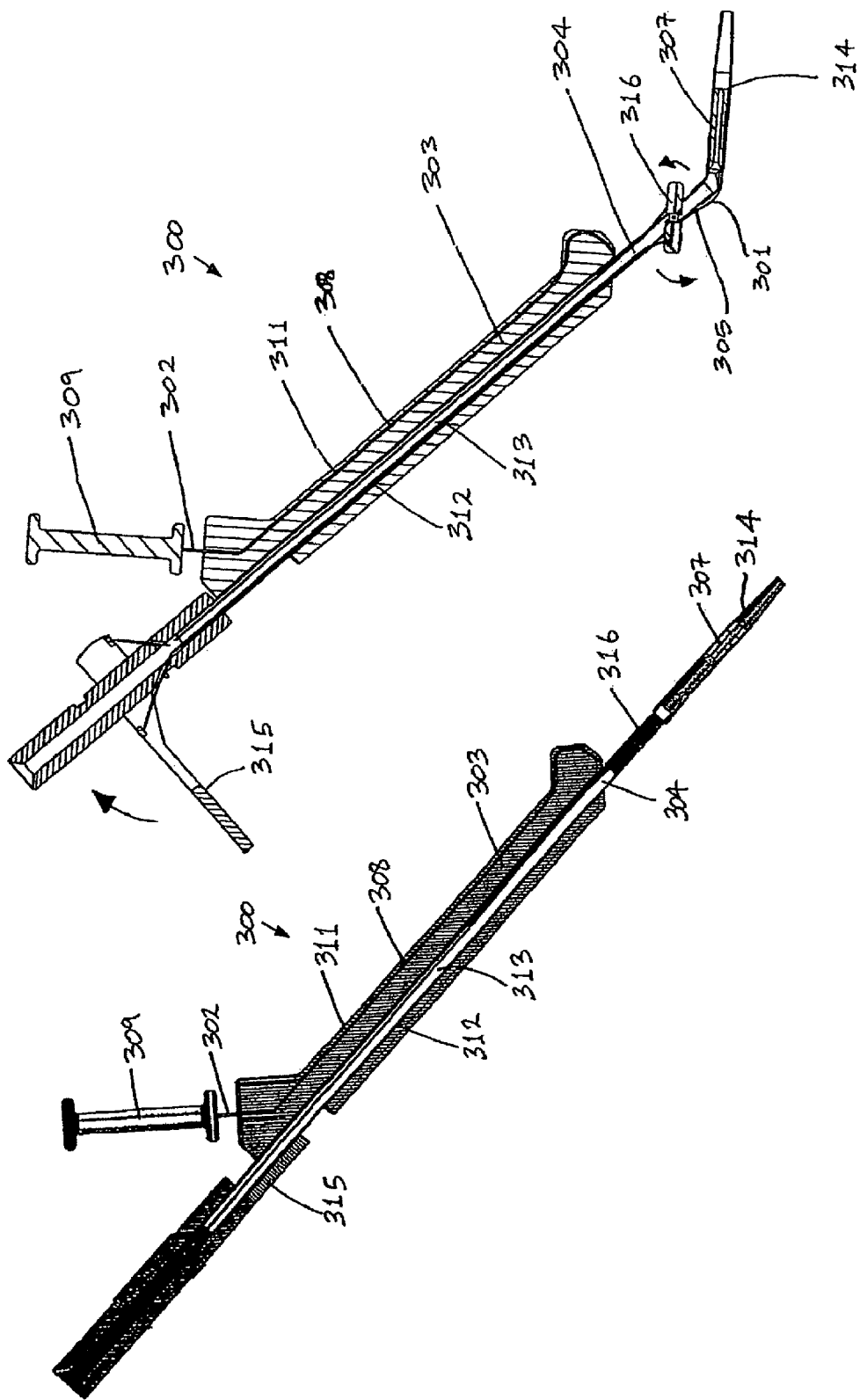
FIGS. 72 and 73 are cross-sectional, side views of the device of FIGS. 70 and 71.
Figures 82, 83:
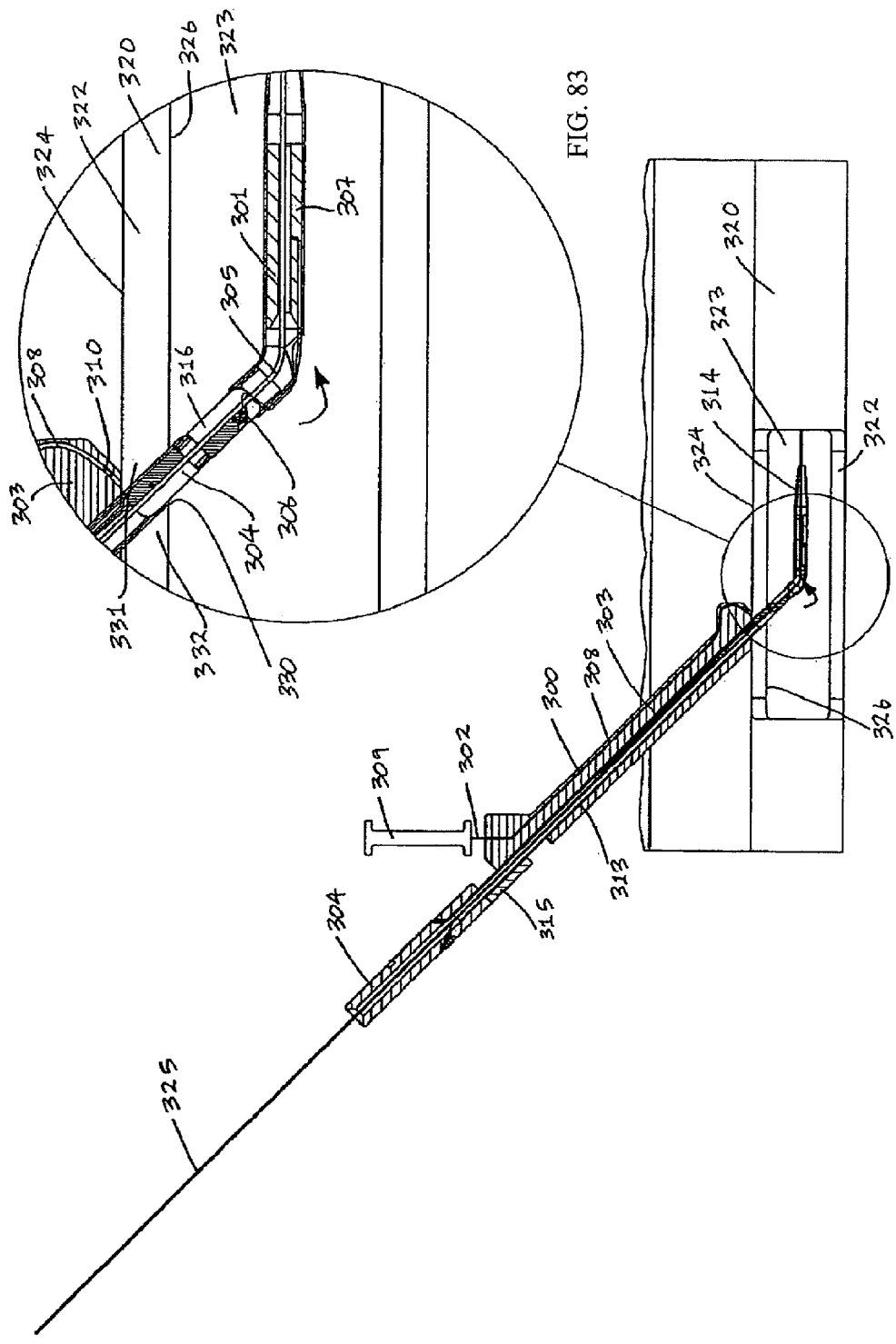

The delivery element 304 also comprises an engagement foot 316 which is rotatably movable relative to the main body portion 313 in a hinging manner between a low-profile delivery configuration (FIG. 72) and a protruding engagement configuration (FIG. 73). The proximal handle 315 is rotatably movable relative to the main body portion 313 in a hinging manner to control movement of the engagement foot 316. The engagement foot 316 of the delivery element 304 carries the engagement feature 306 of the closure element 301.

The guide element 303 comprises a first lumen 311 extending therethrough, through which the grasping element 302 may pass. The guide element 303 also comprises a second lumen 312 extending therethrough, through which the main body portion 313 of the delivery element 304 may extend.

The device 300 may be employed to perform an interventional procedure on a blood vessel 320 according to the invention, as illustrated in FIGS. 74 to 121. In this case the blood is flowing through the blood vessel 320 in the direction of arrow E in FIGS. 74 and 75. In use, a tubular needle 321 is extended through the wall 322 of the blood vessel 320 from the external surface 324 of the blood vessel 320 to the internal lumen 323 of the blood vessel 320 (FIG. 74). In this manner a puncture opening 330 is created through the blood vessel wall 322, with a first part 331 of the blood vessel wall 322 on a first side of the opening 330, and a second part 332 of the blood vessel wall 322 on a second side of the opening 330. As illustrated in FIG. 75, the longitudinal axis B-B of the opening 330 subtends an acute angle, in this case approximately 45°, with the longitudinal axis of the internal lumen 323 of the blood vessel 320. A guidewire 325 is introduced through the needle 321 into the internal lumen 323 of the blood vessel 320 (FIG. 76), and the needle 321 is then removed (FIG. 78).

Figures 84, 85:
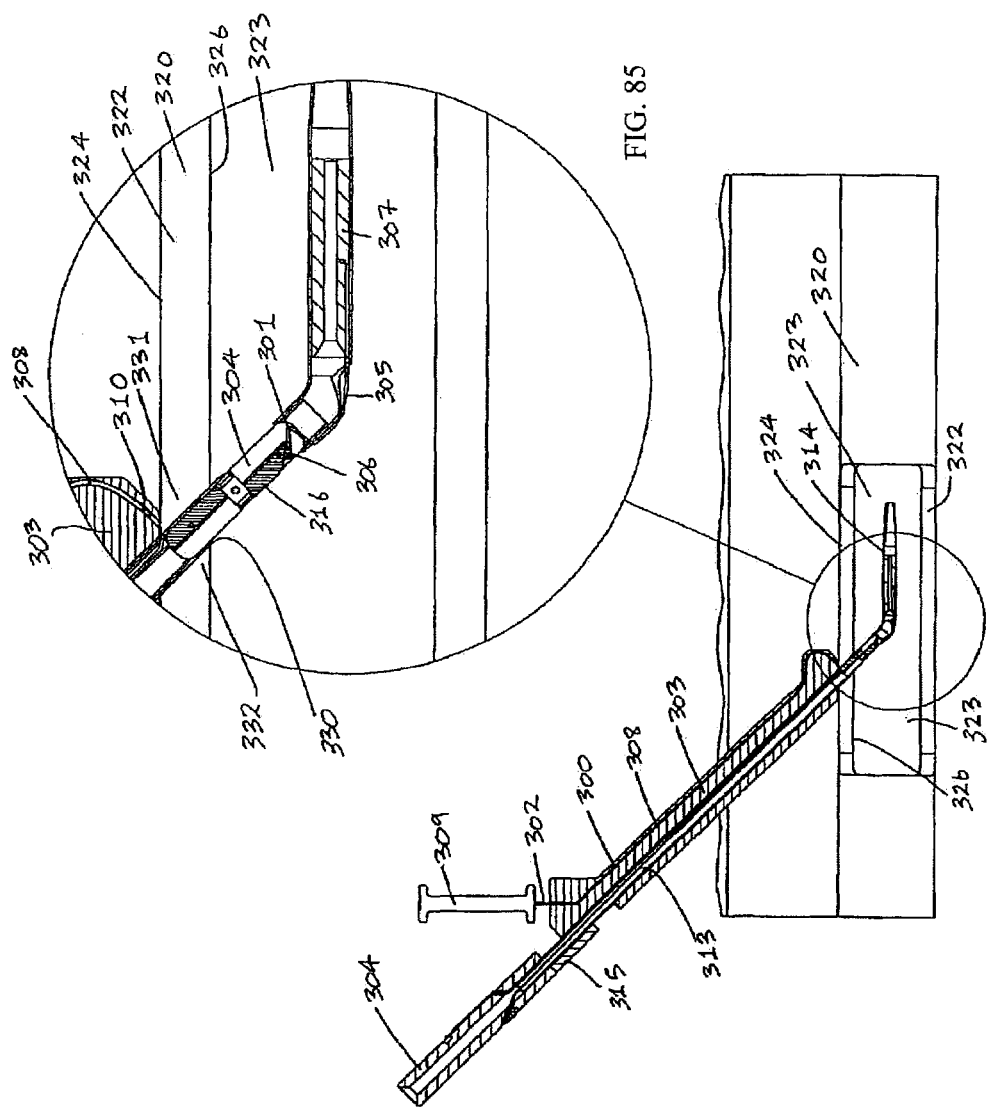
Figures 94, 95:
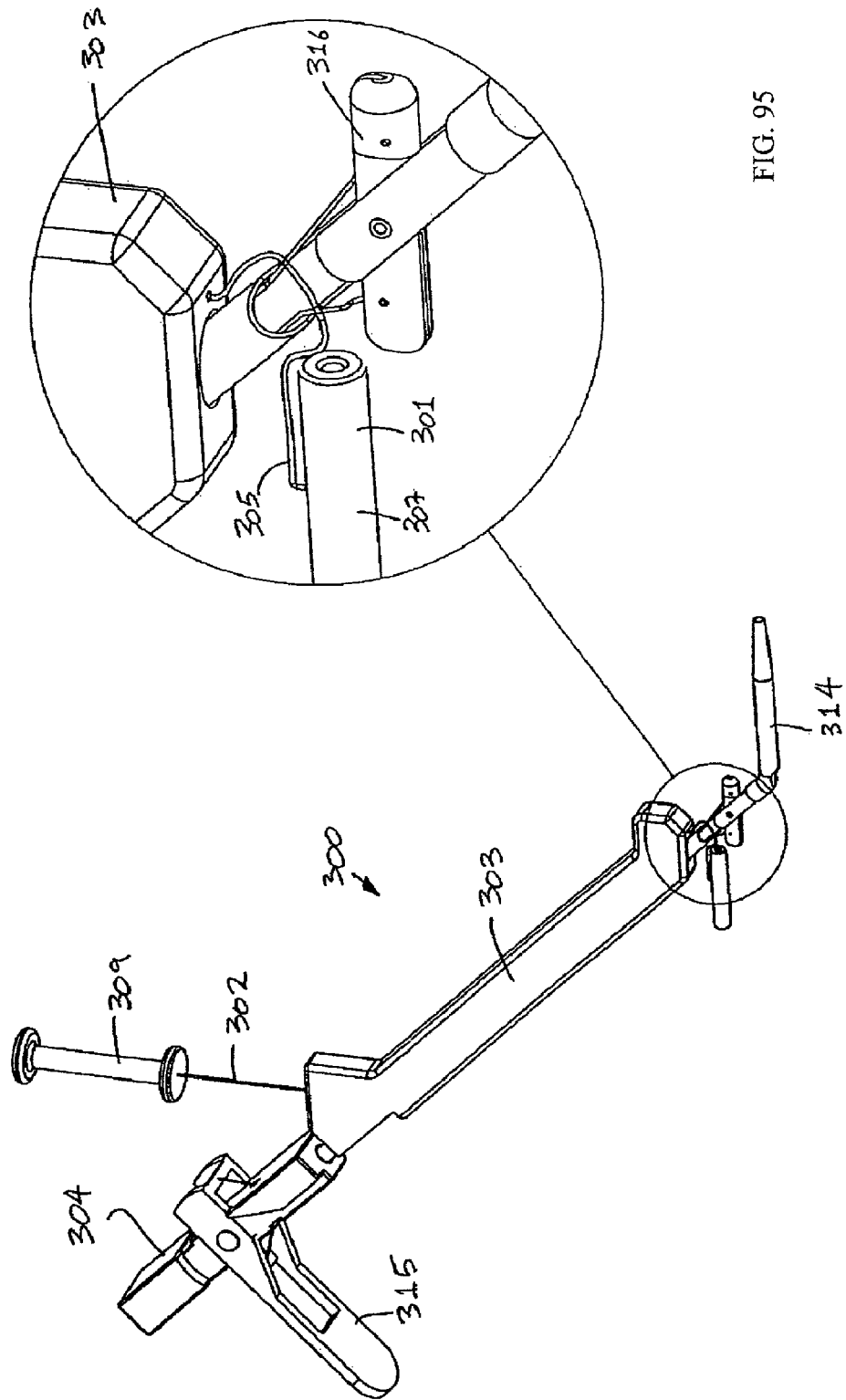
FIG. 94 is a perspective view of the device of FIG. 70 and 71 in the step illustrated in FIGS. 92 and 93.
FIG. 95 is an enlarged, perspective view of a part of the device of FIG. 94.

The device 300 is threaded over the guidewire 325, with the distal nose 314 of the delivery element 304 arranged in-line with the main body portion 313, and with the engagement foot 316 of the delivery element 304 in the delivery configuration. The engagement foot 304 of the closure element 301 is carried by the distal nose 314 of the delivery element 304, and the engagement feature 306 of the closure element 301 is carried by the engagement foot 316 of the delivery element 304. The device 300 is advanced over the guidewire 325 to dilate the opening 330 until the distal nose 314 is within the internal lumen 323 of the blood vessel 320 (FIG. 80). In this manner the closure element 301 is inserted through the opening 330 into the internal lumen 323 of the blood vessel 320. The distal nose 314 of the delivery element 304 is rotated relative to the main body portion 313 (FIG. 82), and the guidewire 325 is removed (FIG. 84). The distal nose 314 may be made of a flexible piece of tubing. The distal nose 314 may be rotated relative to the main body potion 313 by means of the flexible tubing deforming upon engagement of the distal nose 314 with the internal surface 326 of the blood vessel 320.

The engagement foot 316 of the delivery element 304 is rotated relative to the main body portion 313 from the delivery configuration to the engagement configuration by rotating the proximal handle 315 relative to the main body portion 313 (FIG. 86). The delivery element 304 is slid proximally through the second lumen 312 of the guide element 303, while the portion of the guide element 303 remains substantially fixed, until the engagement foot 316 of the delivery element 304 engages the internal surface 326 of the blood vessel 320 (FIG. 88). By engaging the foot 316 with the internal surface 326, this maintains the position of the closure element 301 substantially fixed within the internal lumen 323 of the blood vessel 320 prior to grasping.

The handle 309 of the grasping element 302 is pushed distally while the position of the guide element 303 remains substantially fixed, which causes the engagement feature 310 of the grasping element 302 to pass through the first part 331 of the blood vessel wall 322, across the opening 330, through the second part 332 of the blood vessel wall 322, and into engagement with the engagement feature 306 of the closure element 301 (FIG. 90). In this manner the grasping element 302 grasps the closure element 301 within the internal lumen 323.

As illustrated in FIG. 91, the axis C-C along which the engagement feature 310 of the grasping element 302 passes subtends an acute angle, in one embodiment, in the range of from 5° to 65°, in one embodiment, in the range of from 15° to 55°, and in this case approximately 30°, with the longitudinal axis of the internal lumen 323 of the blood vessel 320. The axis C-C subtends an angle a in the range of from 70° to 130°, in one embodiment, 80° to 120°, and in this case approximately 105° with the longitudinal axis B-B of the opening 330. FIG. 91 illustrates a transverse axis D-D of the internal lumen 323 which extends perpendicular to the longitudinal axis of the internal lumen 323 and through the point of intersection of the axis B-B and the axis C-C. As illustrated in FIG. 91, the intersection point of the axis B-B with the external surface 324 of the blood vessel 320 is on one side of the axis D-D, and the intersection point of the axis C-C with the external surface 324 of the blood vessel 320 is on the opposite side of the axis D-D. Thus the axis B-B effectively extends in an opposite direction to axis C-C. In this case the axis C-C extends in the direction of blood flow E, and the axis B-B extends in the opposite direction to blood flow E.

Figures 96, 97:
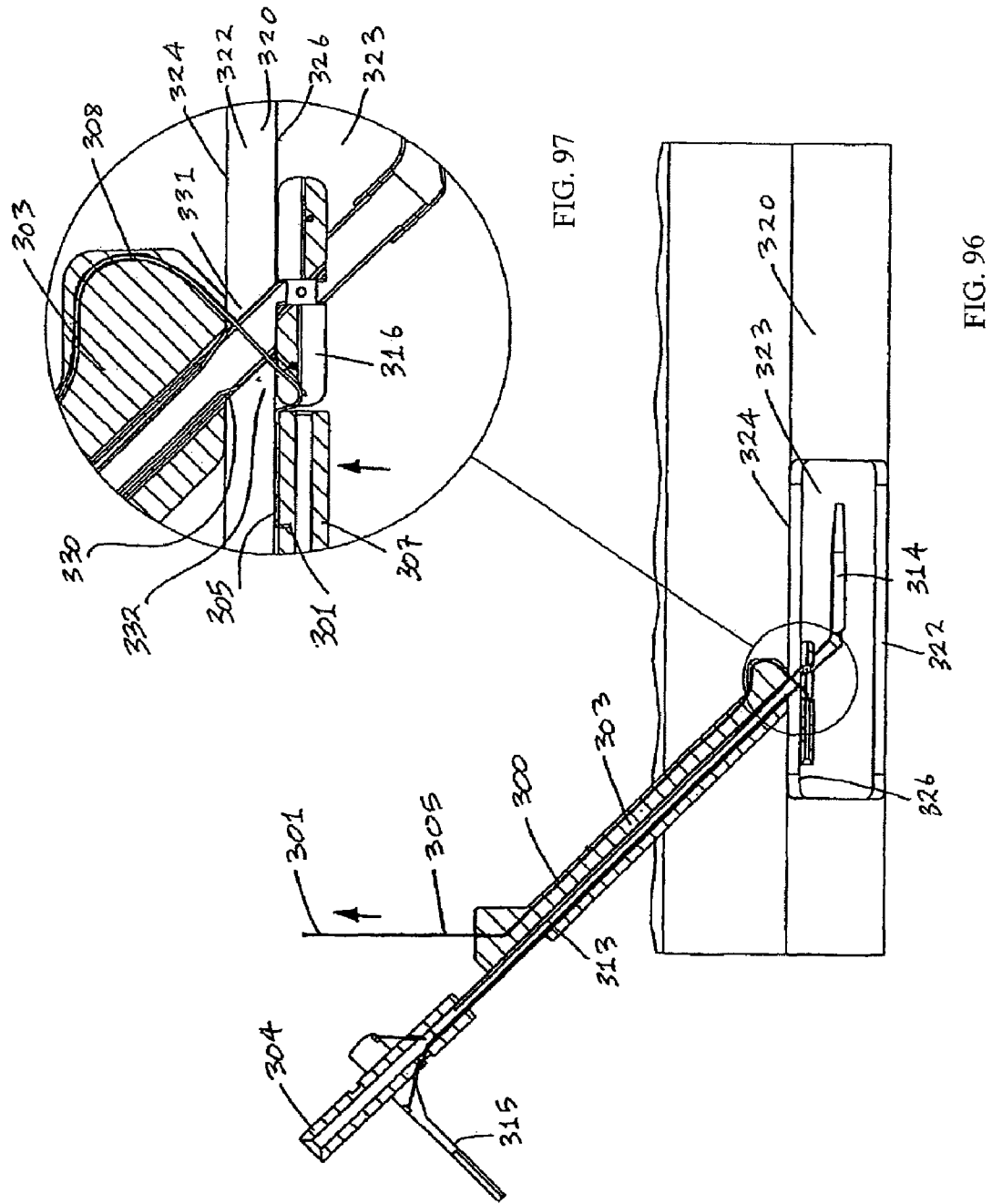

The handle 309 of the grasping element 302 is then pulled proximally while the position of the guide element 303 remains substantially fixed, which causes part of the closure element 301 to be retracted through the second part 332 of the blood vessel wall 322, across the opening 330, through the first part 331 of the blood vessel wall 322, and into the first lumen 311 of the guide element 303 (FIG. 92). The closure element 301 is retracted along the axis C-C. Pulling of the handle 309 of the grasping element 302 proximally also causes the engagement foot 307 of the closure element 301 to be released from the distal nose 314 (FIG. 92). The handle 309 of the grasping element 302 continues to be pulled proximally until the engagement foot 307 of the closure element 301 engages the internal surface 326 of the blood vessel 320 (FIG. 96).

Figures 106, 107:
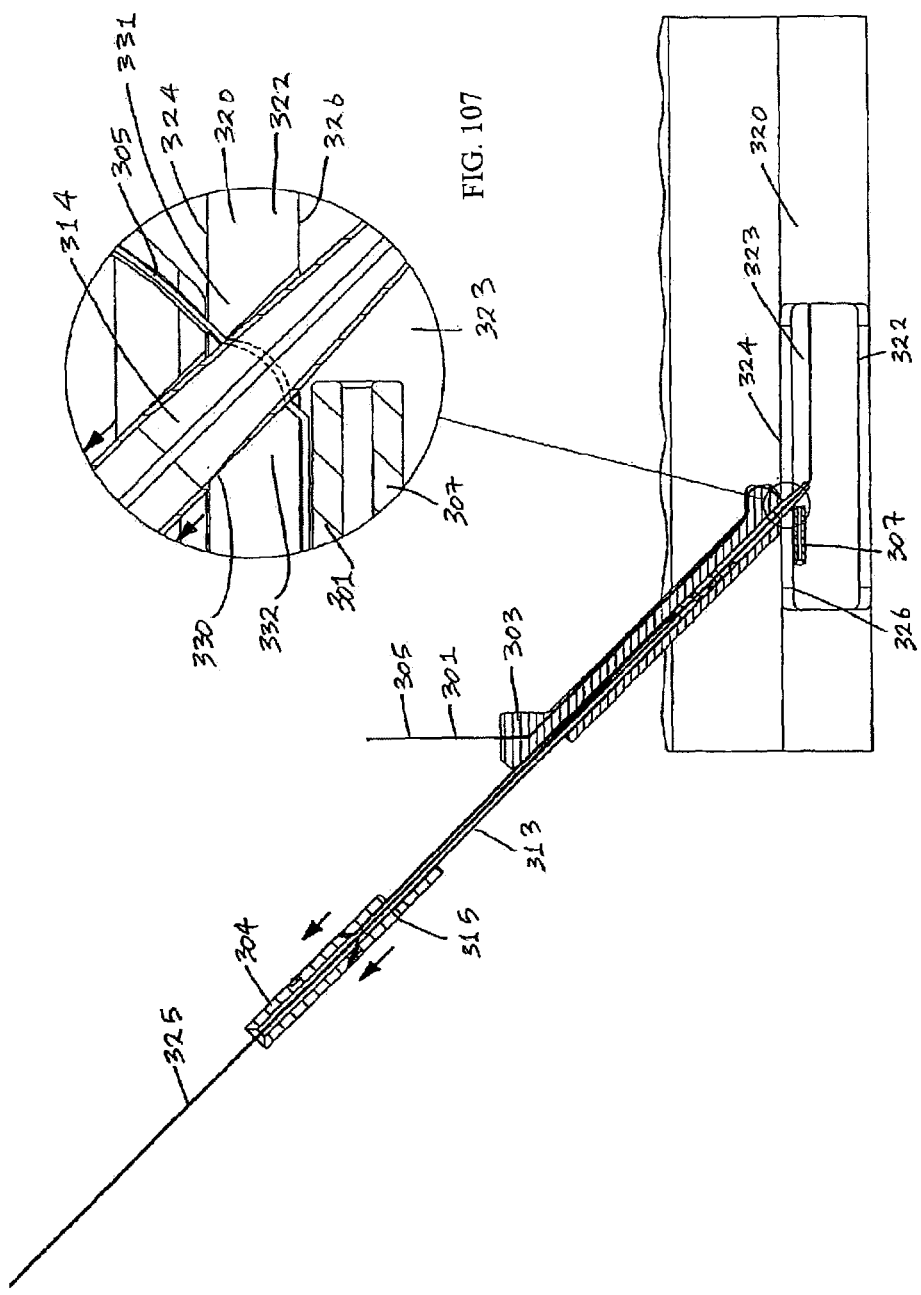

The engagement foot 316 of the delivery element 304 is rotated relative to the main body portion 313 from the engagement configuration to the delivery configuration by rotating the handle 315 relative to the main body portion 313 (FIG. 98), and the guidewire 325 is reintroduced into the internal lumen 323 of the blood vessel 320 by threading through the device 300 (FIG. 100). As illustrated in FIGS. 102 to 105, the suture 305 extends across a slot 360 in the hypotube main body portion 313. By rotating the hypotube main body portion 313 through 90 degrees, this will push the suture 305 out of the slot 360, thus allowing the delivery element 304 to be removed (FIG. 105). The distal nose 314 of the delivery element 304 is rotated relative to the main body portion 313 until the distal nose 314 is in-line with the main body portion 313, and the delivery element 304 is removed from the internal lumen 323 of the blood vessel 320 (FIG. 106).

The guide element 303 and the grasping element 302 are also removed, leaving the guidewire 325 extending through the opening 330 into the internal lumen 323 of the blood vessel 320 and the suture 305 extending through the blood vessel wall 322 into the internal lumen 323 (FIG. 108).

An introducer sheath 340 may be threaded over the guidewire 325 and advanced through the opening 330 to dilate the opening 330, and into the internal lumen 323 of the blood vessel 320 (FIG. 110). One or more medical devices, such as guidewires, delivery catheters, angioplasty catheters, retrieval catheters, diagnostic catheters, may be delivered through the introducer sheath 340 in the opening 330 into the internal lumen 323 of the blood vessel 320 to perform one or more interventional procedures within the internal lumen 323 of the blood vessel 320. After completion of the interventional procedures, the introducer sheath 340 and the guidewire 325 are removed.

Figures 115, 116, 117:
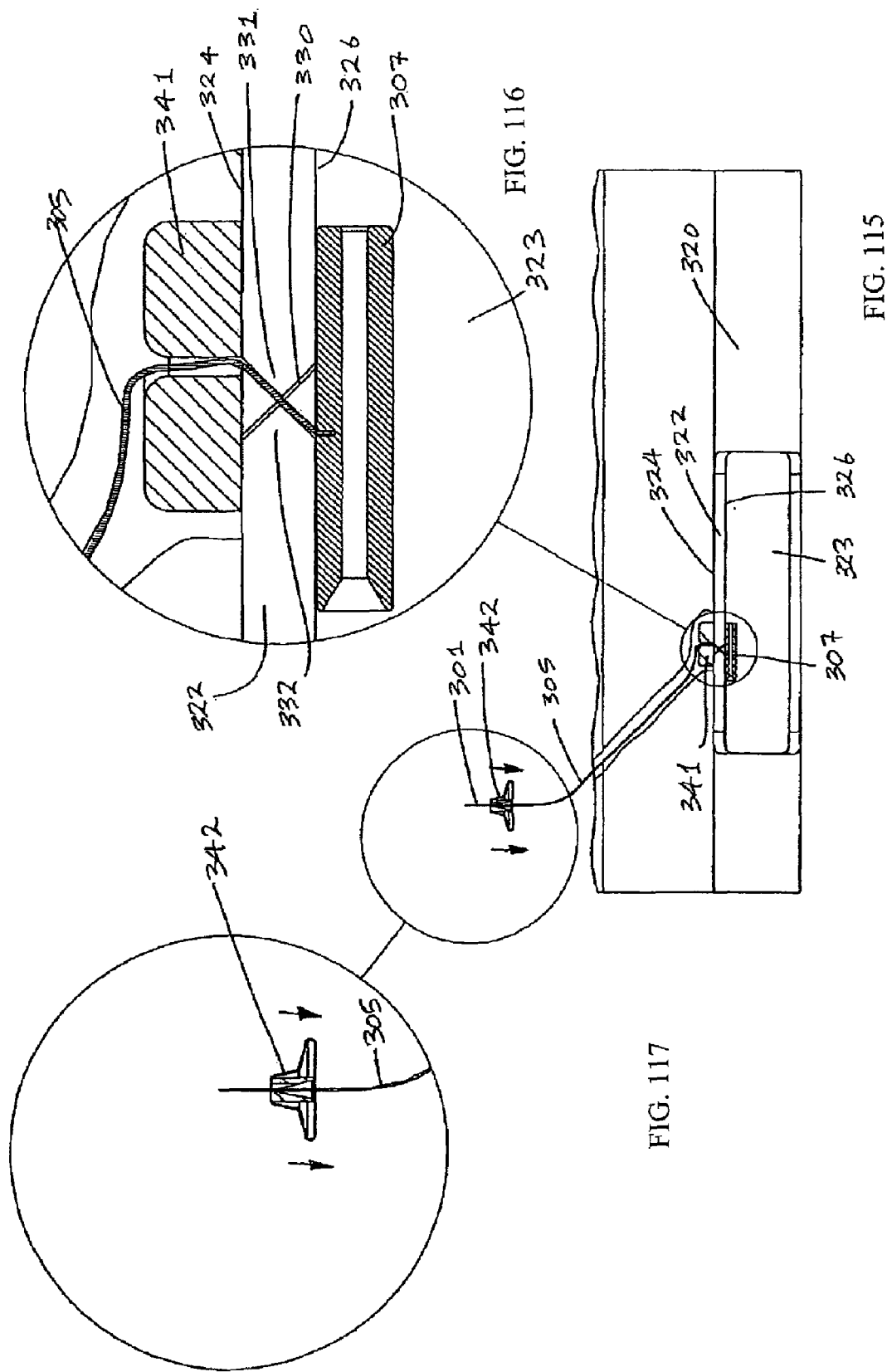
Figures 120, 121:
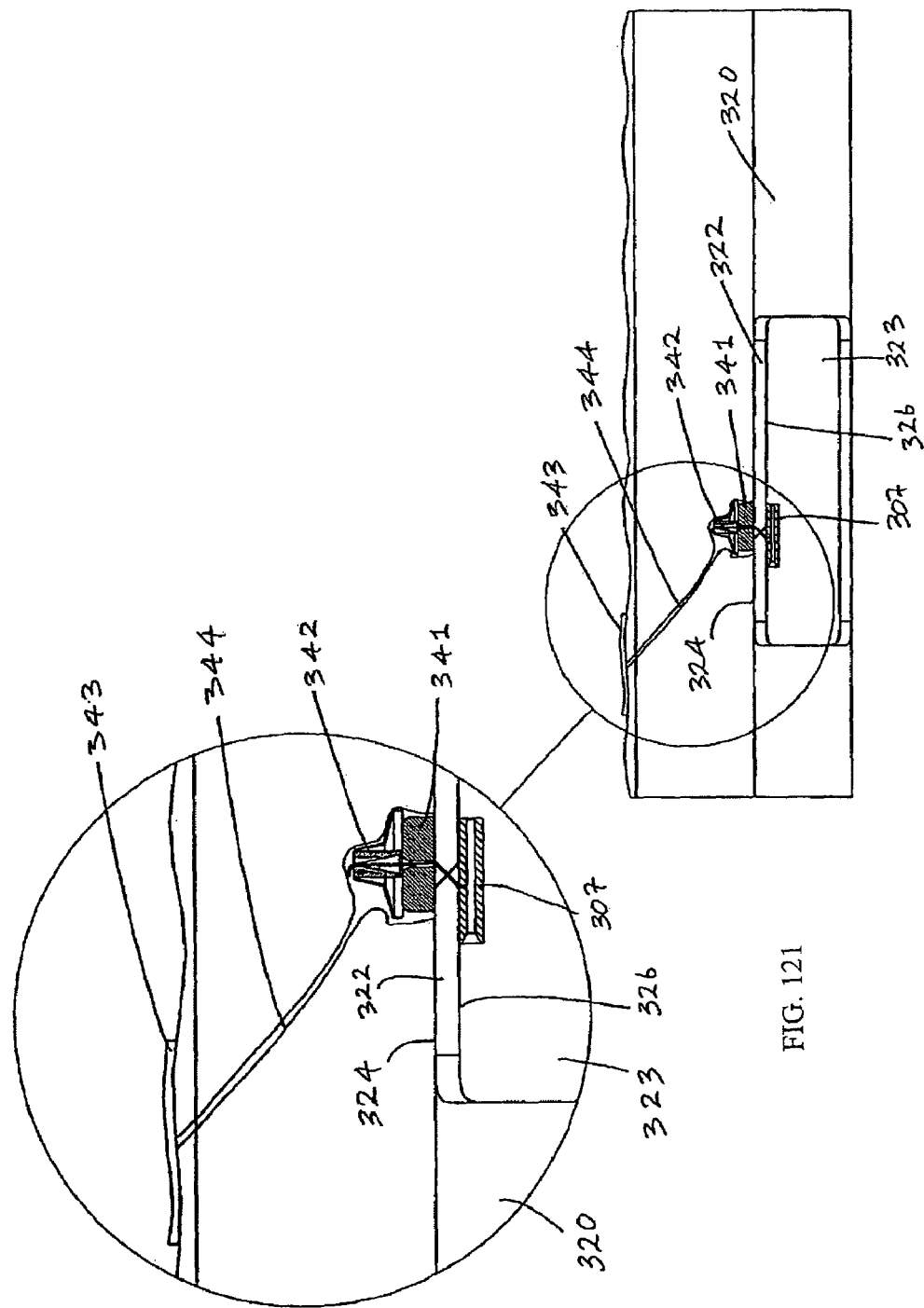
Figures 122, 123:
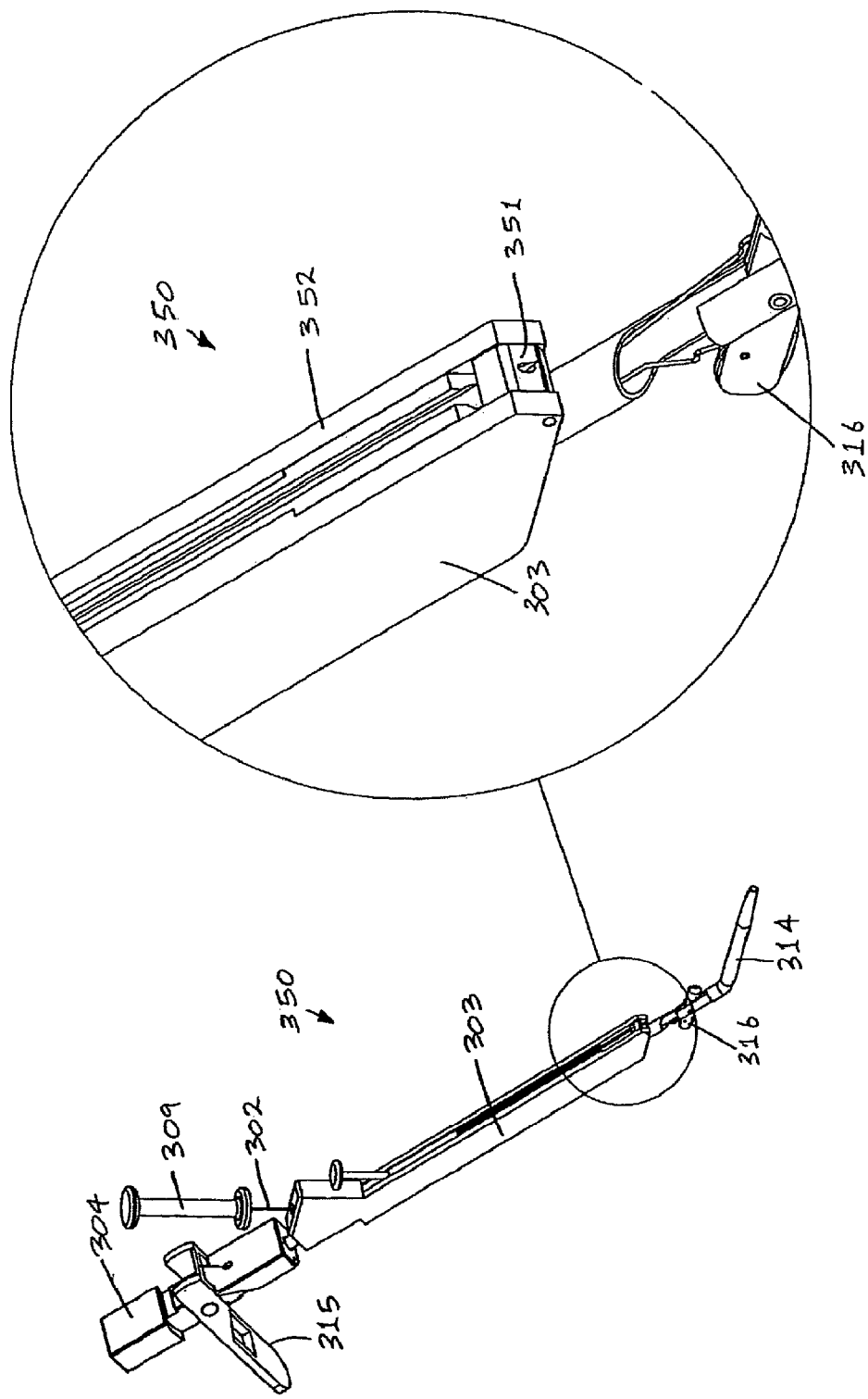
FIG. 122 is a perspective view of the another interventional medical closure device according to the invention in a delivery configuration.
FIG. 123 is an enlarged, perspective view of a part of the device of FIG. 122.
Figure 125:
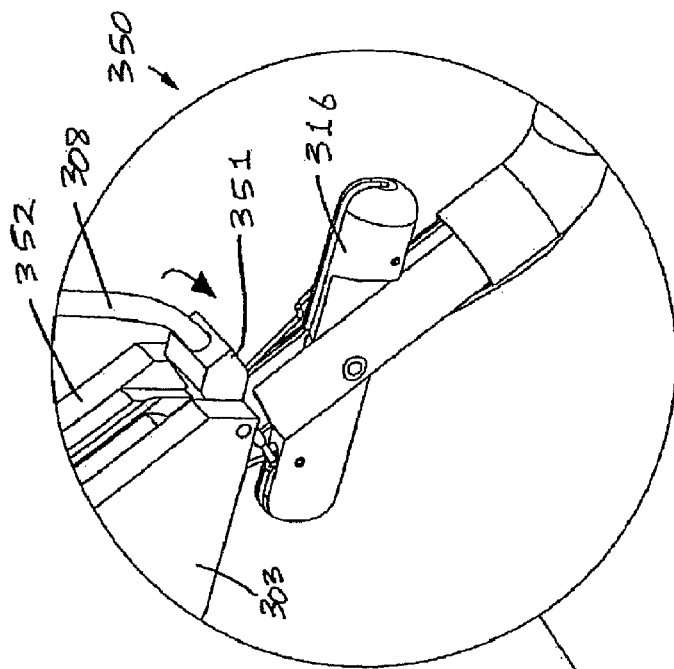
FIGS. 124 and 125 are views similar to FIGS. 122 and 123 of the device of FIG. 122 in a guiding configuration.

The suture 305 is pulled proximally until the engagement foot 307 of the closure element 301 engages the internal surface 326 of the blood vessel 320 on the first side of the opening 330 and on the second side of the opening 330. An external plug 341 is then threaded over the suture 305 and advanced distally into engagement with the external surface 324 of the blood vessel 320 on the first side of the opening 330 and on the second side of the opening 330 (FIG. 112). In this manner, the engagement foot 307 of the closure element 301 exerts a compressive force on the internal surface 326 of the blood vessel 320, and the plug 341 exerts a compressive force on the external surface 324 of the blood vessel 320. This compression of the blood vessel wall 322 on both sides of the opening 330 assists in closure of the opening 330. An external anchor 342 is threaded over the suture 305 and advanced distally into engagement with the plug 341 to anchor the plug 341 in position engaging the external surface 324 of the blood vessel 320 (FIGS. 115 and 118). A protective element 343 is mounted at the proximal end of the tissue tract 344 (FIG. 120).

The external plug 341 may be made of PGA, PLA, collagen, or PEG.

The tubular needle type cutter 321 creates the incision 330 for delivery of the securement feature 301 across this incision 330. The tubular needle 321 is non-coring and achieves a slit 330 and allows for easy delivery of a guidewire 325 and minimal blood loss during the setting of the securement feature 301.

The securement feature 301 may be delivered across the incision 330 through a slot either in the needle 321 or a subsequent tube that is placed through the incision 330.

An important aspect of the invention is the control of the distance from the internal lumen 323 of the artery 320 to the point at which the securement feature 301 crosses the incision 330. The intravascular positioning foot 316 is a means of controlling this distance accurately. This may be an integrated part of the tubular needle 321 or once the incision 330 is made, the tube 304 which contains the foot 316 is delivered over the introducer guidewire 325.

The securement element delivery device 303 may be slid over the positioning foot 304 and locked into position; the securement element 301 may be delivered across the incision 330 through a slot/hole in the positioning foot tube 304.

The device 304 is removed and the interventional procedure is carried out. The suture 305 is moved aside as the dilator/introducer sheath 340 is delivered through the arteriotomy 330.

The incision 330 is sealed by pulling on the suture 305 and then advancing and locking into position the bioabsorbable element 341 which has haemostatic properties.

This extravascular component 341 may be in the form of a soft fibre mesh and the compression could be achieved by the extra bioabsorbable component 342 which is rigid and has a feature which locks onto the suture 305.

The device 300 may involve the needle 310 that crosses the cut artery 320 and picks up the suture 305 that is stored in the flexible tube that is already within the artery 323. The advantages of this approach are lower force may be required to cross the incision 330 as the securement element 301 is already in the vessel 323 larger securement feature 301 may be used with more design flexibility smaller profile crossing incision 330 gives greater accuracy controlling the crossover distance.

A possible way of picking up the suture 305 and drawing it back may be to mount a coiled spring 306 on the end of the suture 305 and have a feature 310 on the needle 302 which will lock into this spring 306.

Figures 70, 71:
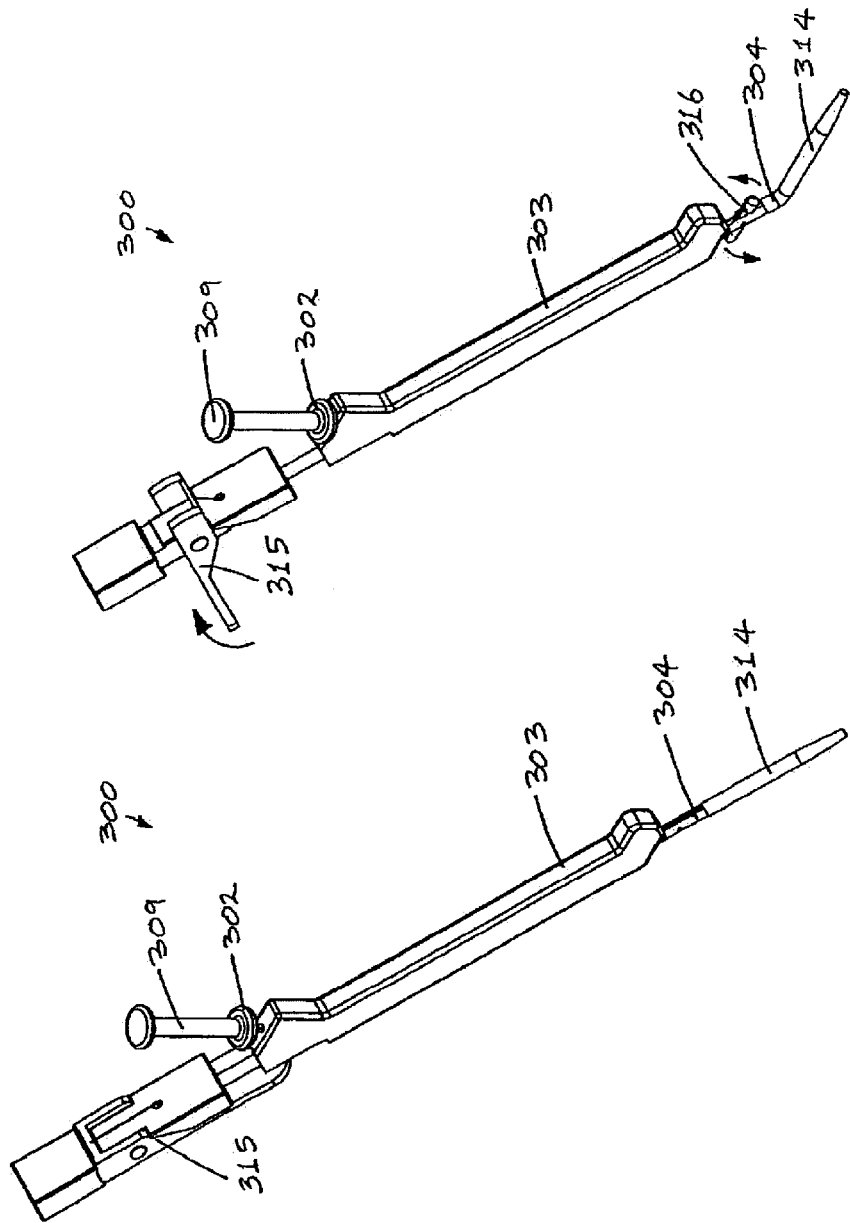
FIGS. 70 and 71 are perspective views of an interventional medical closure device according to the invention.

In FIGS. 122 to 127 there is illustrated another interventional medical closure device 350 according to the invention, which is similar to the device 300 of FIGS. 70 to 121, and similar elements in FIGS. 122 to 127 are assigned the same reference numerals.

Figure 124:
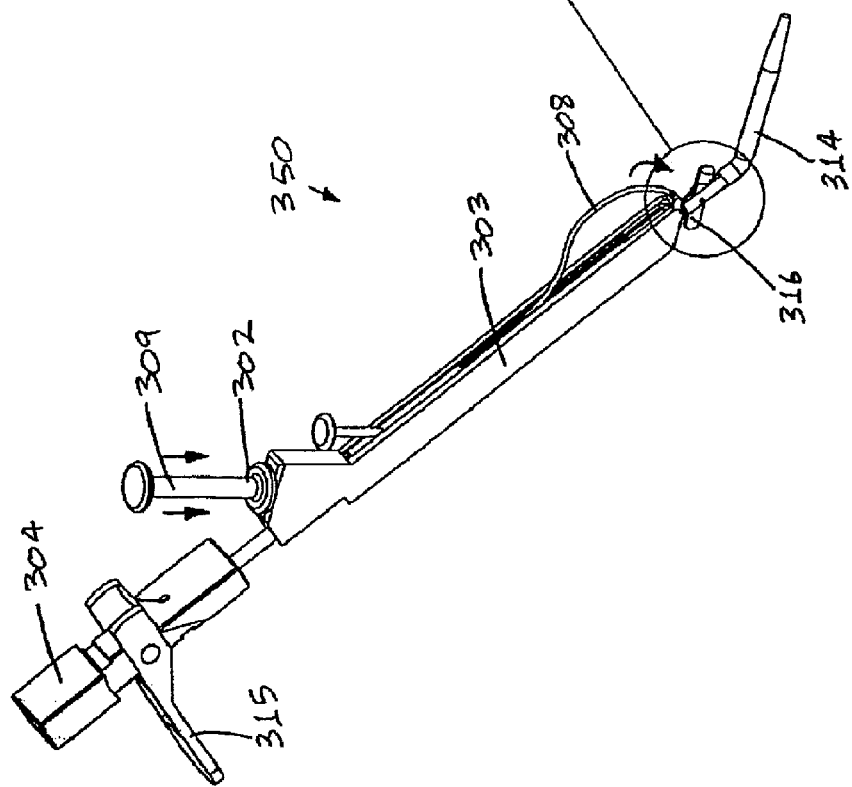
Figures 126, 127:
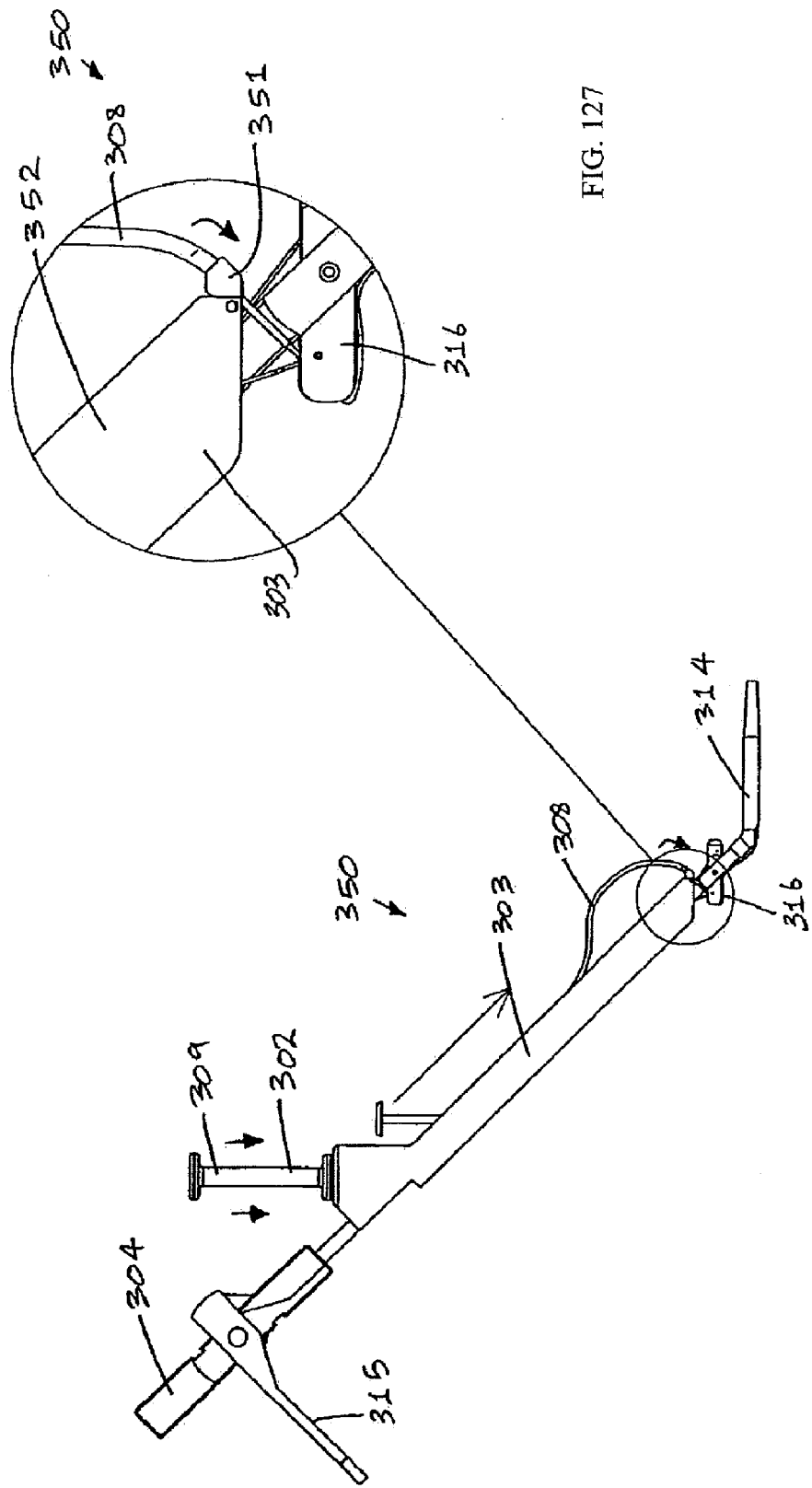
FIG. 126 is a side view of the device of FIG. 122 in the guiding configuration.
FIG. 127 is an enlarged, side view of a part of the device of FIG. 126.

In this case, the guide element 303 comprises a distal outlet port 351 out of which the engagement feature 310 of the grasping element 302 may pass out of the first lumen 311, and a main body portion 352. The outlet port 351 is rotatably movable relative to the main body portion 352 between a low-profile, delivery configuration (FIG. 122) and a protruding, guiding configuration (FIG. 124). The outlet port 351 is rotatable in the range of from 70° to 130°, in one embodiment, in the range of from 80° to 120°, and in this case approximately 105°.

The device 350 is similar to the device 300 of FIGS. 70 to 121 but utilises the expanding arm 351. This reduces the profile of the device 350 that has to be inserted through the skin and tissue tract 344. The expandable arm 351 is only deployed once the device 350 is in position at the vessel wall, and the arm 351 is retracted once the suture 305 has been picked up.

The invention is not limited to the embodiments hereinbefore described, with reference to the accompanying drawings, which may be varied in construction and detail.

The invention claimed is:

1. A method of performing an interventional procedure, the method comprising the steps of:
    creating an opening through a tissue wall; and
    moving a closure element through a first part of the tissue wall on a first side of the opening, across the opening, and through a second part of the tissue wall on a second side of the opening, bisecting the opening to assist in closure of the opening, the closure element having a first engagement element abutting the first side of the opening and the second engagement element abuts the second side of the opening; wherein a longitudinal axis of the opening intersects an external surface of the tissue at a first intersection point, an axis along which the closure element is moved intersects the external surface of the tissue at a second intersection point, the longitudinal axis of the opening intersects the axis along which the closure element is moved at a third intersection point, and a transverse axis of the lumen extends perpendicular to a longitudinal axis of the lumen through the third intersection point, the first intersection point and the second intersection point being on opposite sides of the transverse axis.

2. A method as claimed in claim 1, wherein the first engagement element exerts a compressive force on the first part of the tissue wall and the second engagement element exerts a compressive force on the second part of the tissue wall.

3. A method as claimed in claim 1, further comprising advancing a locking element over the closure element, the locking element engaging the second part of the tissue wall.

4. A method as claimed in claim 3, wherein the first portion exerts a compressive force on an internal surface of the tissue wall and the locking element exerts a compressive force on an external surface of the tissue wall.

* * * * *